US010193079B2

(12) United States Patent
Stoessel et al.

(10) Patent No.: US 10,193,079 B2
(45) Date of Patent: Jan. 29, 2019

(54) MATERIALS FOR ELECTRONIC DEVICES

(71) Applicant: Merck Patent GmbH, Darmstadt (DE)

(72) Inventors: Philipp Stoessel, Frankfurt am Main (DE); Amir Hossain Parham, Frankfurt am Main (DE); Christof Pflumm, Darmstadt (DE); Anja Jatsch, Frankfurt am Main (DE)

(73) Assignee: Merck Patent GmbH (DE)

( * ) Notice: Subject to any disclaimer, the term of this patent is extended or adjusted under 35 U.S.C. 154(b) by 207 days.

(21) Appl. No.: 14/778,829

(22) PCT Filed: Mar. 4, 2014

(86) PCT No.: PCT/EP2014/000537
§ 371 (c)(1),
(2) Date: Sep. 21, 2015

(87) PCT Pub. No.: WO2014/146752
PCT Pub. Date: Sep. 25, 2014

(65) Prior Publication Data

US 2016/0072076 A1 Mar. 10, 2016

(30) Foreign Application Priority Data

Mar. 22, 2013 (EP) .................................... 13001486

(51) Int. Cl.
*H01L 51/54* (2006.01)
*C09K 11/06* (2006.01)
(Continued)

(52) U.S. Cl.
CPC ........ *H01L 51/0072* (2013.01); *C07D 209/80* (2013.01); *C07D 209/82* (2013.01); *C07D 209/86* (2013.01); *C07D 209/94* (2013.01); *C07D 219/02* (2013.01); *C07D 241/46* (2013.01); *C07D 265/10* (2013.01); *C07D 279/26* (2013.01); *C07D 279/36* (2013.01); *C07D 401/10* (2013.01); *C07D 403/04* (2013.01); *C07D 403/10* (2013.01); *C07D 403/14* (2013.01); *C07D 413/10* (2013.01); *C07D 471/04* (2013.01); *C07D 487/04* (2013.01); *C07D 487/14* (2013.01); *C07D 491/04* (2013.01); *C07D 491/048* (2013.01);
(Continued)

(58) Field of Classification Search
CPC .. C07D 209/56; C07D 209/80; C07D 209/82; C07D 209/86; C07D 209/94; C07D 241/46; C07D 219/00; C07D 219/02; C07D 265/10; C07D 279/26; C07D 279/36; C07D 401/00; C07D 401/02; C07D 401/04; C07D 401/10; C07D 401/14; C07D 403/00; C07D 403/02; C07D 403/04; C07D 403/10; C07D 403/14; C07D 413/00; C07D 413/02; C07D 413/04; C07D 413/10; C07D 413/14; C07D 471/00; C07D 471/02; C07D 471/04; C07D 471/10; C07D 471/12; C07D 471/14; C07D 471/22; C07D 487/00; C07D 487/02; C07D 487/04; C07D 487/10; C07D 487/12; C07D 487/14; C07D 491/00; C07D 491/02; C07D 491/04; C07D 491/048; C07D 491/052; C07D 491/10; C07D 491/12; C09K 11/06; C09K 2211/00; C09K 2211/10; C09K 2211/1003; C09K 2211/1007; C09K 2211/1018; C09K 2211/1029; C09K 2211/1037; C09K 2211/1033; H01L 51/0032; H01L 51/005; H01L 51/0062; H01L 51/0067; H01L 51/0065; H01L 51/0068; H01L 51/0071; H01L 51/0072; H01L 51/0073; H01L 51/0075; H01L 51/50; H01L 51/5012; H01L 51/5016
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | | |
|---|---|---|---|---|
| 2008/0169755 A1* | 7/2008 | Kim | C07D 209/88 313/504 |
| 2009/0072727 A1* | 3/2009 | Takeda | C09K 11/06 313/504 |

(Continued)

FOREIGN PATENT DOCUMENTS

| | | |
|---|---|---|
| CN | 101600777 A | 12/2009 |
| DE | 112006002147 T5 | 10/2008 |

(Continued)

OTHER PUBLICATIONS

Gilman, H., et al., "The Di-metalation of 9-Phenylcarbazole", Journal of American Chemistry Society, vol. 65, (1943), pp. 1729-1733, XP-002723834.

(Continued)

*Primary Examiner* — Andrew K Bohaty
(74) *Attorney, Agent, or Firm* — Drinker Biddle & Reath LLP

(57) ABSTRACT

The present application relates to a compound of a formula (I) which comprises a benzene group that is substituted with a group selected from carbazole derivatives and bridged amines and with an electron attracting group, wherein the two groups are located in the ortho-position in relation to one another. The present application further relates to the use of the compound of the formula (I) in an electronic device, and to a method of producing the compound of the formula (I).

19 Claims, No Drawings

(51) Int. Cl.

| | |
|---|---|
| ***H01L 51/00*** | (2006.01) |
| ***C07D 219/02*** | (2006.01) |
| ***C07D 401/10*** | (2006.01) |
| ***C07D 403/04*** | (2006.01) |
| ***C07D 403/14*** | (2006.01) |
| ***C07D 413/10*** | (2006.01) |
| ***C07D 241/46*** | (2006.01) |
| ***C07D 487/04*** | (2006.01) |
| ***C07D 265/10*** | (2006.01) |
| ***C07D 491/04*** | (2006.01) |
| ***C07D 279/36*** | (2006.01) |
| ***C07D 209/82*** | (2006.01) |
| ***C07D 209/80*** | (2006.01) |
| ***C07D 209/86*** | (2006.01) |
| ***C07D 209/94*** | (2006.01) |
| ***C07D 279/26*** | (2006.01) |
| ***C07D 403/10*** | (2006.01) |
| ***C07D 471/04*** | (2006.01) |
| ***C07D 487/14*** | (2006.01) |
| ***C07D 491/048*** | (2006.01) |
| *H01L 51/50* | (2006.01) |

(52) U.S. Cl.

CPC .......... *C09K 11/06* (2013.01); *H01L 51/0067* (2013.01); *H01L 51/0071* (2013.01); *C09K 2211/1007* (2013.01); *C09K 2211/1029* (2013.01); *C09K 2211/1037* (2013.01); *H01L 51/0068* (2013.01); *H01L 51/5012* (2013.01)

(56) References Cited

U.S. PATENT DOCUMENTS

| | | | |
|---|---|---|---|
| 2009/0302752 | A1 | 12/2009 | Parham et al. |
| 2014/0231715 | A1 | 8/2014 | Stoessel et al. |
| 2015/0105564 | A1 | 4/2015 | Adachi et al. |

FOREIGN PATENT DOCUMENTS

| | | | |
|---|---|---|---|
| GB | 2443774 | A | 5/2008 |
| JP | 2004178896 | A | 6/2004 |
| JP | 2004/288381 | A | 10/2004 |
| JP | 2009094486 | A | 4/2009 |
| JP | 2014043541 | A | 3/2014 |
| JP | 2014135466 | A | 7/2014 |
| WO | WO-2007020954 | A1 | 2/2007 |
| WO | WO-2012143079 | A1 | 10/2012 |
| WO | WO-2013154064 | A1 | 10/2013 |

OTHER PUBLICATIONS

International Search Report for PCT/EP2014/000537 dated May 16, 2014.

Kitagawa, T., et al., "Bis(2,6-Difluorophenyl)Benzoymethyl Cation: α-Ketocarbenium Ion as a Single-Electron Acceptor", Tetrahedron Letters, vol. 32, No. 27, (1991), pp. 3187-3190, XP-002723835.

Uoyama, H., et al., "Highly efficient organic light-emitting diodes from delayed fluorescence", Nature, 2012, vol. 492, pp. 234-238.

Japanese Office Action for Japanese Application No. 2016-504509, dated Mar. 13, 2018.

* cited by examiner

MATERIALS FOR ELECTRONIC DEVICES

CROSS-REFERENCE TO RELATED APPLICATIONS

This application is a national stage application (under 35 U.S.C. § 371) of PCT/EP2014/000537, filed Mar. 4, 2014, which claims benefit of European Application No. 13001486.3, filed Mar. 22, 2013, both of which are incorporated herein by reference in their entirety.

The present application relates to a compound of a formula (I) having a benzene group substituted by a group selected from carbazole derivatives and bridged amines and having an electron-withdrawing group, where the two groups are in ortho positions to one another. The compound can be used in an electronic device.

Electronic devices in the context of this application are especially understood to mean what are called organic electronic devices, which contain organic semiconductor materials as functional materials. Even more particularly, this is understood to mean organic electroluminescent devices (OLEDs) and other electronic devices which are mentioned hereinafter in the detailed description of the invention.

In general, the term OLED is understood to mean an electronic device which contains at least one organic material and emits light on application of electrical voltage. The exact structure of OLEDs is described, inter alia, in U.S. Pat. Nos. 4,539,507, 5,151,629, EP 0676461 and WO 98/27136.

In electronic devices, especially OLEDs, there is great interest in improving the performance data, especially lifetime and efficiency and operating voltage. An important role is played by organic emitter layers, especially the emitter compounds present therein.

To solve this technical problem, there is a continuous search for new materials suitable for use as emitter compounds in emitting layers, especially in combination with a matrix material.

A matrix material in a system comprising two or more materials is understood to mean that component having the greater proportion in the mixture. Correspondingly, a dopant in a system comprising two or more materials is understood to mean that component having the smaller proportion in the mixture.

In the context of the present application, emitter compounds of an emitting layer are compounds which emit light on operation of the electronic device.

In emitting layers of OLEDs, the dopant compound(s) are generally the emitting compounds, and the matrix compound(s) are not light-emitting. However, there may also be exceptions, for example compounds which are present in a small proportion in the mixture of the light-emitting layer, i.e. are regarded as dopants according to the above definition, but do not emit and instead fulfill other functions, for example charge transport.

The prior art includes compounds containing one or more carbazole groups, known, for example, from WO 2005/039246, US 2005/0069729, JP 2004/288381, EP 1205527 or WO 2008/086851. The compounds are suitable, inter alia, for use as matrix materials for emitting layers of OLEDs or as compounds for electron-transporting layers of OLEDs.

In addition, WO 2012/143079 discloses compounds having three carbazole groups in the 1,3,5 positions on a benzene. Further substituents are then selected, for example, from alkyl groups. The compounds are suitable, inter alia, for use in the emitting layer of OLEDs.

Still further compounds are disclosed in H. Uoyama et al., Nature 2012, 492, 234 ff., these containing a plurality of carbazole groups and a plurality of cyano groups bonded to a benzene ring, where the carbazole groups and the cyano groups are in a defined arrangement with respect to one another. In these compounds, there are always at least two carbazole groups arranged para to one another on the benzene ring. The compounds are used in the emitting layer of OLEDs.

In spite of these results, there is still a need for new compounds suitable for use in electronic devices, especially for use in emitting layers of OLEDs.

It has now been found that, surprisingly, compounds having at least one carbazole derivative bonded to a benzene ring and, in the ortho position thereto, at least one electron-withdrawing group, where the substituents on the benzene ring are in a defined arrangement with respect to one another, as defined in formula (I) below, are of very good suitability for use in electronic devices. More particularly, they are outstandingly suitable for use as emitter compounds in emitting layers.

OLEDs containing the compounds surprisingly have a very good power efficiency and a very long lifetime. In addition, they preferably have a low operating voltage. Furthermore, when used as emitter compound, they can potentially cover the entire color spectrum of emission.

The present application thus provides a compound of the formula (I)

Formula (I)

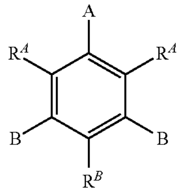

or a compound containing exactly two or three units of the formula (I) joined to one another via a single bond or an L group, where:

L is any divalent or trivalent organic group;

A is a group of the formula (A)

Formula (A)

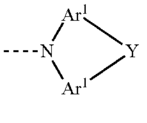

bonded via the dotted bond;

$Ar^1$ is the same or different at each instance and is an aromatic or heteroaromatic ring system which has 5 to 30 aromatic ring atoms and may be substituted by one or more $R^1$ radicals;

Y is the same or different at each instance and is a single bond, $BR^1$, $C(R^1)_2$, $Si(R^1)_2$, $NR^1$, $PR^1$, $P({=}O)R^1$, O, S, S=O or $S(=O)_2$;

B is the same or different at each instance and is selected from a group of the formula (A), H, D, a straight-chain alkyl group having 1 to 20 carbon atoms or a branched or cyclic alkyl group having 3 to 20 carbon atoms, each of which may be substituted by one or more $R^1$ radicals, where one or more $CH_2$ groups in the abovementioned groups may be replaced by $—R^1C═CR^1—$, —C≡C—, $Si(R^1)_2$, C═O, $C═NR^1$, —C(═O)O—, $—C(═O)NR^1—$, $NR^1$, $P(═O)(R^1)$, —O—, —S—, SO or $SO_2$, and an aromatic or heteroaromatic ring system having 5 to 30 aromatic ring atoms, each of which may be substituted by one or more $R^1$ radicals;

$R^A$ is the same or different at each instance and is F, $CF_3$, $C(═O)R^1$, CN, $P(═O)(R^1)_2$, $S(═O)R^1$, $S(═O)_2R^1$, a straight-chain alkyl group having 1 to 20 carbon atoms or a branched or cyclic alkyl group which has 3 to 20 carbon atoms, each of which may be substituted by one or more $R^1$ radicals, and where one or more $CH_2$ groups in the abovementioned groups may be replaced by $—R^1C═CR^1—$, —C≡C—, $Si(R^1)_2$, C═O, $C═NR^1$, —C(═O)O—, $—C(═O)NR^1—$, $NR^1$, $P(═O)(R^1)$, —S—, SO or $SO_2$, or an aromatic ring system which has 6 to 30 aromatic ring atoms and may be substituted by one or more $R^1$ radicals, or a heteroaromatic ring system having 5 to 30 aromatic ring atoms which is not bonded via a ring nitrogen atom and which may be substituted by one or more $R^1$ radicals, where $R^A$ radicals may be joined to $R^1$ radicals and may form a ring;

$R^B$ is selected from H, D and the radicals listed above for $R^A$, where $R^B$ radicals may be joined to $R^1$ radicals and may form a ring;

$R^1$ is the same or different at each instance and is H, D, F, $C(═O)R^2$, CN, $Si(R^2)_3$, $N(R^2)_2$, $P(═O)(R^2)_2$, $OR^2$, $S(═O)R^2$, $S(═O)_2R^2$, a straight-chain alkyl or alkoxy group having 1 to 20 carbon atoms or a branched or cyclic alkyl or alkoxy group having 3 to 20 carbon atoms, where the abovementioned groups may each be substituted by one or more $R^2$ radicals and where one or more $CH_2$ groups in the abovementioned groups may be replaced by $—R^2C═CR^2—$, —C≡C—, $Si(R^2)_2$, C═O, $C═NR^2$, —C(═O)O—, $—C(═O)NR^2—$, $NR^2$, $P(═O)(R^2)$, —O—, —S—, SO or $SO_2$, or an aromatic or heteroaromatic ring system having 5 to 30 aromatic ring atoms, each of which may be substituted by one or more $R^2$ radicals, where two or more $R^1$ radicals may be joined to one another and may form a ring;

$R^2$ is the same or different at each instance and is H, D, F or an aliphatic, aromatic or heteroaromatic organic radical having 1 to 20 carbon atoms, in which one or more hydrogen atoms may also be replaced by D or F; at the same time, two or more $R^2$ substituents may be joined to one another and may form a ring;

with the proviso that at least one $R^A$ radical is selected from F, $CF_3$, $CF_2H$, $CFH_2$, $C(═O)R^1$, CN, $P(═O)(R^1)_2$, $S(═O)R^1$, $S(═O)_2R^1$ and an E group, which is an aryl or heteroaryl group which has 6 to 18 aromatic ring atoms and may be substituted by one or more $R^1$ radicals, and which contains one or more V groups as constituents of the aromatic ring, where the V groups are the same or different at each instance and are selected from ═N—, ═C(F)—, ═C(CN)— and $═C(CF_3)—$.

Heteroaromatic ring systems bonded via a ring nitrogen atom are especially understood to mean derivatives of carbazole, indenocarbazole, indolocarbazole, pyrrole and imidazole, which are bonded via their corresponding nitrogen atom having a free valence.

An aryl group in the context of this invention contains 6 to 60 aromatic ring atoms; a heteroaryl group in the context of this invention contains 5 to 60 aromatic ring atoms, at least one of which is a heteroatom. The heteroatoms are preferably selected from N, O and S. This is the fundamental definition. If other preferences are stated in the description of the present invention, for example with regard to the number of aromatic ring atoms or of heteroatoms present, these are applicable.

An aryl group or heteroaryl group is understood here to mean either a simple aromatic cycle, i.e. benzene, or a simple heteroaromatic cycle, for example pyridine, pyrimidine or thiophene, or a fused (annelated) aromatic or heteroaromatic polycycle, for example naphthalene, phenanthrene, quinoline or carbazole. A fused (annelated) aromatic or heteroaromatic polycycle, in the context of the present application, consists of two or more simple aromatic or heteroaromatic cycles fused to one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 60 carbon atoms in the ring system. A heteroaromatic ring system in the context of this invention contains 5 to 60 aromatic ring atoms, at least one of which is a heteroatom. The heteroatoms are preferably selected from N, O and/or S. An aromatic or heteroaromatic ring system in the context of this invention is understood to mean a system which does not necessarily contain only aryl or heteroaryl groups, but in which it is also possible for two or more aryl or heteroaryl groups to be bonded by a nonaromatic unit (preferably less than 10% of the atoms other than H), for example an $sp^3$-hybridized carbon, silicon, nitrogen or oxygen atom, an $sp^2$-hybridized carbon or nitrogen atom or an sp-hybridized carbon atom. For example, systems such as 9,9'-spirobifluorene, 9,9'-diarylfluorene, triarylamine, diaryl ethers, stilbene, etc. are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl or heteroaryl groups are joined to one another via single bonds are also to be regarded as aromatic or heteroaromatic ring systems in the context of this invention, for example systems such as biphenyl, terphenyl or diphenyltriazine.

An aromatic or heteroaromatic ring system which has 5-60 aromatic ring atoms and may also be substituted in each case by radicals as defined above and which may be joined to the aromatic or heteroaromatic system via any desired positions is especially understood to mean groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

In the context of the present invention, a straight-chain alkyl group having 1 to 40 carbon atoms and a branched or cyclic alkyl group having 3 to 40 carbon atoms and an alkenyl or alkynyl group having 2 to 40 carbon atoms in which individual hydrogen atoms or $CH_2$ groups may also be replaced by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals. An alkoxy or thioalkyl group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. This is illustrated by the following scheme:

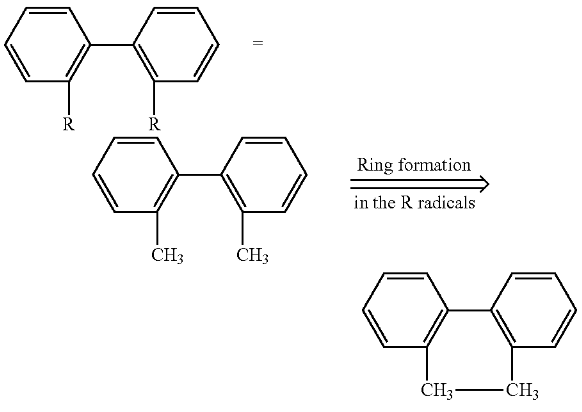

In addition, however, the abovementioned wording shall also be understood to mean that, if one of the two radicals is hydrogen, the second radical binds to the position to which the hydrogen atom was bonded, forming a ring. This shall be illustrated by the following scheme:

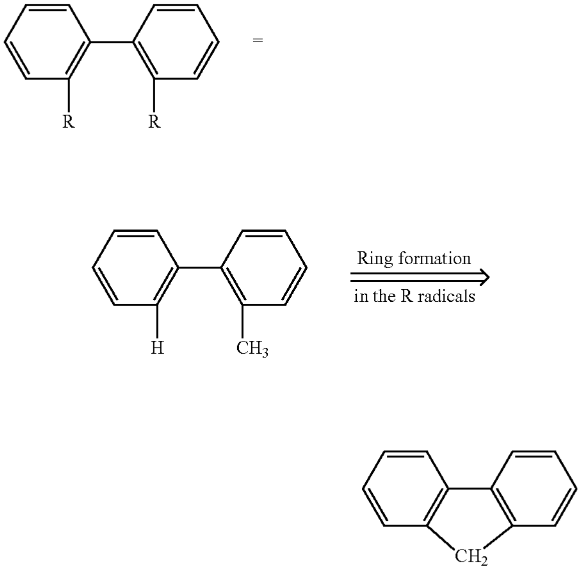

The L group is preferably a divalent group selected from alkylene groups having 1 to 20 carbon atoms, in which one or more $CH_2$ groups may be replaced by $Si(R^1)_2$, O, S, C=O, $C=NR^1$, C=O—O, $C=O—NR^1$, $NR^1$, $P(=O)(R^1)$, SO or $SO_2$ and which may be substituted by one or more $R^1$ radicals, or aromatic or heteroaromatic ring systems having 5 to 30 aromatic ring atoms, each of which may be substituted by one or more $R^1$ radicals, or is a trivalent group selected from aromatic or heteroaromatic ring systems having 5 to 30 aromatic ring atoms, each of which may be substituted by one or more $R^1$ radicals.

Formula (A) preferably corresponds to one of the following formulae (A-1) to (A-22), which are bonded via the dotted bond:

Formula (A-1)
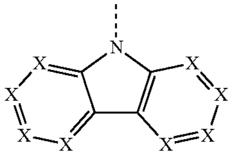
Formula (A-2)
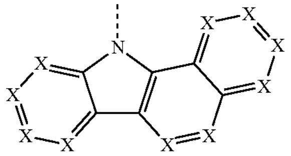
Formula (A-3)
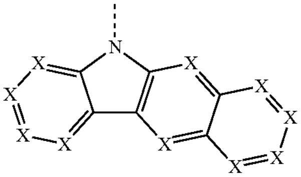
Formula (A-4)
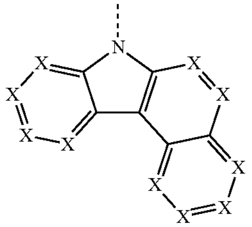
Formula (A-5)
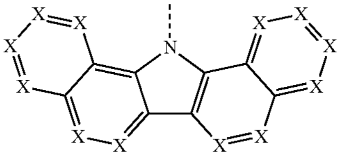
Formula (A-6)
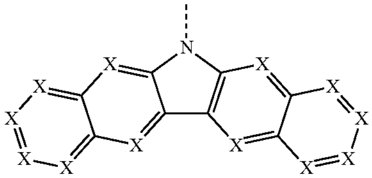
Formula (A-7)
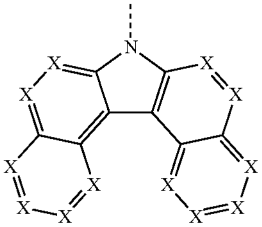
Formula (A-8)
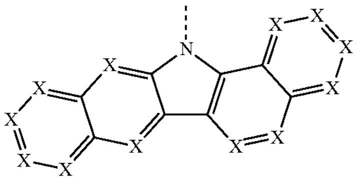
-continued
Formula (A-9)
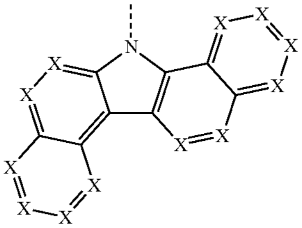
Formula (A-10)
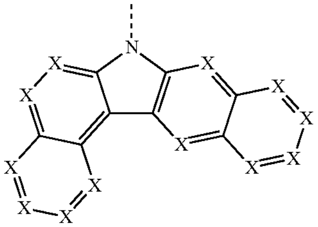
Formula (A-11)
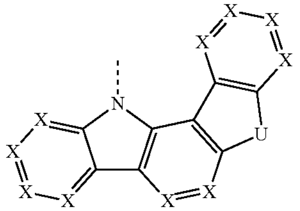
Formula (A-12)
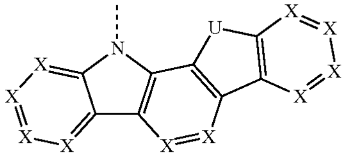
Formula (A-13)
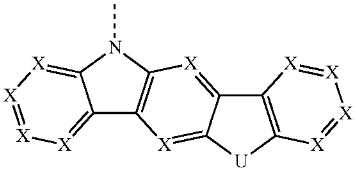
Formula (A-14)
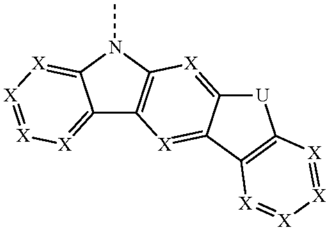
Formula (A-15)
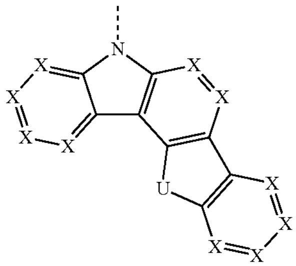

-continued

Formula (A-16)

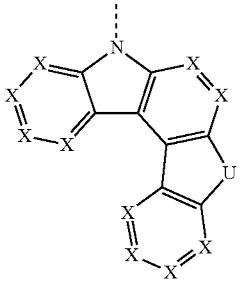

Formula (A-17)

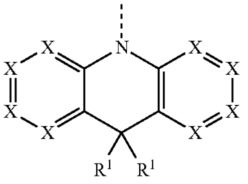

Formula (A-18)

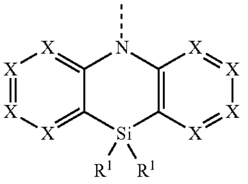

Formula (A-19)

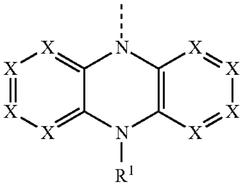

Formula (A-20)

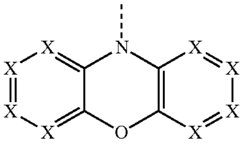

Formula (A-21)

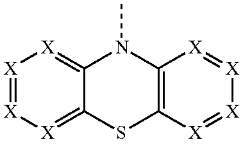

Formula (A-22)

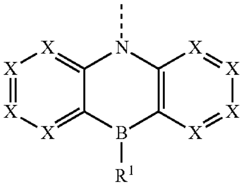

where:

X is the same or different at each instance and is $CR^1$ or N;

U is $BR^1$, $C(R^1)_2$, $Si(R^1)_2$, $NR^1$, O or S; and $R^1$ is as defined above.

Among the formulae (A-1) to (A-22), preference is given to the formulae (A-1), (A-4), (A-14) and (A-17).

When U is a $C(R^1)_2$ or $Si(R^1)_2$ group, it is preferable that the two $R^1$ groups in the group are joined to one another and form a ring. This preferably forms a five- or six-membered ring. This more preferably forms a spiro-bifluorene group.

It is preferable for the above formulae that X is $CR^1$.

It is additionally preferable for the above formulae that not more than three X groups per ring are N. It is additionally preferable that not more than two adjacent X groups in one ring are N. More preferably, exactly one X group per ring is N, or no X group in a ring is N.

Preferably, the U group in the above formulae is $C(R^1)_2$ or $NR^1$, more preferably $C(R^1)_2$.

Particular preference is given to combinations of the abovementioned preferred embodiments with one another.

Preferably, $Ar^1$ is the same or different at each instance and is an aromatic ring system which has 6 to 20 aromatic ring atoms and may be substituted by one or more $R^1$ radicals, and more preferably phenyl, pyridyl, naphthyl, fluorenyl or carbazolyl, each of which may be substituted by one or more $R^1$ radicals.

Preferably, the Y group is the same or different at each instance and is a single bond, $C(R^1)_2$, $NR^1$, O or S, more preferably a single bond.

For the B group, it is preferable in accordance with the invention that it is the same or different at each instance and is selected from a group of the formula (A), H, a straight-chain alkyl group having 1 to 10 carbon atoms or a branched or cyclic alkyl group having 3 to 10 carbon atoms, each of which may be substituted by one or more $R^1$ radicals, or an aryl group having 6 to 14 aromatic ring atoms, each of which may be substituted by one or more $R^1$ radicals. When the B group is selected from a group of the formula (A), it is preferable that it is selected from groups of the formulae (A-1) to (A-22).

More preferably, the B group is the same or different at each instance and is a group of the formula (A) or H. Most preferably, the B group is a group of the formula (A). When the B group is a group of the formula (A), it is preferable that it is selected from groups of the formulae (A-1) to (A-22).

It is apparent from the definition of $R^A$ and $R^B$ that these cannot be a carbazole or carbazole derivative bonded via the nitrogen atom.

For the $R^A$ radical, it is preferable in accordance with the invention that it is the same or different at each instance and is selected from F, $CF_3$, CN, a straight-chain alkyl group having 1 to 10 carbon atoms or a branched or cyclic alkyl group having 3 to 10 carbon atoms, each of which may be substituted by one or more $R^1$ radicals, or an aryl or heteroaryl group having 6 to 14 aromatic ring atoms which may be substituted by one or more $R^1$ radicals, where the heteroaryl group is not bonded via a nitrogen atom, with the proviso that at least one $R^A$ radical is selected from F, $CF_3$, CN, and an E group, which is an aryl or heteroaryl group which has 6 to 14 aromatic ring atoms and may be substituted by one or more $R^1$ radicals, and which contains one or more V groups as constituents of the aromatic ring, where the V groups are the same or different at each instance and are selected from =N—, =C(F)—, =C(CN)— and $=C(CF_3)—$.

More preferably, the two $R^A$ radicals are the same or different and are selected from F, $CF_3$, CN, and an E group, which is an aryl or heteroaryl group which has 6 to 14 aromatic ring atoms and may be substituted by one or more $R^1$ radicals, and which contains one or more V groups as constituents of the aromatic ring, where the V groups are the same or different at each instance and are selected from =N—, =C(F)—, =C(CN)— and $=C(CF_3)—$. The heteroaryl group is not bonded via a nitrogen atom.

It is preferable that at least two V groups are present in the E groups, more preferably two, three, four or five.

The E group is preferably a group of the formula (E-1) to (E-9) bonded via the dotted bond Formula (E-1)

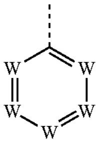

Formula (E-2)

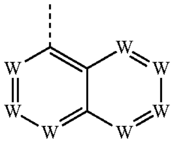

Formula (E-3)

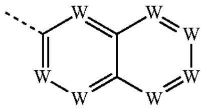

Formula (E-4)

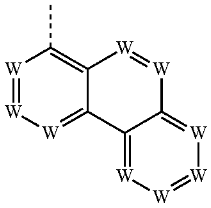

Formula (E-5)

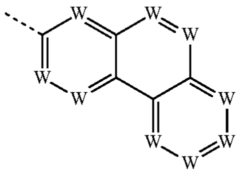

Formula (E-6)

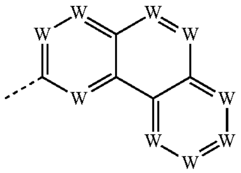

Formula (E-7)

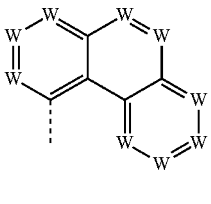

Formula (E-8)

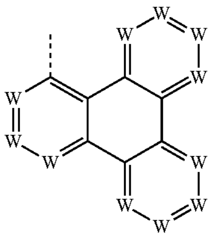

-continued

Formula (E-9)

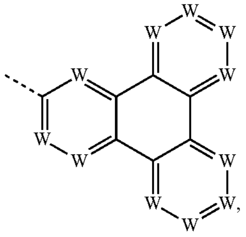

where:

W is the same or different at each instance and is $CR^1$ or V, where at least one W group is V; and where V and $R^1$ are each as defined above.

Among the groups of the formulae (E-1) to (E-9), preference is given to the group of the formula (E-1).

Preferably, in the groups of the formulae (E-1) to (E-9), at least two W groups are V, more preferably exactly two, three, four or five.

It is additionally preferable that not more than two V groups that are =N— are present alongside one another in a ring. Additionally preferably, not more than three V groups that are =N— are present in a ring.

Particularly preferred embodiments of the E groups correspond to the following formulae (E1-1) to (E-1-89)

(E-1-1)

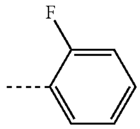

(E-1-2)

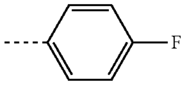

(E-1-3)

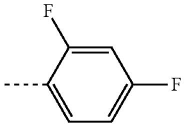

(E-1-4)

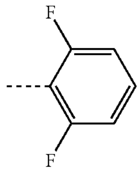

(E-1-5)

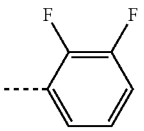

(E-1-6)

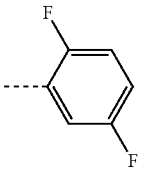

-continued
(E-1-7)
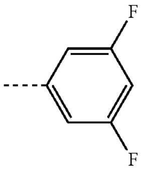
(E-1-8)
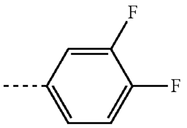
(E-1-9)
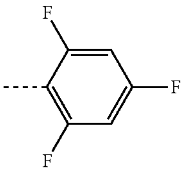
(E-1-10)
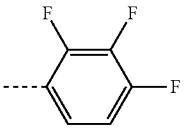
(E-1-11)
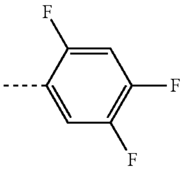
(E-1-12)
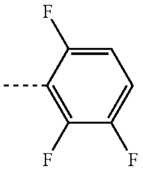
(E-1-13)
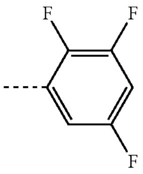
(E-1-14)
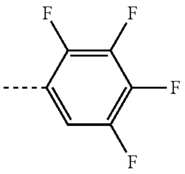
(E-1-15)
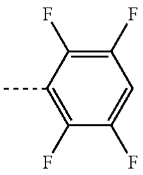
-continued
(E-1-16)
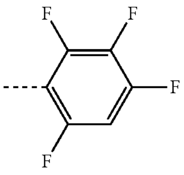
(E-1-17)
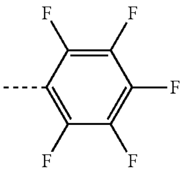
(E-1-18)
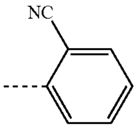
(E-1-19)
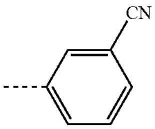
(E-1-20)
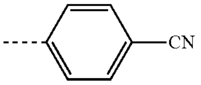
(E-1-21)
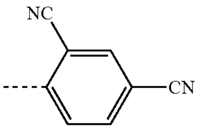
(E-1-22)
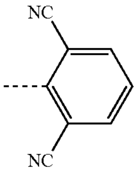
(E-1-23)
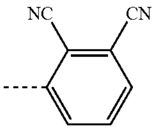
(E-1-24)
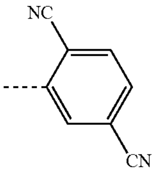
(E-1-25)
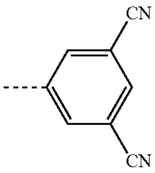

-continued
(E-1-26)
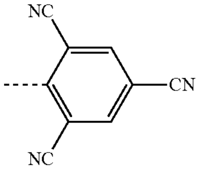
(E-1-27)
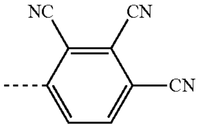
(E-1-28)
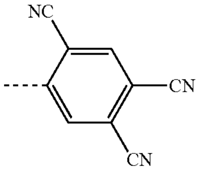
(E-1-29)
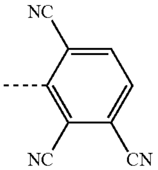
(E-1-30)
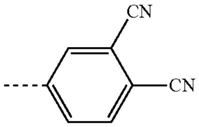
(E-1-31)
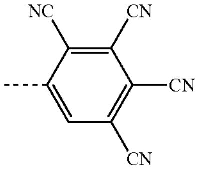
(E-1-32)
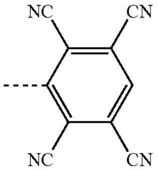
(E-1-33)
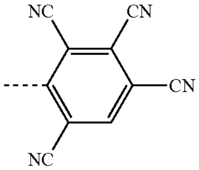
(E-1-34)
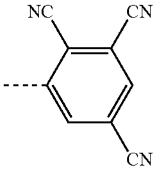
-continued
(E-1-35)
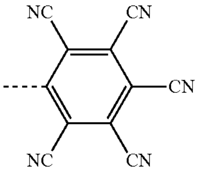
(E-1-36)
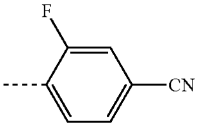
(E-1-37)
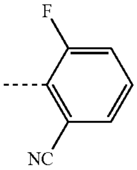
(E-1-38)
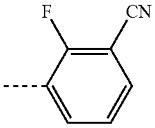
(E-1-39)
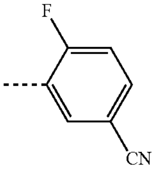
(E-1-40)
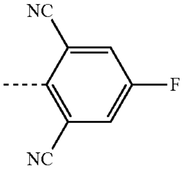
(E-1-41)
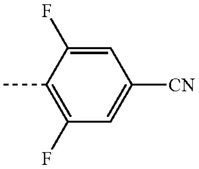
(E-1-42)
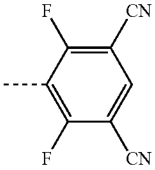
(E-1-43)
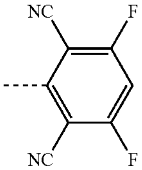

-continued
(E-1-44)
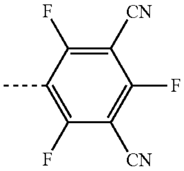
(E-1-45)
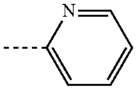
(E-1-46)
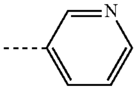
(E-1-47)
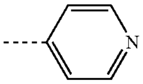
(E-1-48)
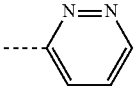
(E-1-49)
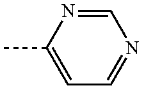
(E-1-50)
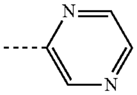
(E-1-51)
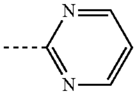
(E-1-52)
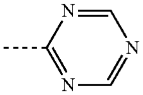
(E-1-53)
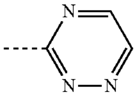
(E-1-54)
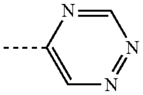
(E-1-55)
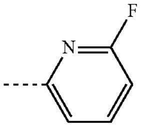
(E-1-56)
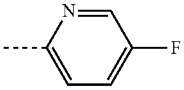
(E-1-57)
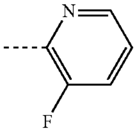
-continued
(E-1-58)
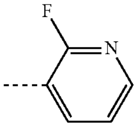
(E-1-59)
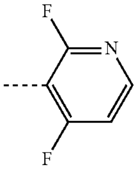
(E-1-60)
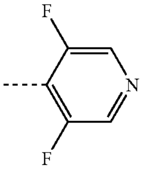
(E-1-61)
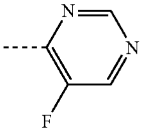
(E-1-62)
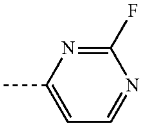
(E-1-63)
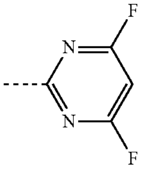
(E-1-64)
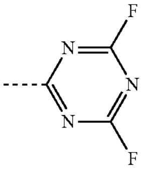
(E-1-65)
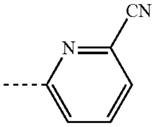
(E-1-66)
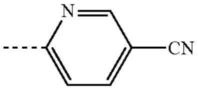
(E-1-67)
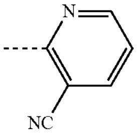

-continued
(E-1-68)
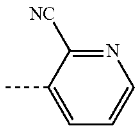
(E-1-69)
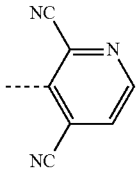
(E-1-70)
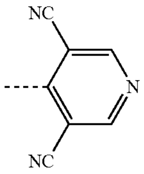
(E-1-71)
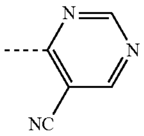
(E-1-72)
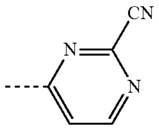
(E-1-73)
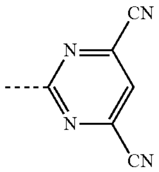
(E-1-74)
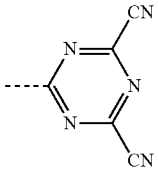
(E-1-75)
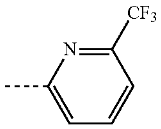
(E-1-76)
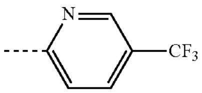
(E-1-77)
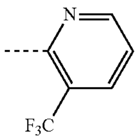
-continued
(E-1-78)
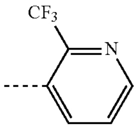
(E-1-79)
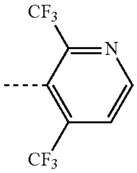
(E-1-80)
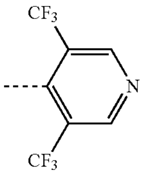
(E-1-81)
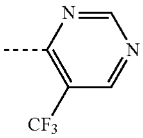
(E-1-82)
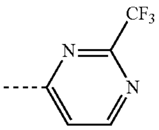
(E-1-83)
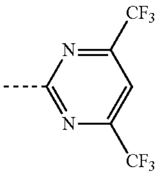
(E-1-84)
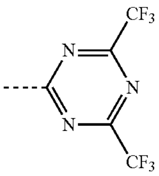
(E-1-85)
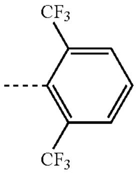
(E-1-86)
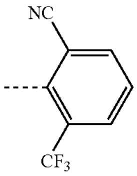

-continued (E-1-87)

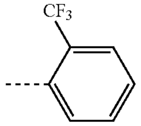

(E-1-88)

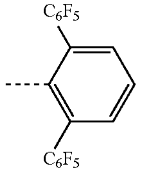

(E-1-89)

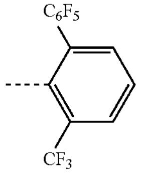

Preferably, $R^B$ is the same or different at each instance and is selected from H, F, $CF_3$, CN, a straight-chain alkyl group having 1 to 10 carbon atoms or a branched or cyclic alkyl group having 3 to 10 carbon atoms, each of which may be substituted by one or more $R^1$ radicals, and an aryl or heteroaryl group having 6 to 14 aromatic ring atoms, each of which may be substituted by one or more $R^1$ radicals, where the heteroaryl group is not bonded via a nitrogen atom. More preferably, $R^B$ is the same or different at each instance and is selected from H, F, $CF_3$, CN, and an E group, as defined above.

Preferably, the $R^1$ radical is the same or different at each instance and is H, D, F, CN, $Si(R^2)_3$, $N(R^2)_2$, a straight-chain alkyl or alkoxy group having 1 to 10 carbon atoms or a branched or cyclic alkyl or alkoxy group having 3 to 10 carbon atoms, where the abovementioned groups may each be substituted by one or more $R^2$ radicals and where one or more $CH_2$ groups in the abovementioned groups may be replaced by $—R^2C{=}CR^2—$, —C≡C—, $Si(R^2)_2$, C=O, $C{=}NR^2$, —C(=O)O—, $—C({=}O)NR^2—$, $NR^2$, $P({=}O)(R^2)$, —O—, —S—, SO or $SO_2$, or an aromatic or heteroaromatic ring system having 5 to 20 aromatic ring atoms, each of which may be substituted by one or more $R^2$ radicals, where two or more $R^1$ radicals may be joined to one another and may form a ring.

Preferred embodiments of the compounds of the formula (I) correspond to the formulae (I-1) to (I-3)

Formula (I-1)

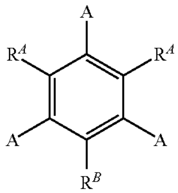

-continued

Formula (I-2)

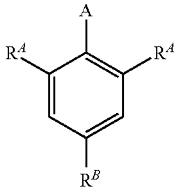

Formula (I-3)

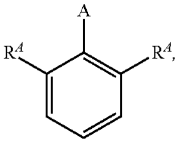

where H, D, alkyl groups having 1 to 10 carbon atoms or aromatic or heteroaromatic ring systems having 6 to 30 aromatic ring atoms, each of which may be substituted by one or more $R^1$ radicals, may optionally be bonded to the unoccupied positions on the benzene ring in formula (I-2), and where the A, $R^A$ and $R^B$ groups are each as defined above, and there is the proviso that at least one $R^A$ radical is selected from F, $CF_3$, $C({=}O)R^1$, CN, $P({=}O)(R^1)_2$, $S({=}O)R^1$, $S({=}O)_2R^1$ and an E group, which is an aryl or heteroaryl group which has 6 to 18 aromatic ring atoms and may be substituted by one or more $R^1$ radicals, and which contains one or more V groups as constituents of the aromatic ring, where the V groups are the same or different at each instance and are selected from =N—, =C(F)—, =C(CN)— and $=C(CF_3)—$. Preferably, the proviso applies to both $R^A$ radicals.

Additionally preferred is the combination of the preferred embodiments of A, B and $R^A$ and $R^B$ in particular with the formulae (I-1) to (I-3).

Especially preferably, in the formulae (I-1) to (I-3), the A group corresponds to one of the formulae (A-1) to (A-22), as defined above.

Particularly preferred embodiments of the compounds of the formula (I) are compounds of the formula (I-1-a) to (I-1-f)

Formula (I-1-a)

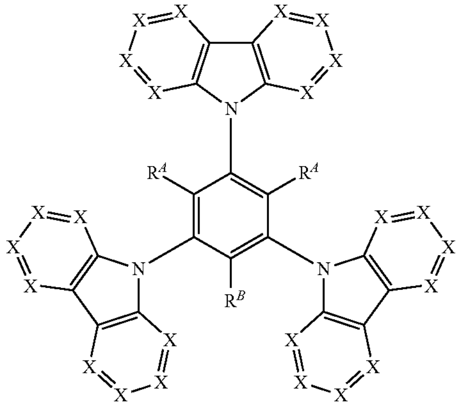

-continued

Formula (I-1-b)

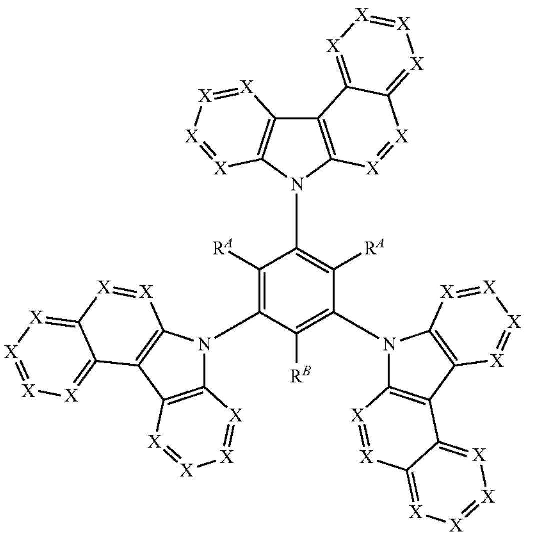

Formula (I-1-c)

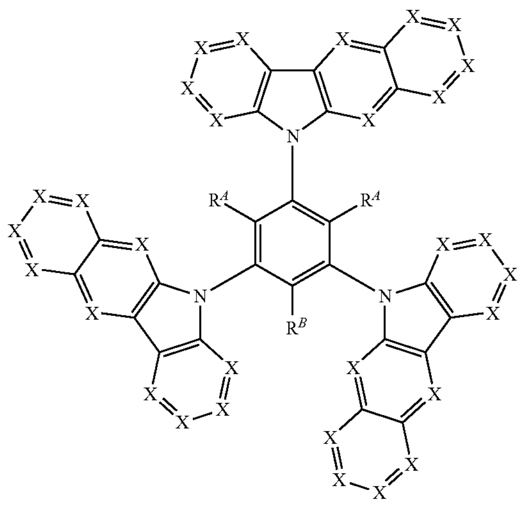

Formula (I-1-d)

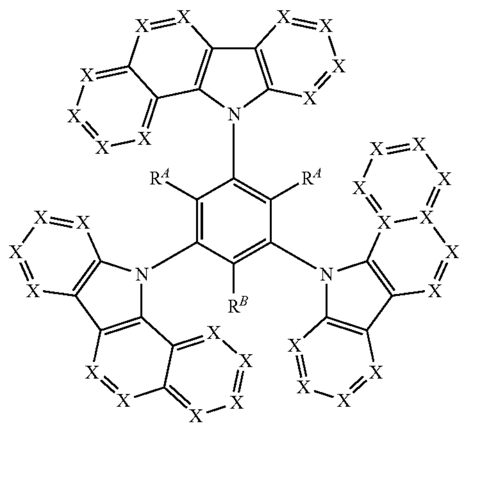

-continued

Formula (I-1-e)

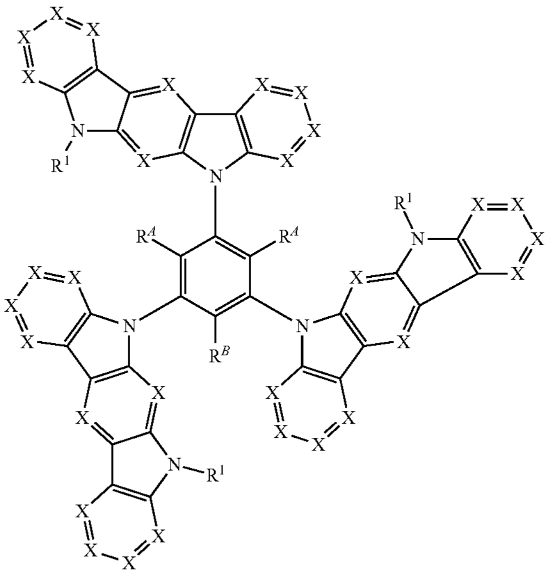

Formula (I-1-f)

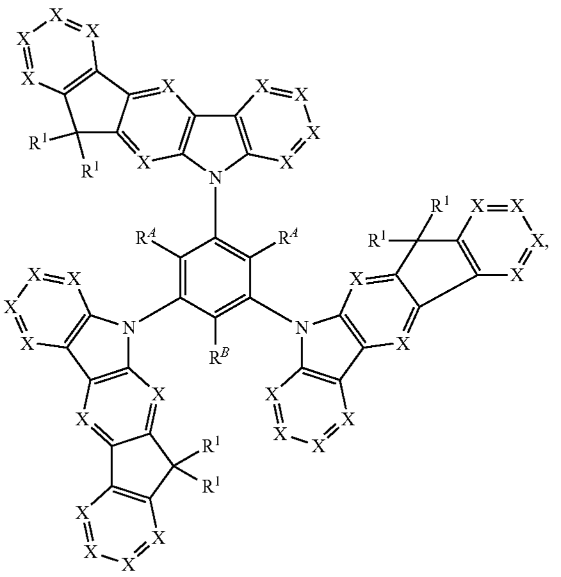

where:

X is as defined above and is preferably $CR^1$;

$R^A$ and $R^B$ are each as defined above; and where there is the proviso that at least one $R^A$ radical is selected from F, $CF_3$, $C(=O)R^1$, CN, $P(=O)(R^1)_2$, $S(=O)R^1$, $S(=O)_2R^1$ and an E group, which is an aryl or heteroaryl group which has 6 to 18 aromatic ring atoms and may be substituted by one or more $R^1$ radicals, and which contains one or more V groups as constituents of the aromatic ring, where the V groups are the same or different at each instance and are selected from $=N-$, $=C(F)-$, $=C(CN)-$ and $=C(CF_3)-$, and where the proviso preferably applies to both $R^A$ radicals.

Preferably, $R^A$ and $R^B$ are the same or different at each instance and are F, $CF_3$, CN, or an E group, as defined above.

Particularly preferred embodiments of the compounds of the formula (I) are compounds of the formula (I-2-a) to (I-2-f)

Formula (I-2-a)

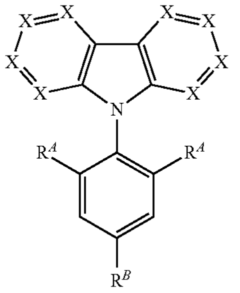

Formula (I-2-b)

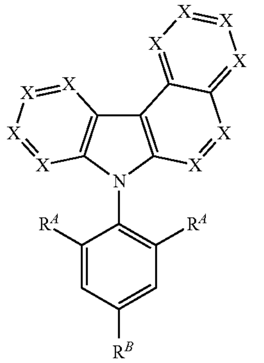

Formula (I-2-c)

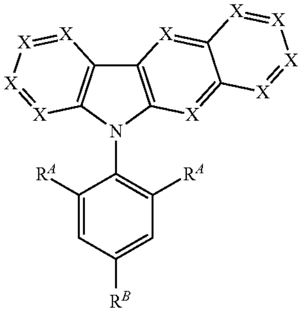

Formula (I-2-d)

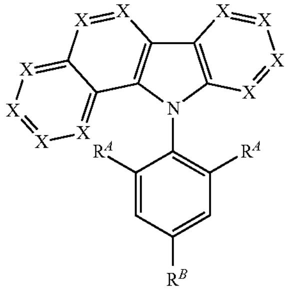

Formula (I-2-e)

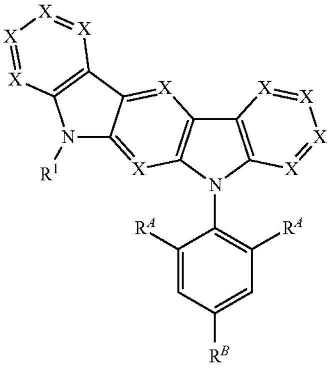

-continued

Formula (I-2-f)

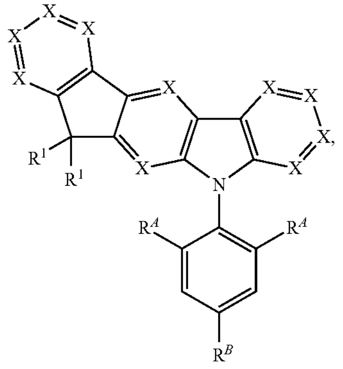

where H, D, alkyl groups having 1 to 10 carbon atoms or aromatic or heteroaromatic ring systems having 6 to 30 aromatic ring atoms, each of which may be substituted by one or more $R^1$ radicals, may optionally be bonded to the unoccupied positions on the benzene ring in formulae (I-2-1) to (I-2-f), and where:

X is as defined above and is preferably $CR^1$;

$R^A$ and $R^B$ are each as defined above; and where there is the proviso that at least one $R^A$ radical is selected from F, $CF_3$, $C(=O)R^1$, CN, $P(=O)(R^1)_2$, $S(=O)R^1$, $S(=O)_2R^1$ and an E group, which is an aryl or heteroaryl group which has 6 to 18 aromatic ring atoms and may be substituted by one or more $R^1$ radicals, and which contains one or more V groups as constituents of the aromatic ring, where the V groups are the same or different at each instance and are selected from $=N—$, $=C(F)—$, $=C(CN)—$ and $=C(CF_3)—$, and where the proviso preferably applies to both $R^A$ radicals.

Preferably, $R^A$ and $R^B$ are the same or different at each instance and are F, $CF_3$, CN, or an E group, as defined above.

Particularly preferred embodiments of the compounds of the formula (I) are compounds of the formula (I-3-a) to (I-3-f)

Formula (I-3-a)

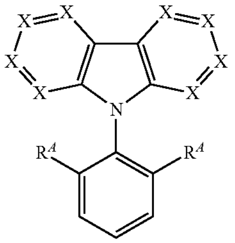

Formula (I-3-b)

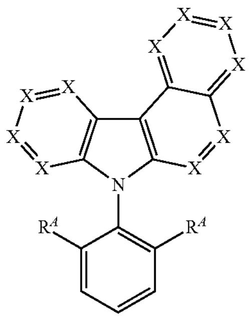

-continued

Formula (I-3-c)

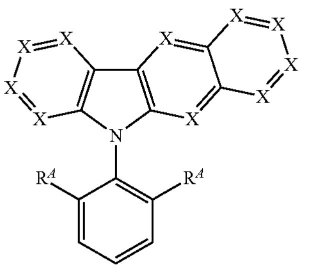

Formula (I-3-d)

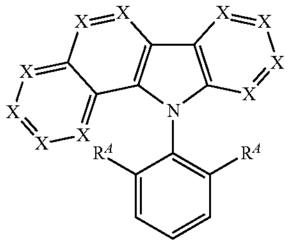

Formula (I-3-e)

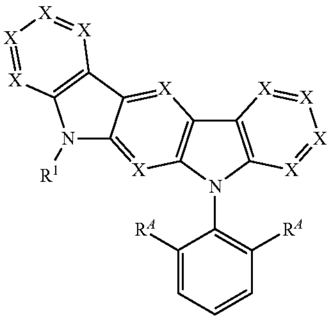

Formula (I-3-f)

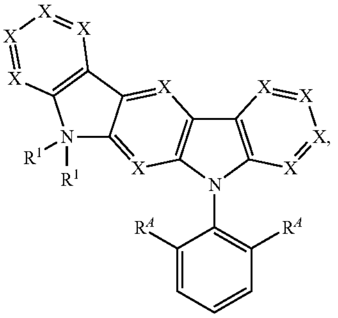

where:

X is as defined above and is preferably $CR^1$;

$R^A$ is as defined above; and where there is the proviso that at least one $R^A$ radical is selected from F, $CF_3$, $C(=O)R^1$, CN, $P(=O)(R^1)_2$, $S(=O)R^1$, $S(=O)_2R^1$ and an E group, which is an aryl or heteroaryl group which has 6 to 18 aromatic ring atoms and may be substituted by one or more $R^1$ radicals, and which contains one or more V groups as constituents of the aromatic ring, where the V groups are the same or different at each instance and are selected from $=N-$, $=C(F)-$, $=C(CN)-$ and $=C(CF_3)-$, and where the proviso preferably applies to both $R^A$ radicals.

Preferably, $R^A$ is the same or different at each instance and is F, $CF_3$, CN, or an E group, as defined above.

Examples of compounds according to the present invention are depicted below:

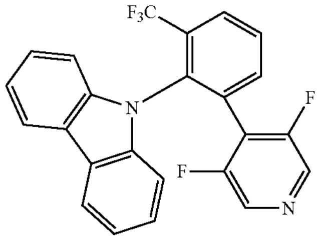
1

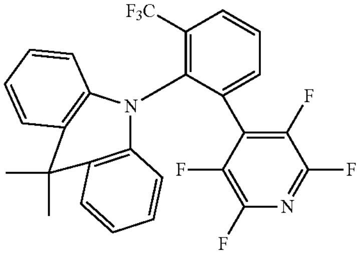
2

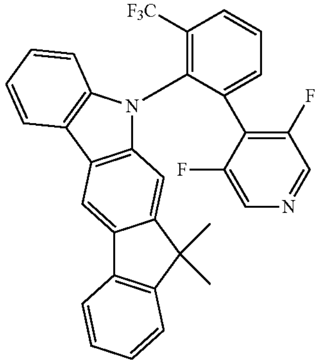
3

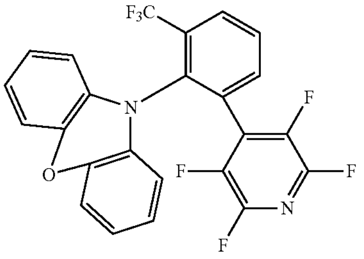
4

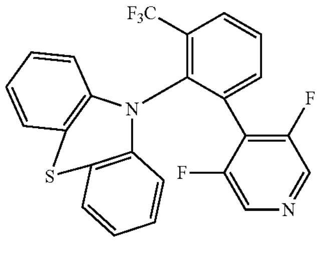
5

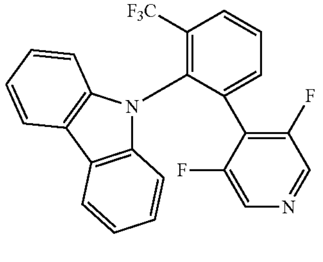
6

-continued
7
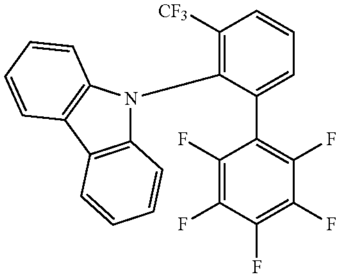
8
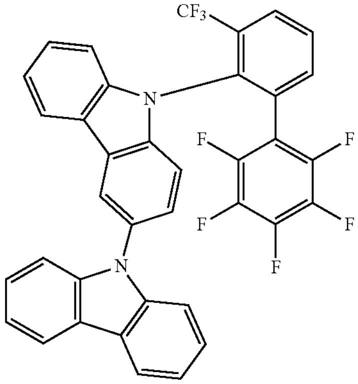
9
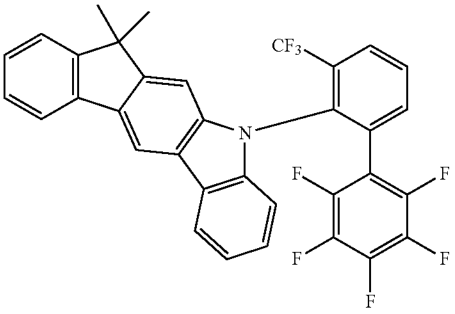
10
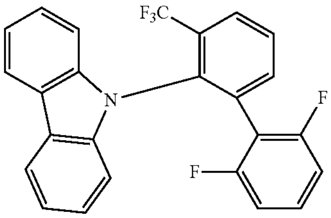
11
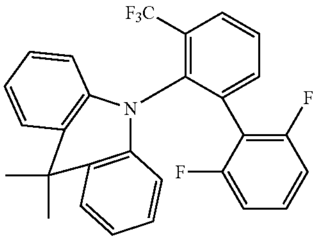
-continued
12
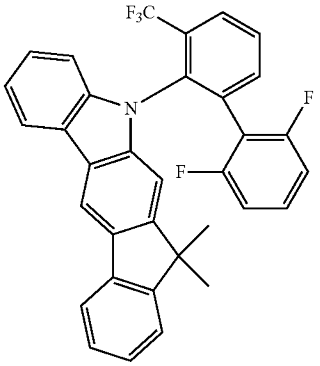
13
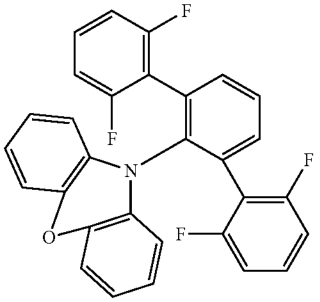
14
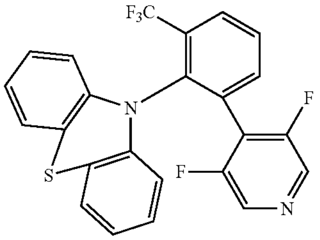
15
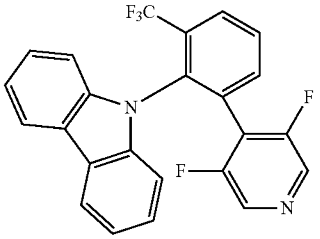
16
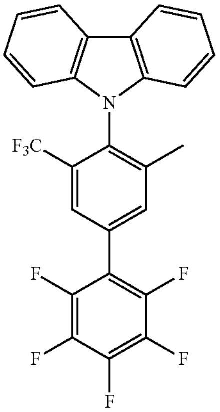

-continued
17
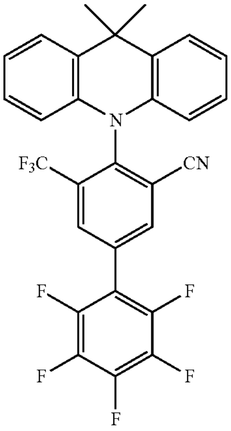
18
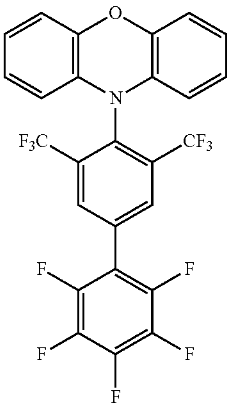
19
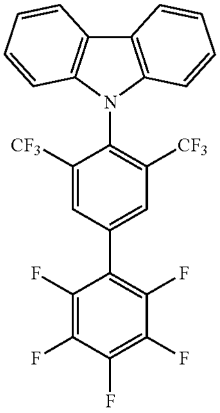
-continued
20
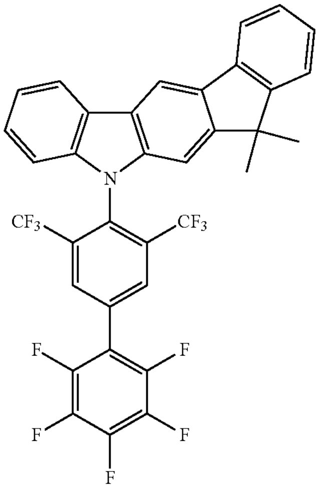
21
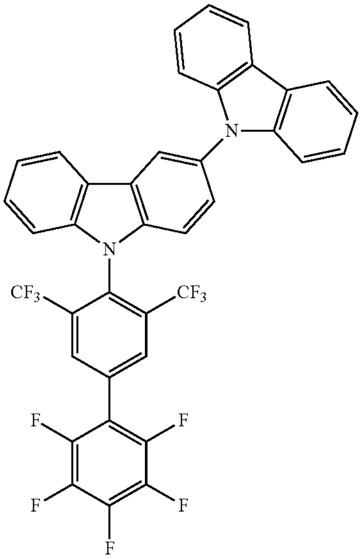
22
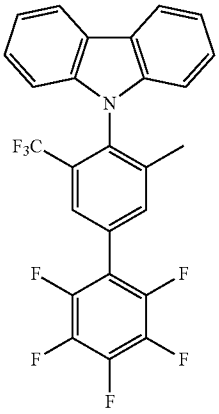

23
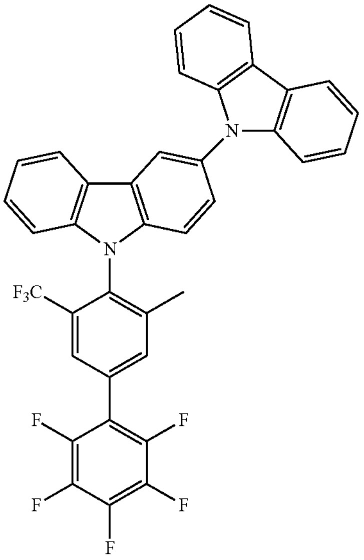
24
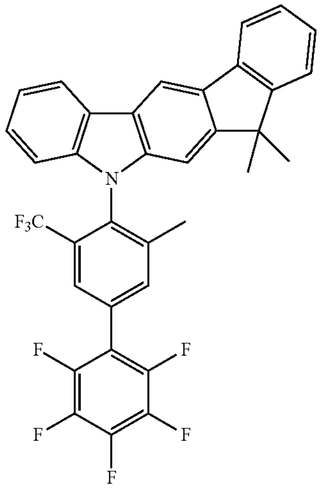
25
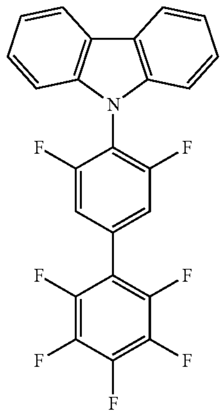
26
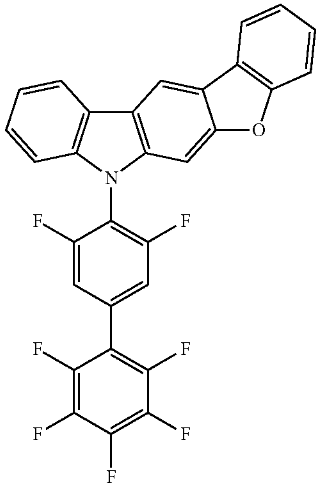
27
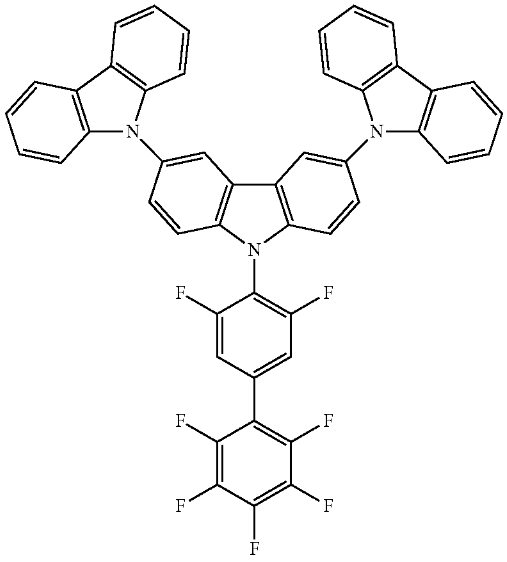

-continued
28
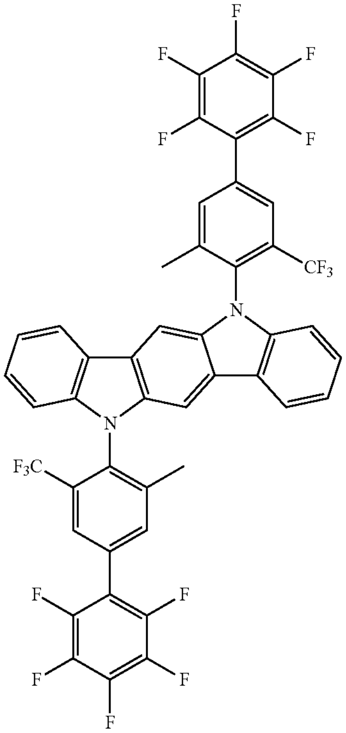
29
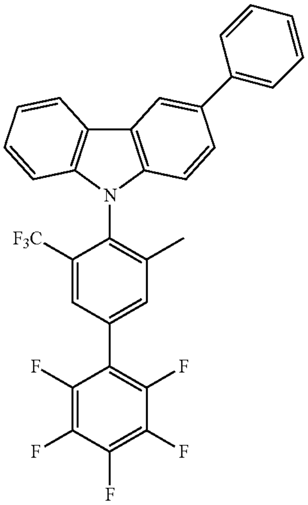
-continued
30
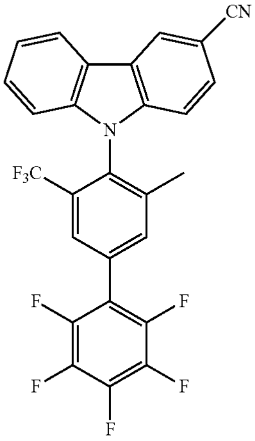
31
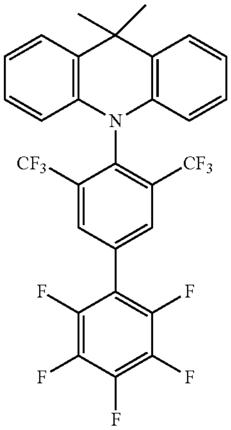
32
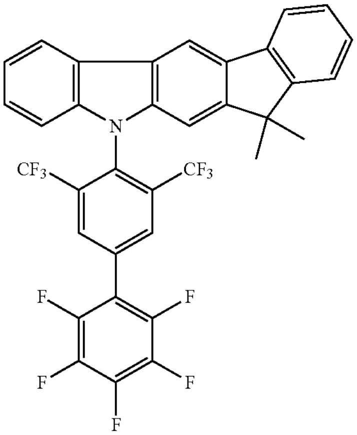

-continued
33
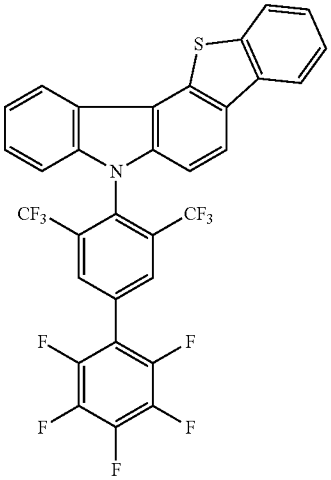
34
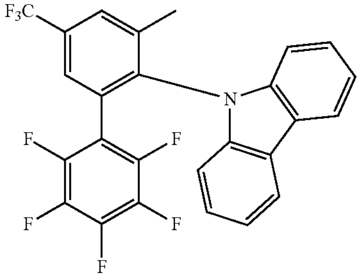
35
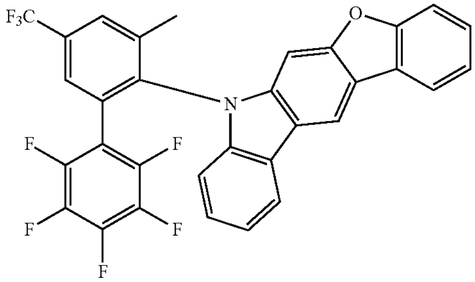
36
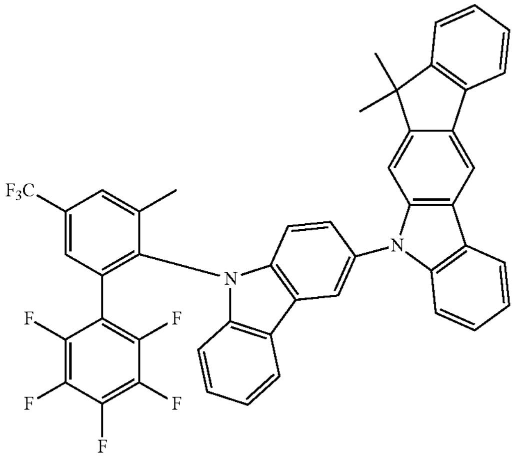
-continued
37
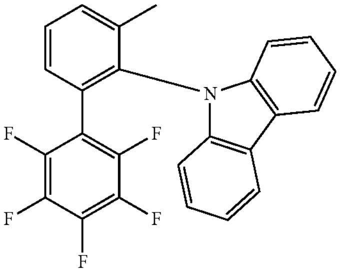
38
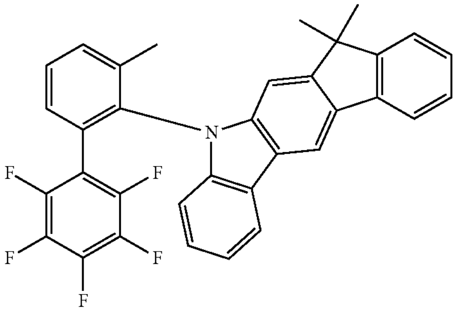
39
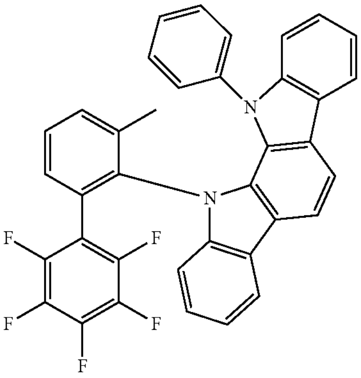
40
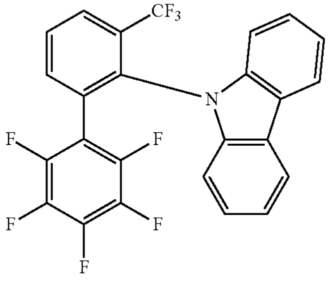
41
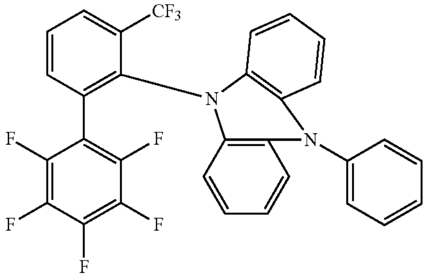

-continued
42
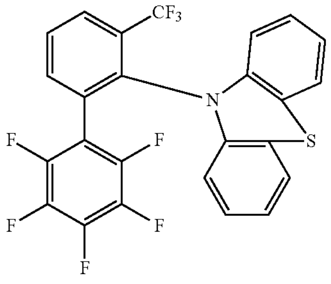
43
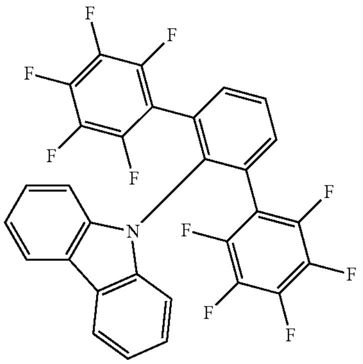
44
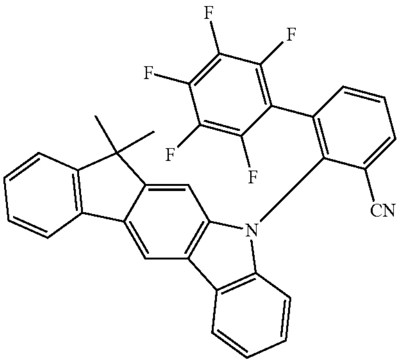
45
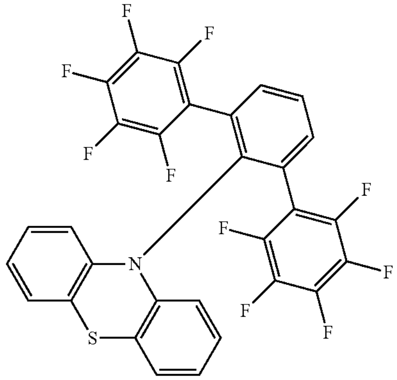
-continued
46
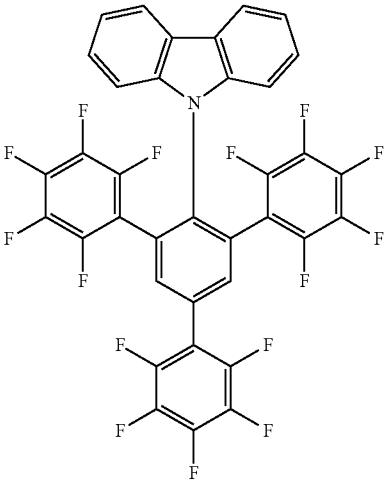
47
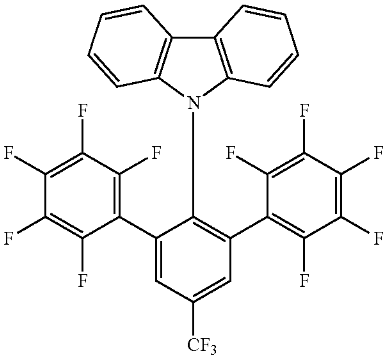
48
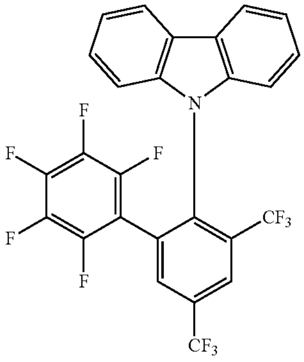
49
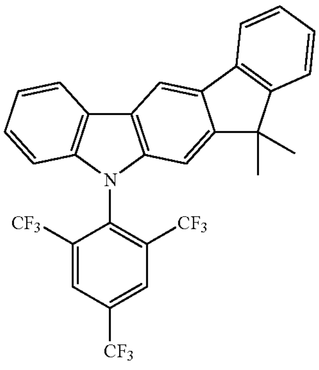

-continued
50
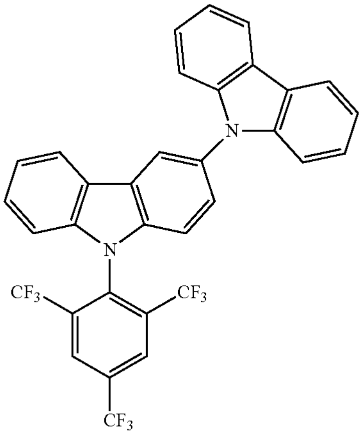
51
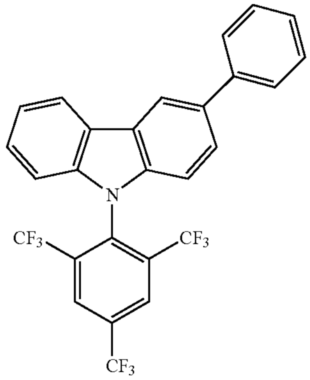
52
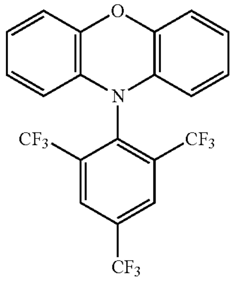
53
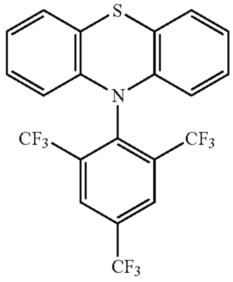
-continued
54
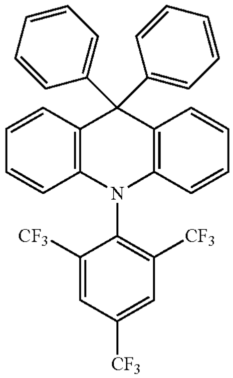
55
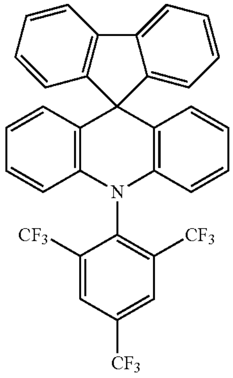
56
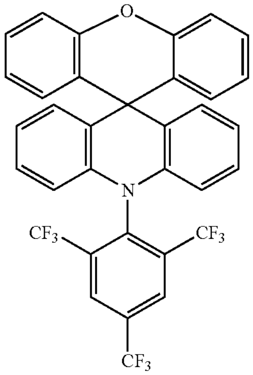
57
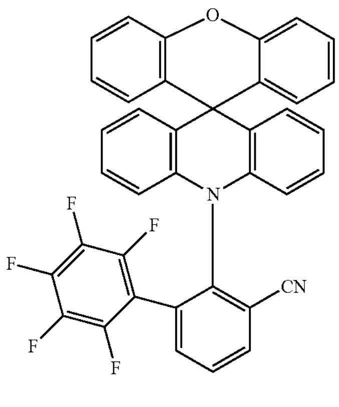

-continued
58
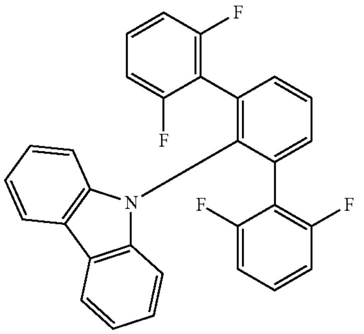
59
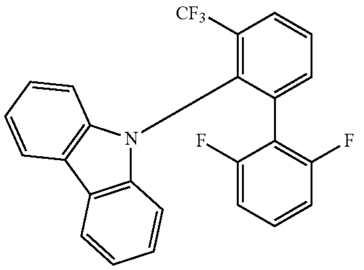
60
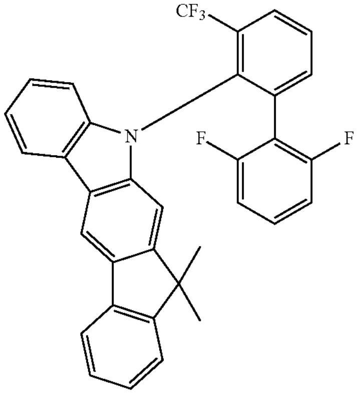
61
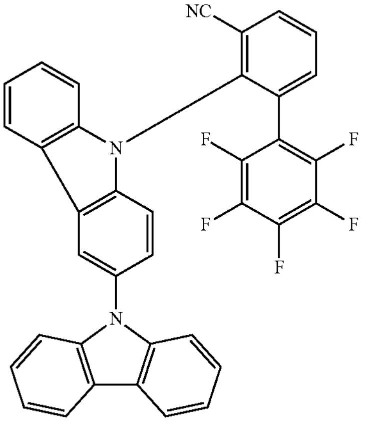
-continued
62
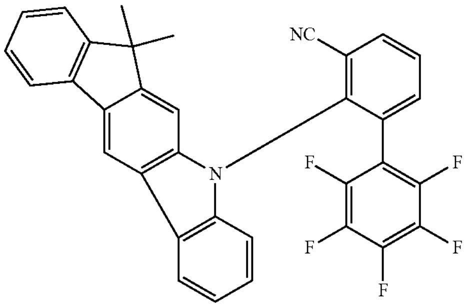
63
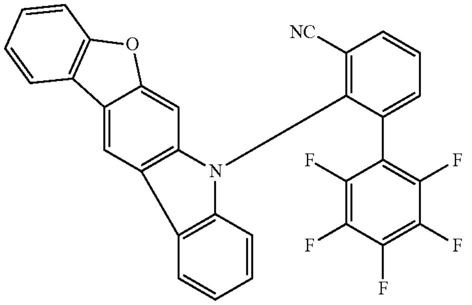
64
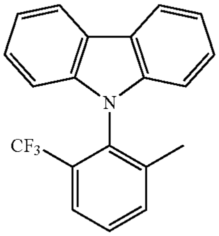
65
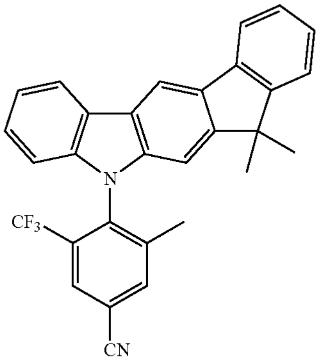
66
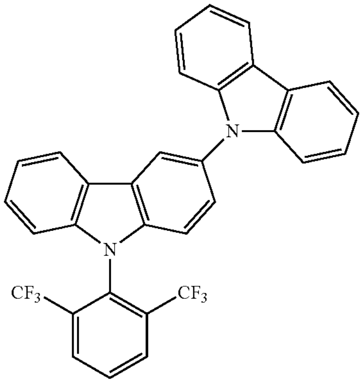

-continued
67
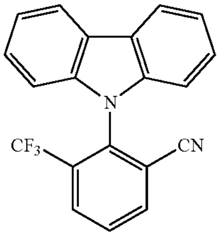
68
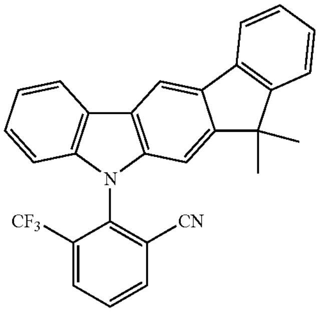
69
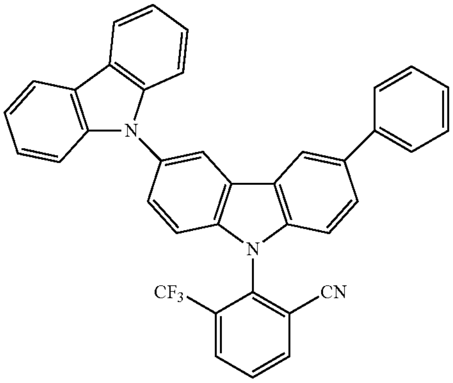
70
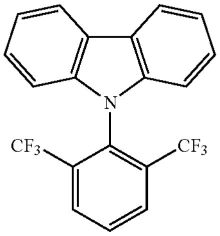
71
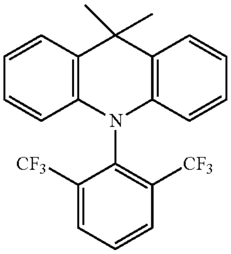
-continued
72
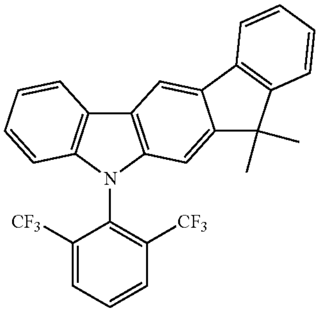
73
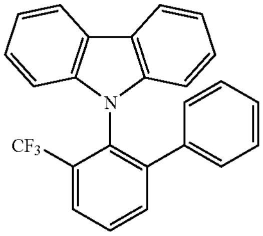
74
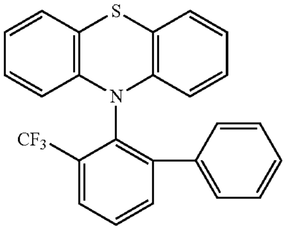
75
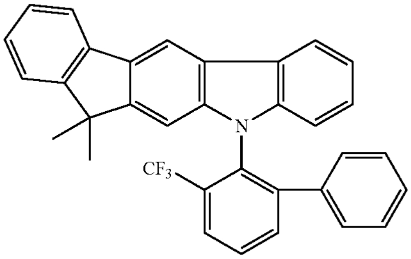
76
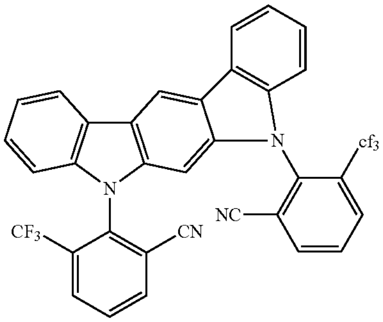

-continued
77
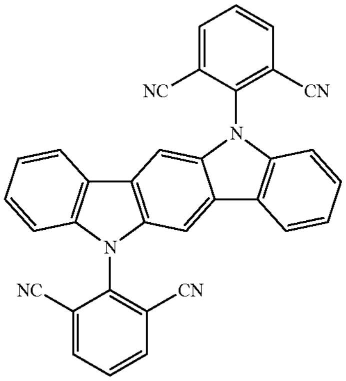
78
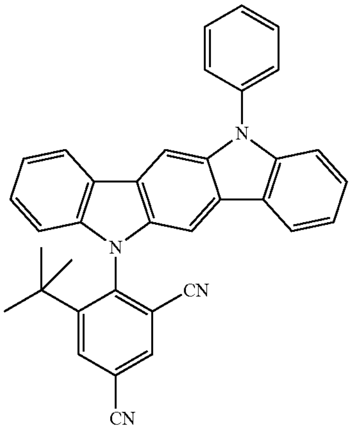
79
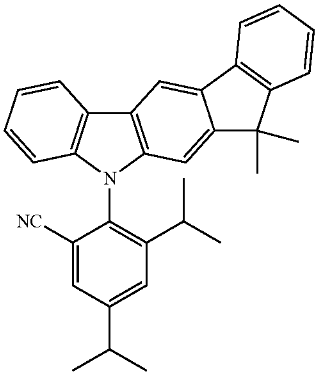
80
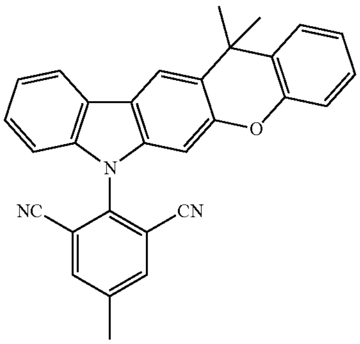
-continued
81
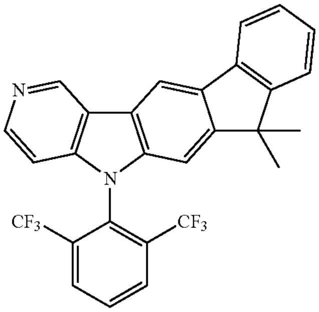
82
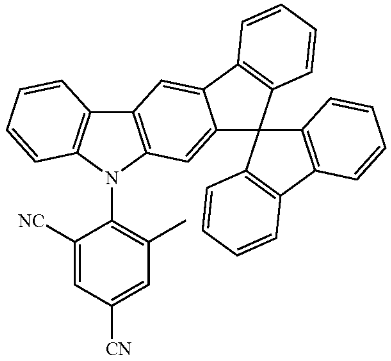
83
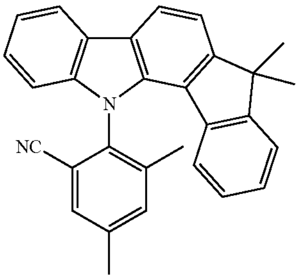
84
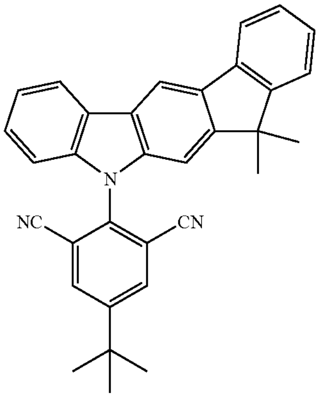

-continued
85
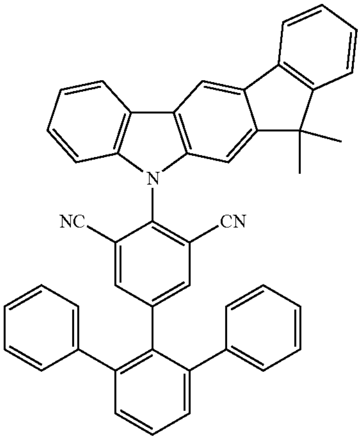
86
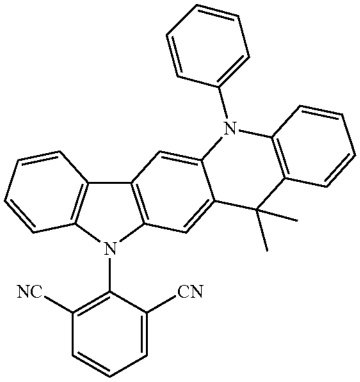
87
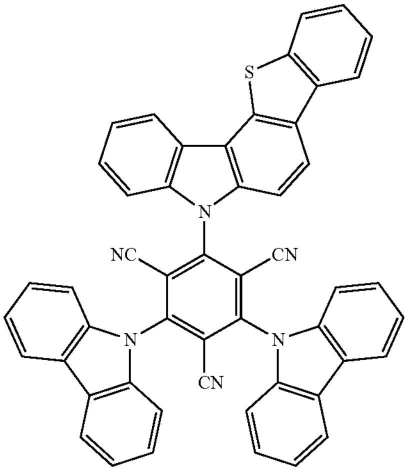
-continued
88
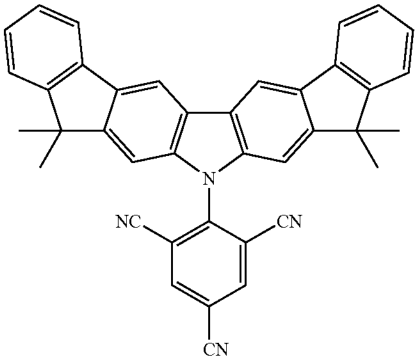
89
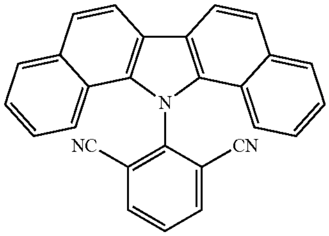
90
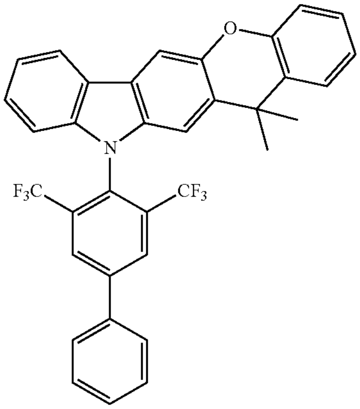
91
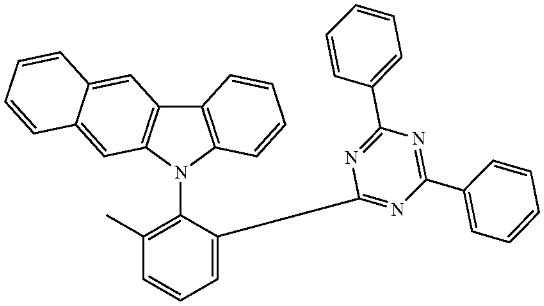

-continued
92
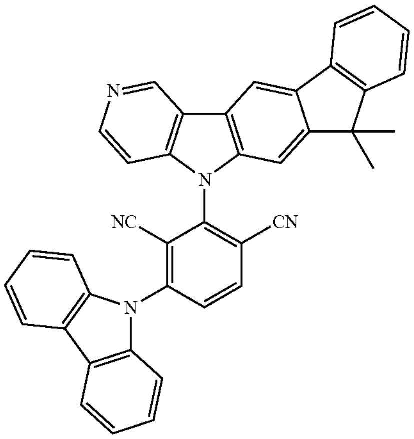
93
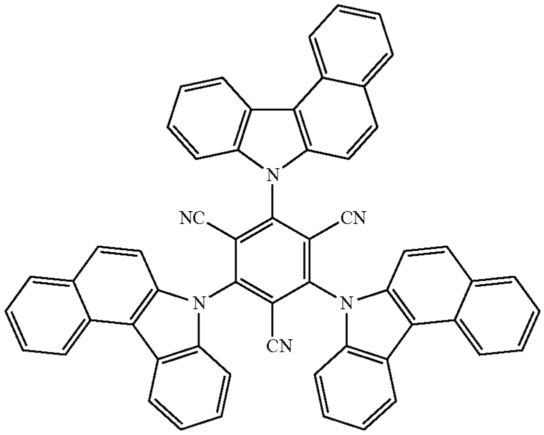
94
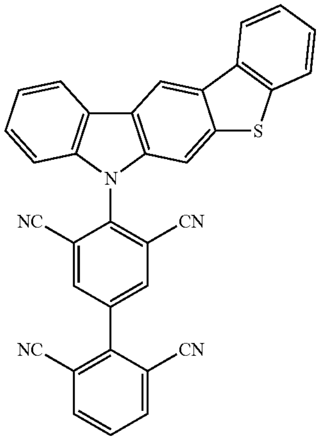
-continued
95
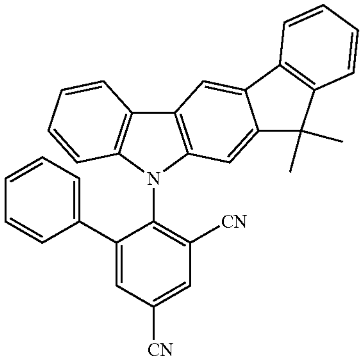
96
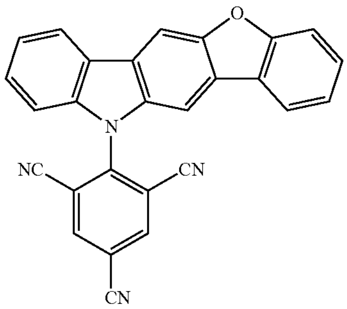
97
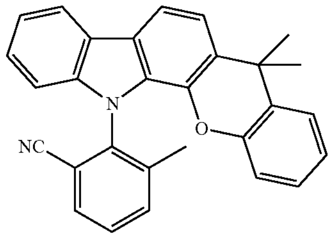
98
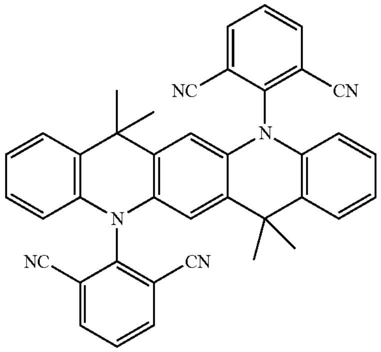
99
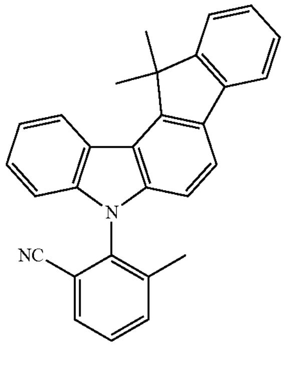

-continued
100
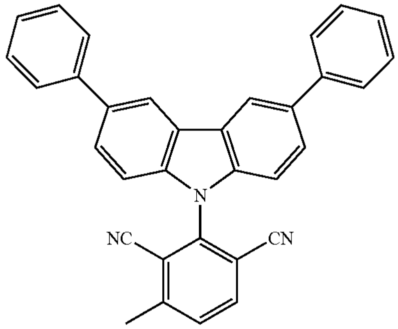
101
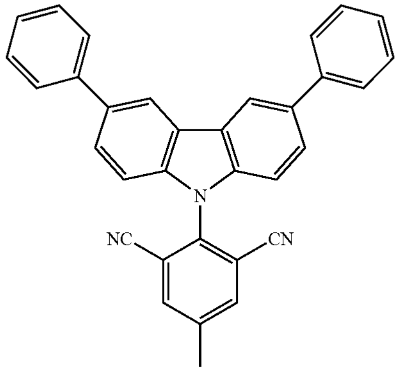
102
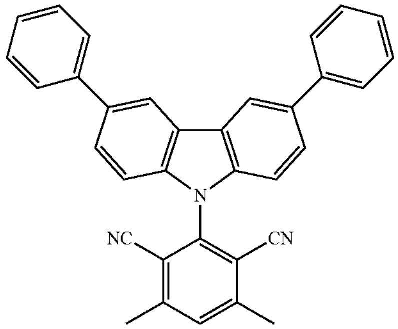
103
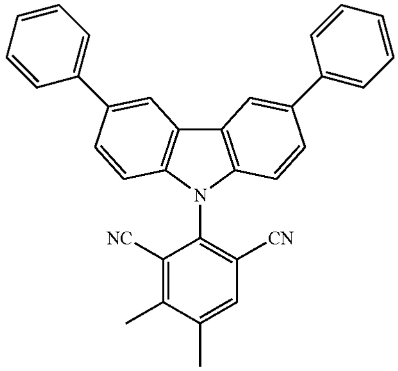
-continued
104
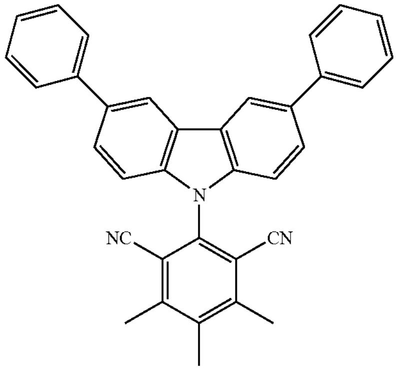
105
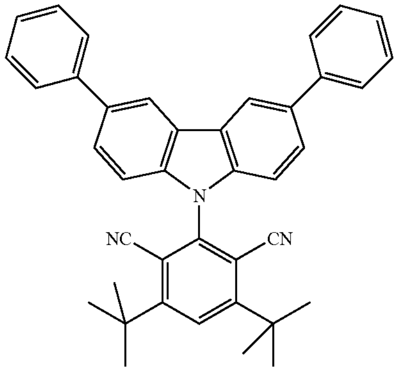
106
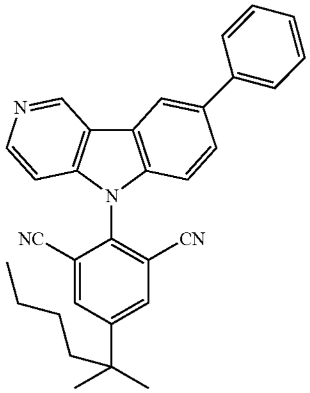
107
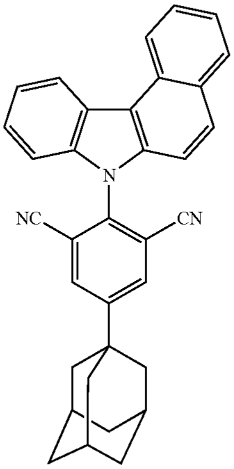

-continued
108
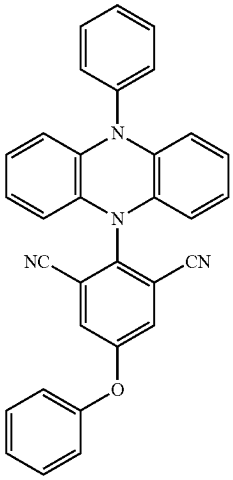
109
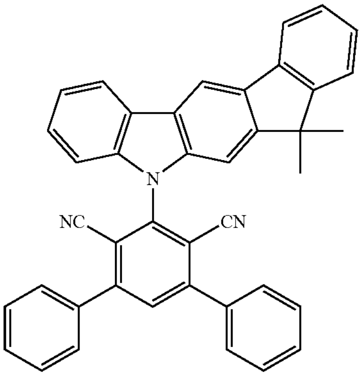
110
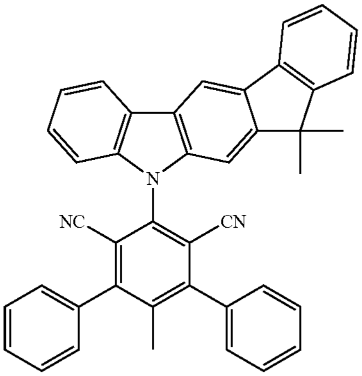
-continued
111
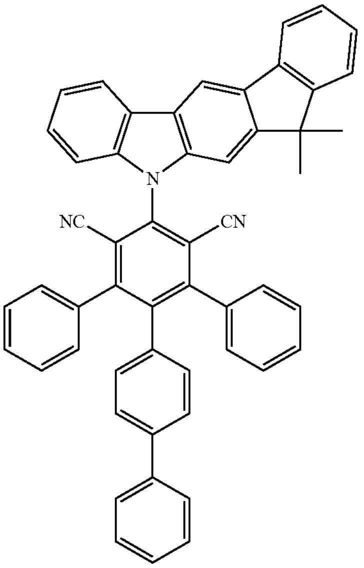
112
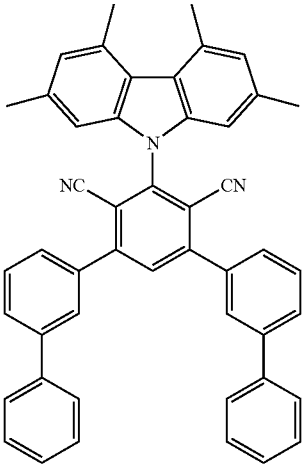
113
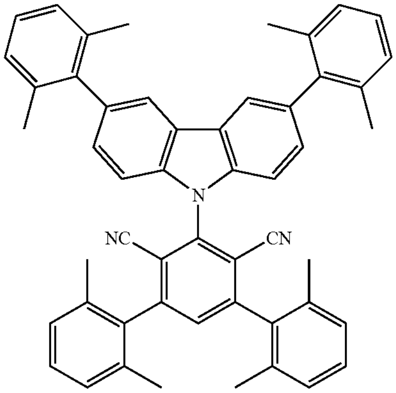

-continued
114
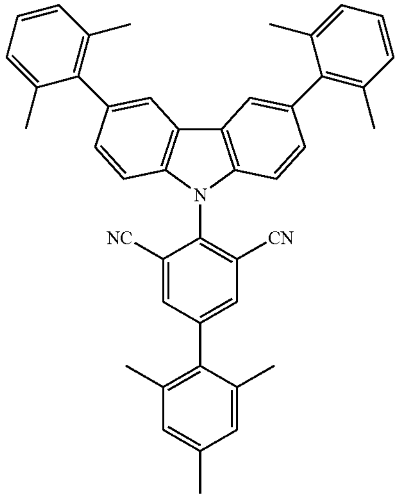
115
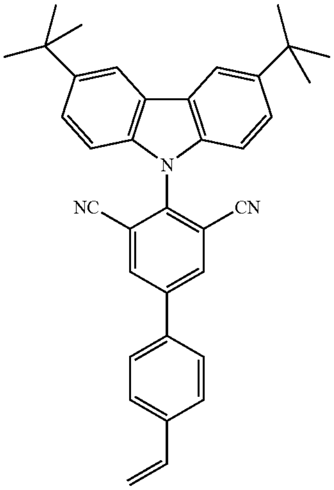
116
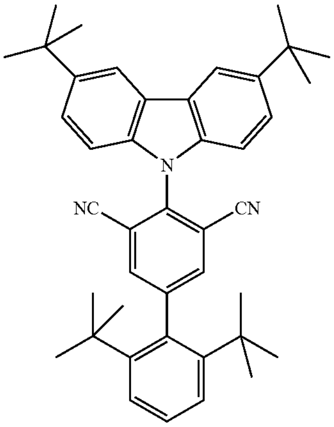
-continued
117
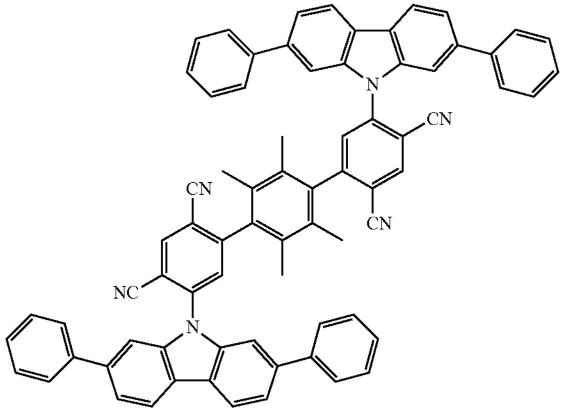
118
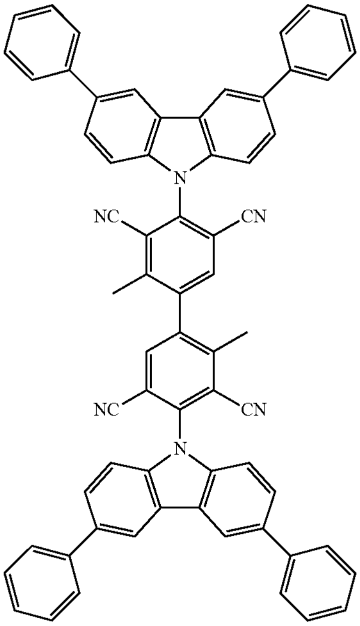

-continued
119
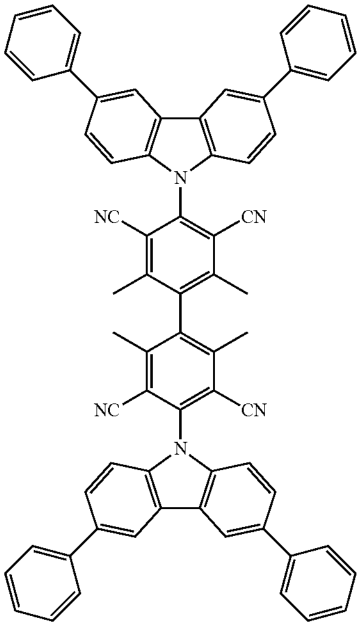
120
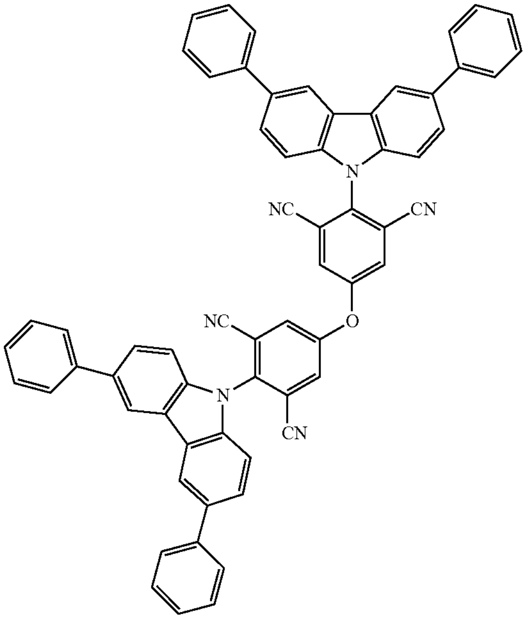
-continued
121
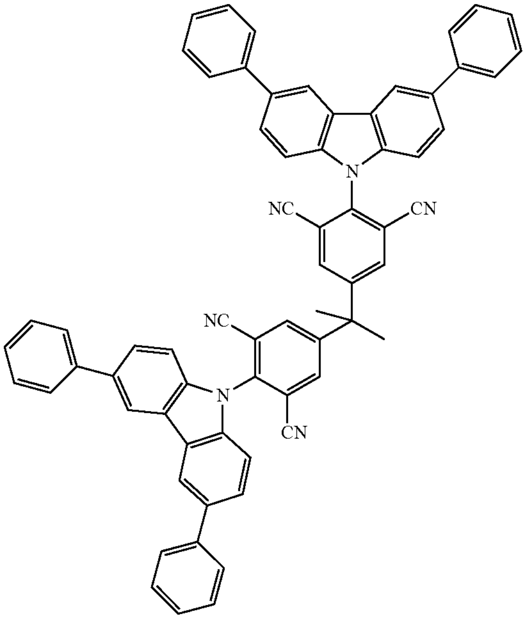
122
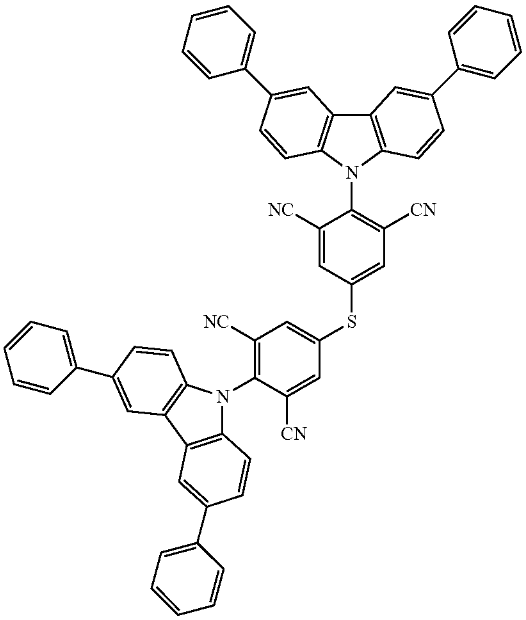

-continued
123
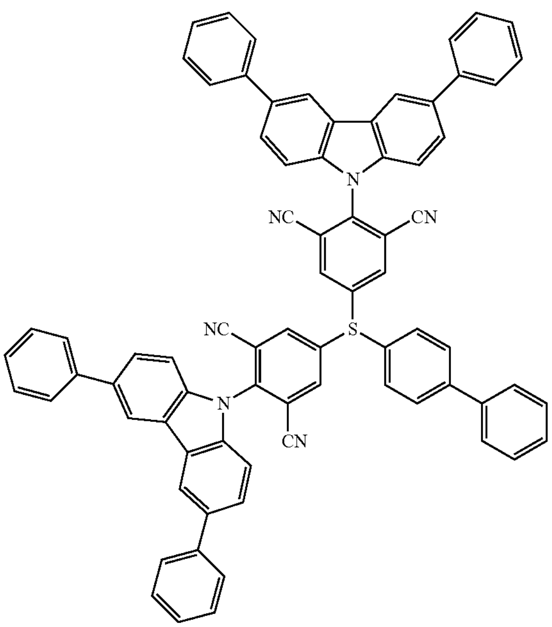
124
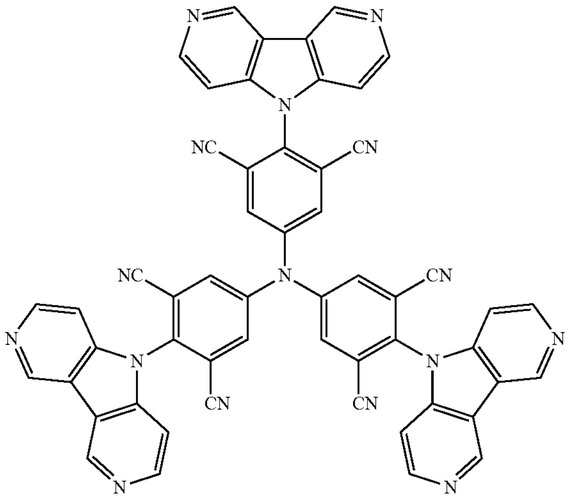
125
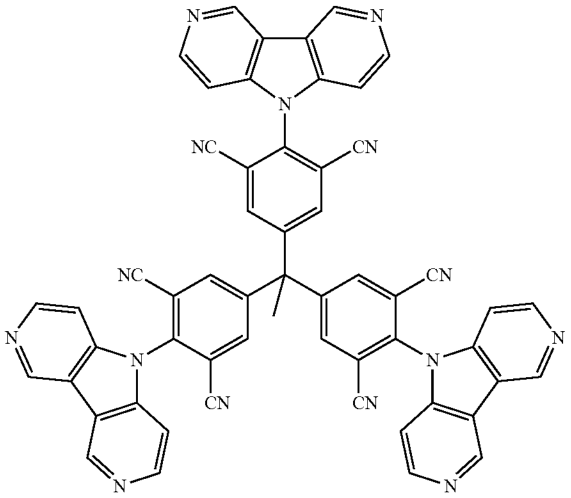
-continued
126
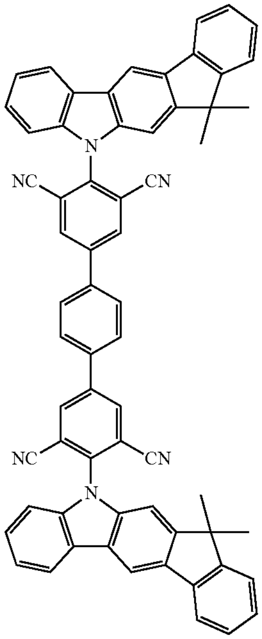
127
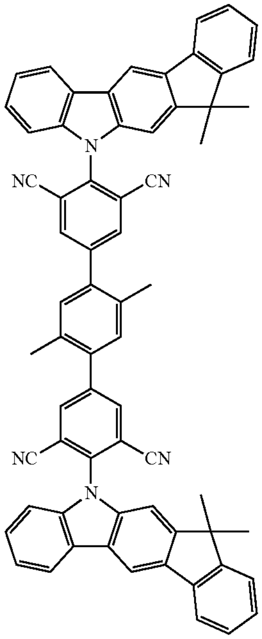

-continued
128
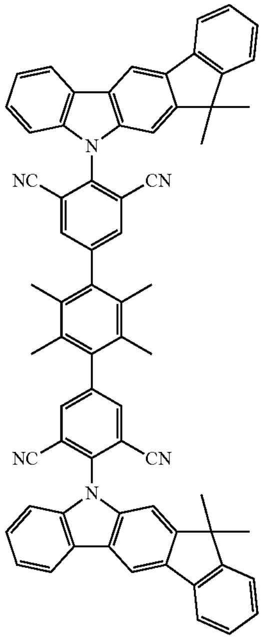
129
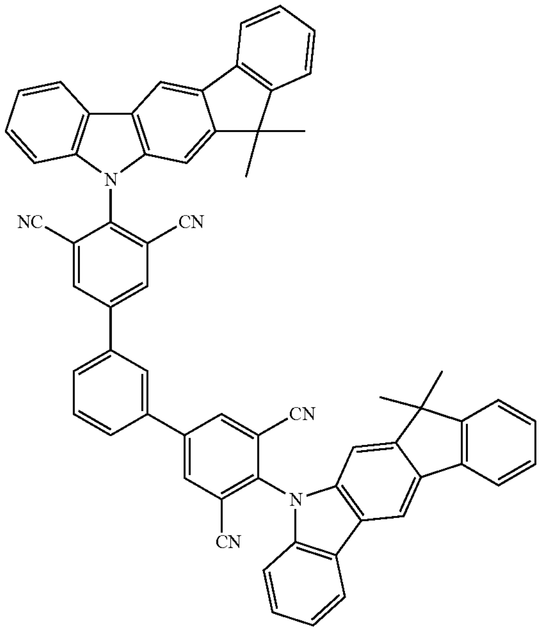
-continued
130
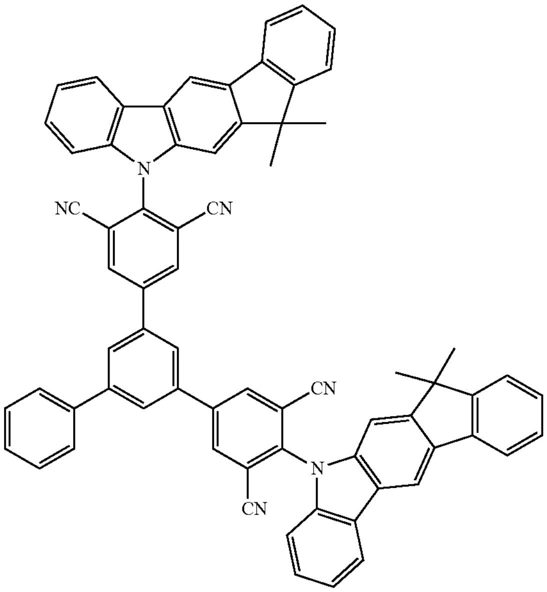
131
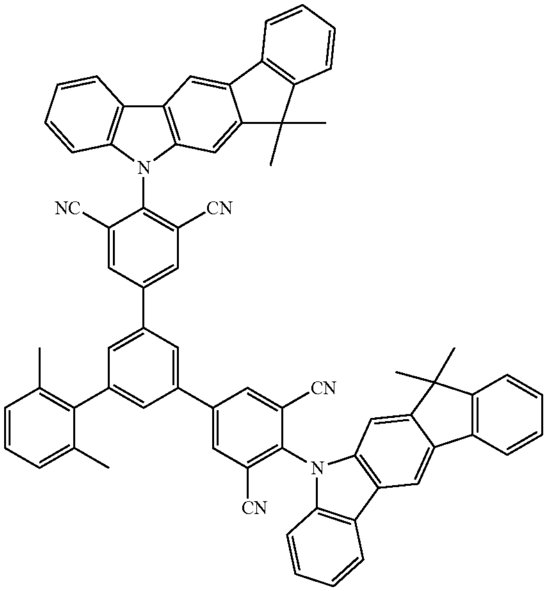

-continued
132
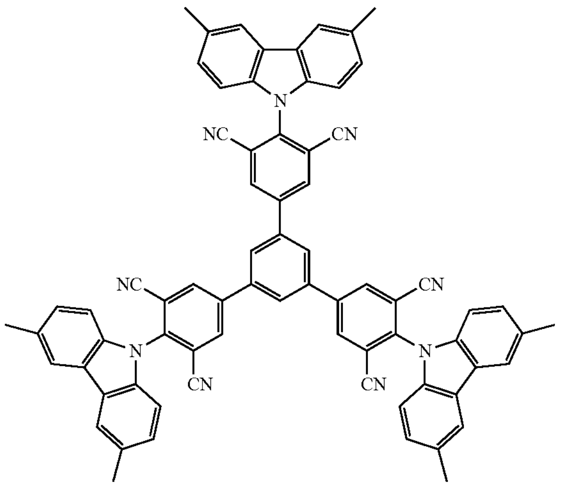
133
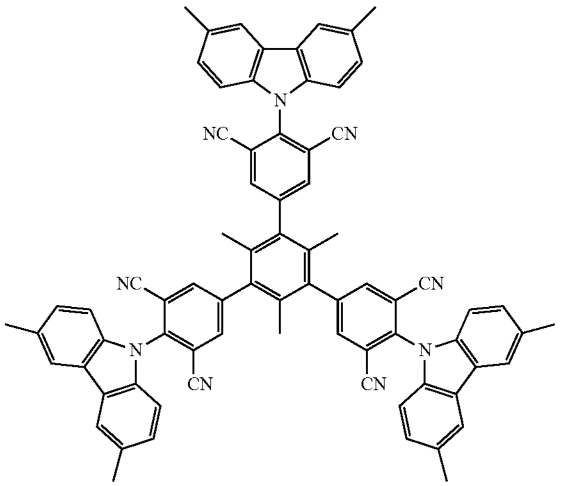
134
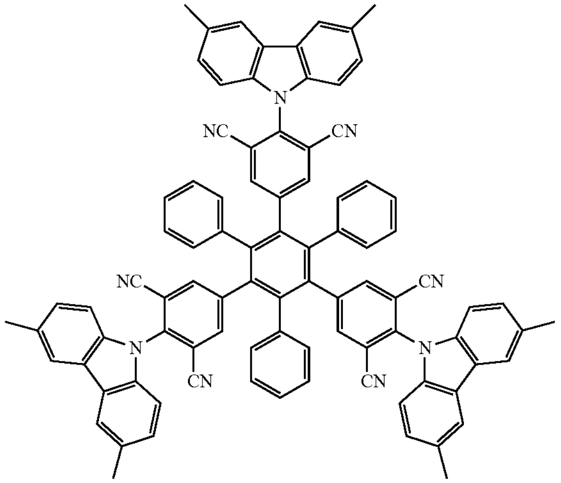
-continued
135
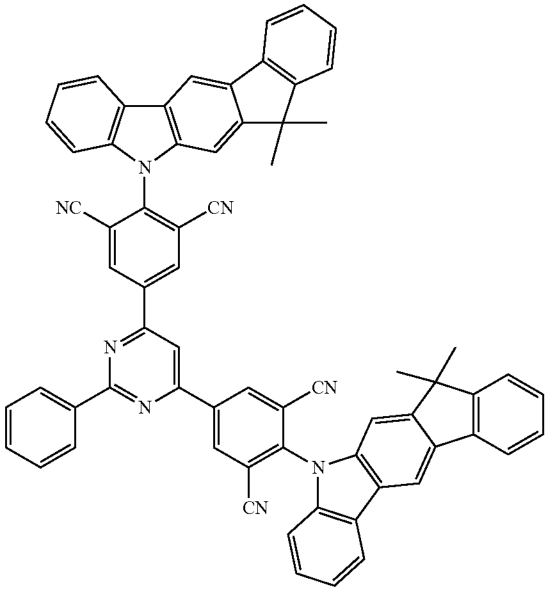
136
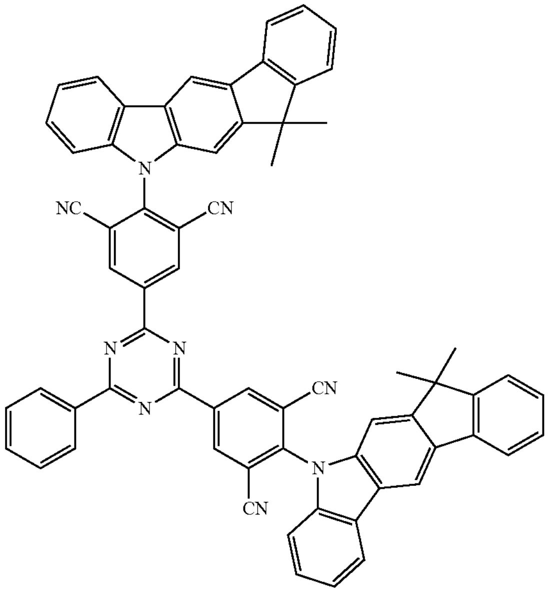

-continued
137
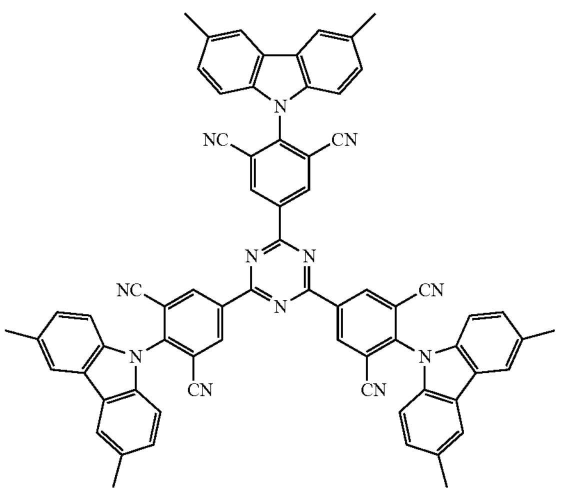
138
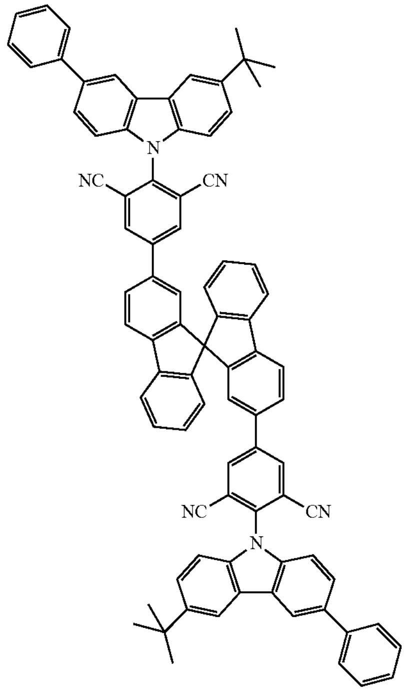
140
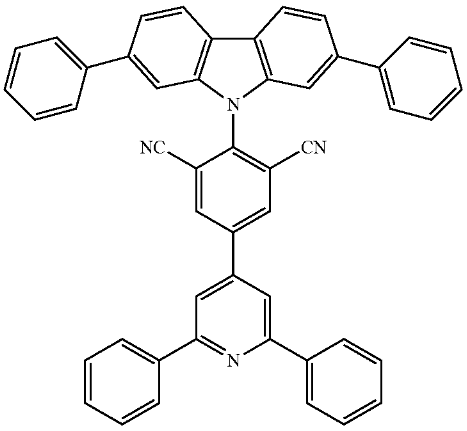
-continued
141
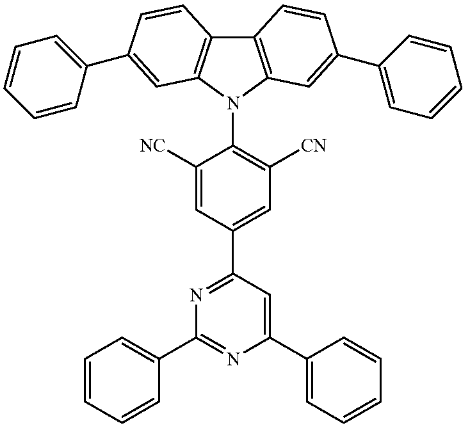
142
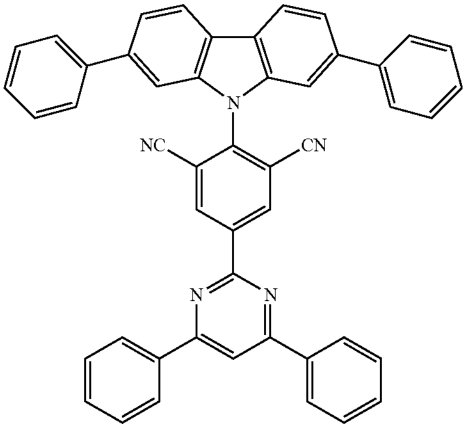
143
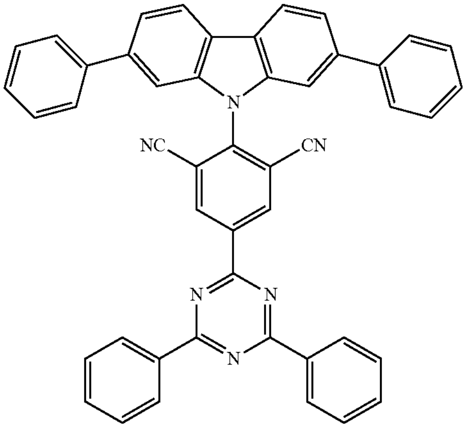

-continued
144
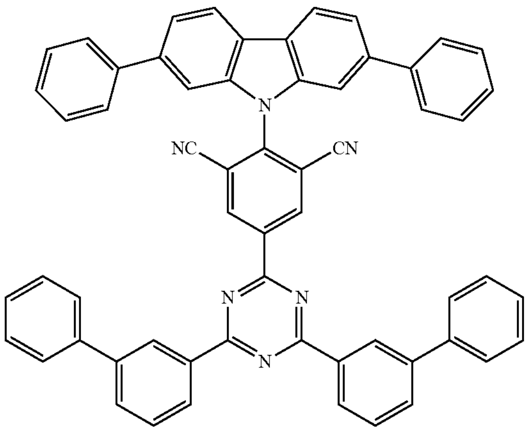
145
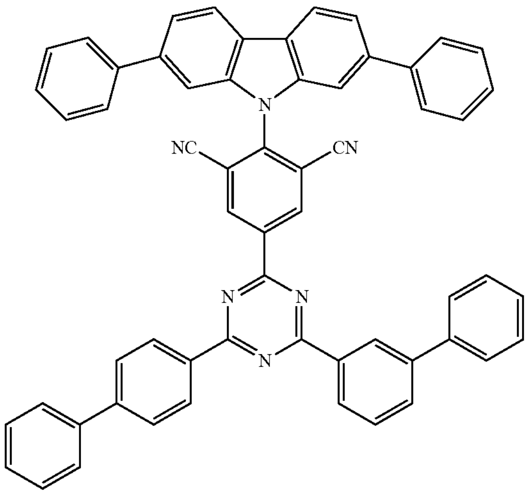
146
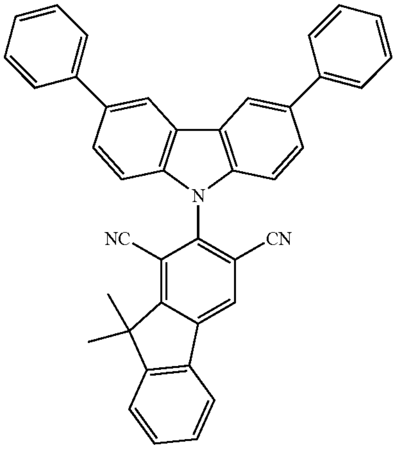
-continued
147
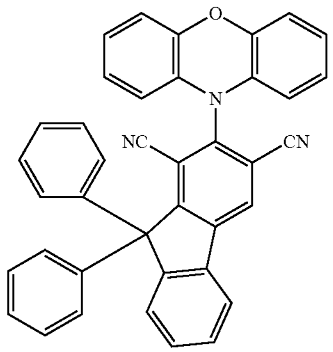
148
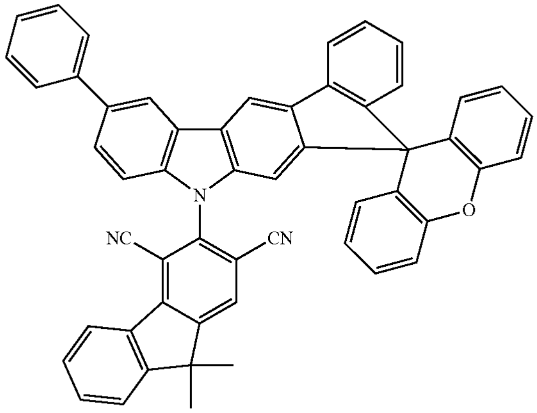
149
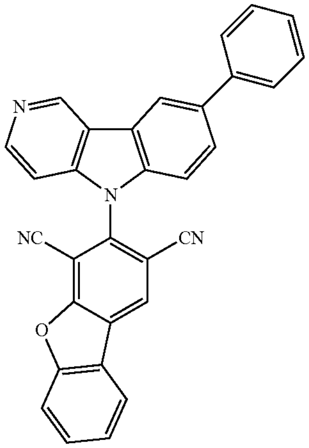

-continued
150
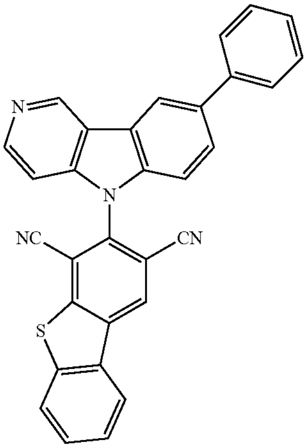
151
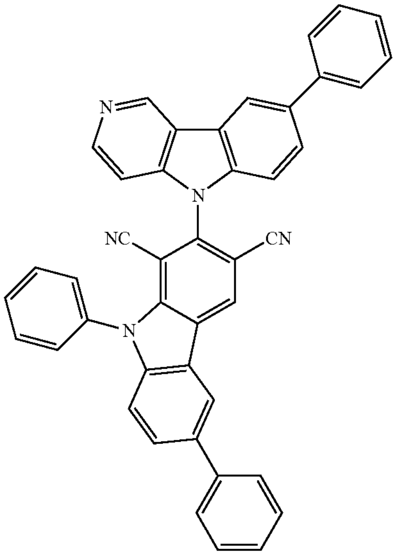
152
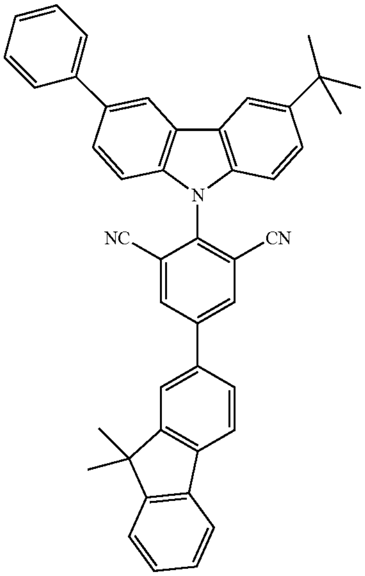
-continued
153
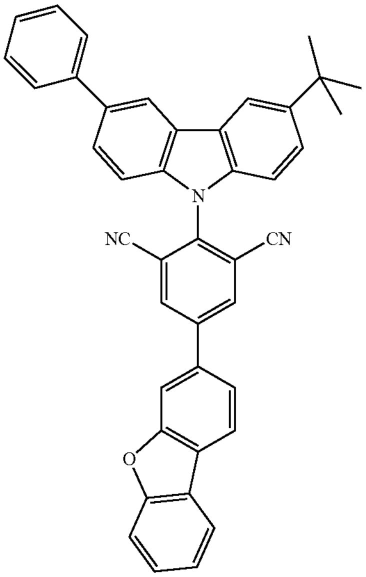
154
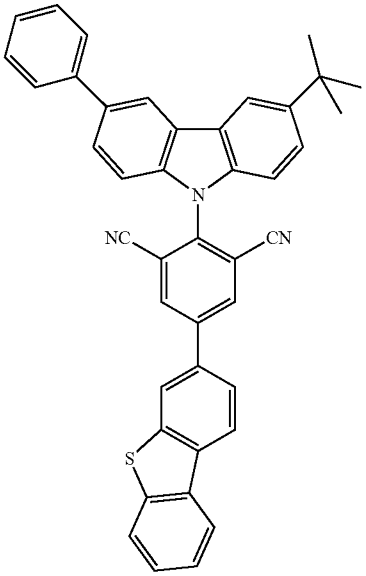

-continued
155
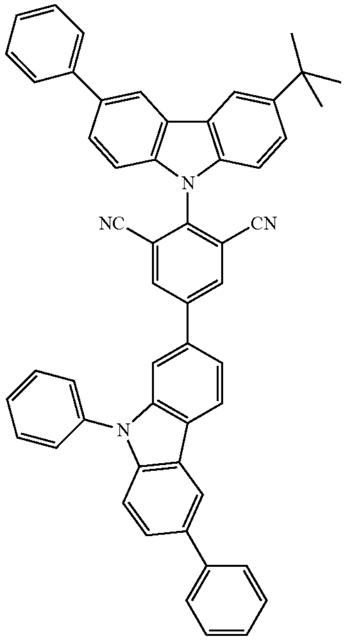
156
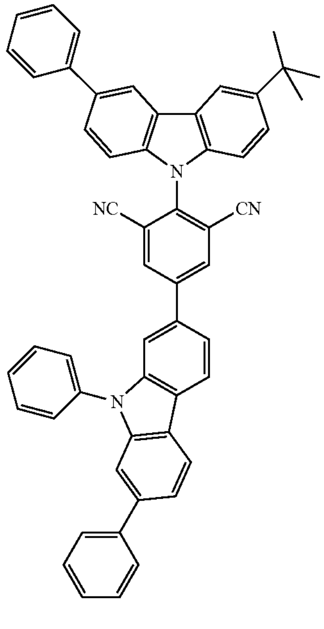
-continued
157
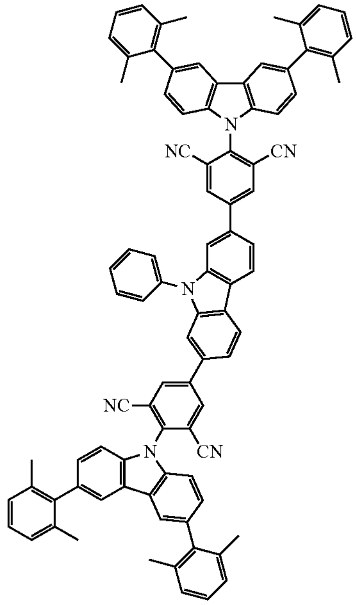
158
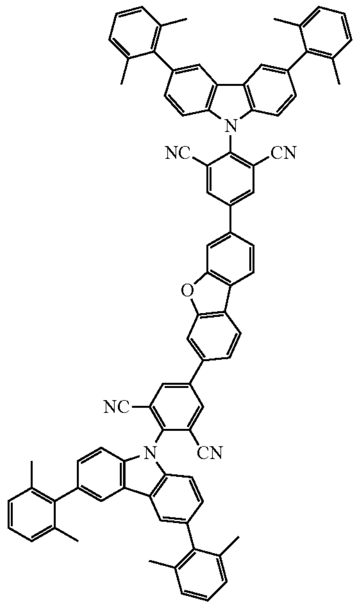

-continued
159
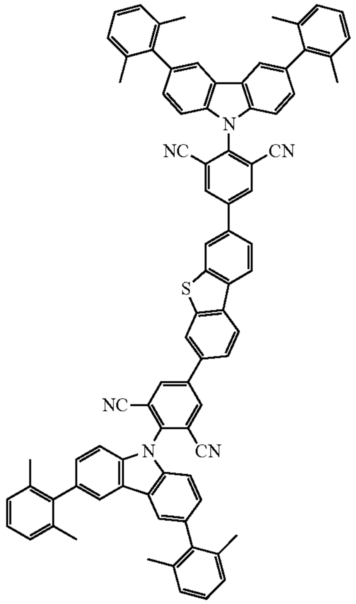
160
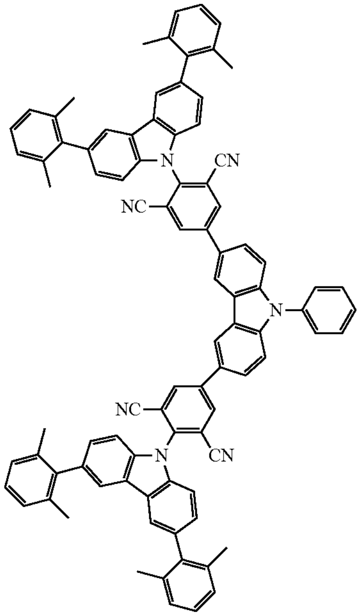
-continued
161
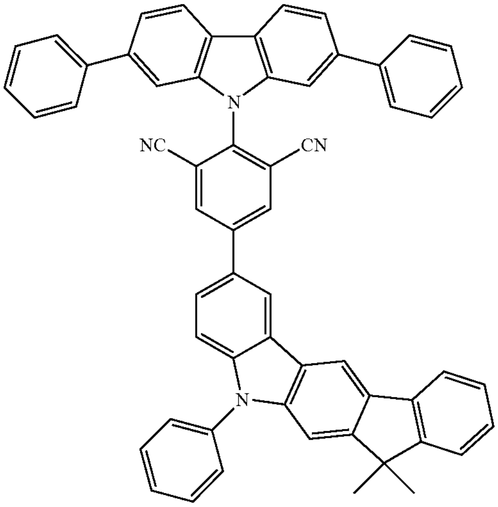
162
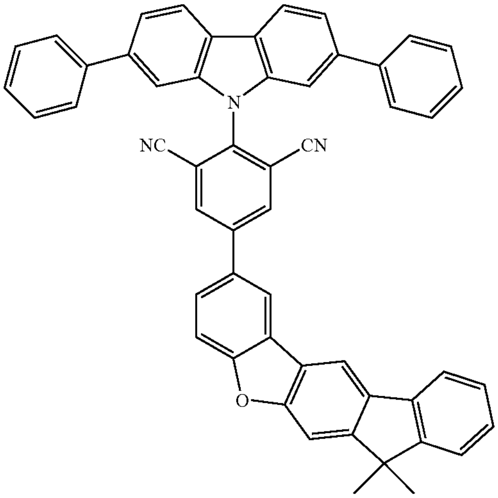
163
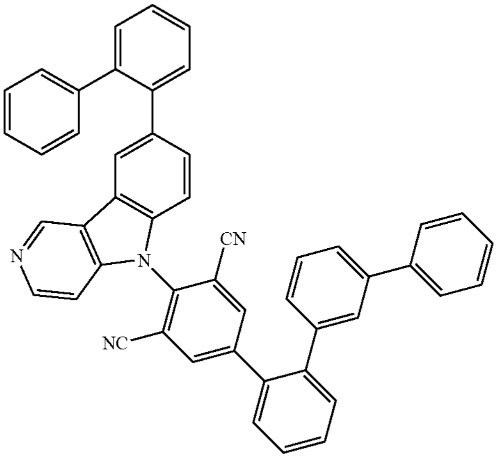

-continued
164
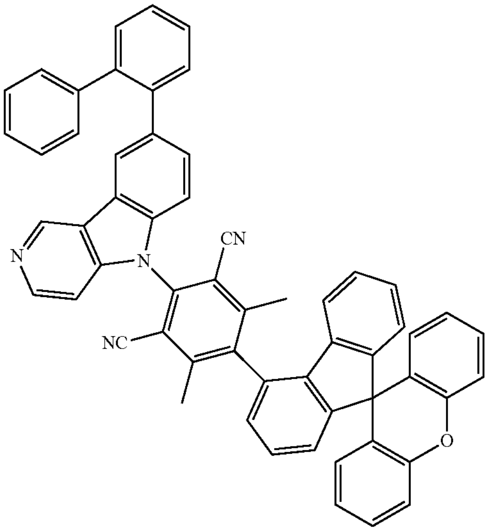
165
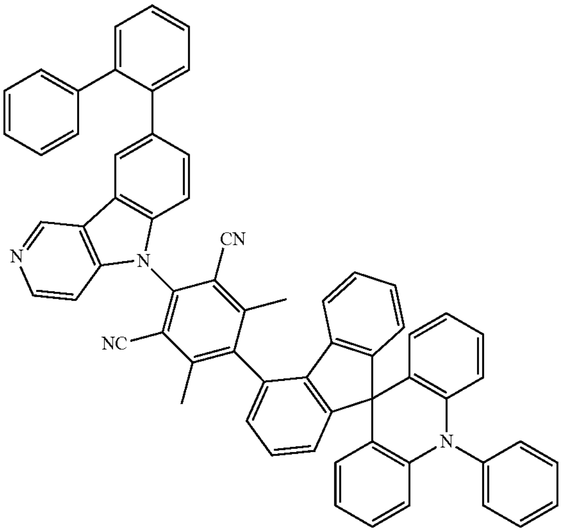
166
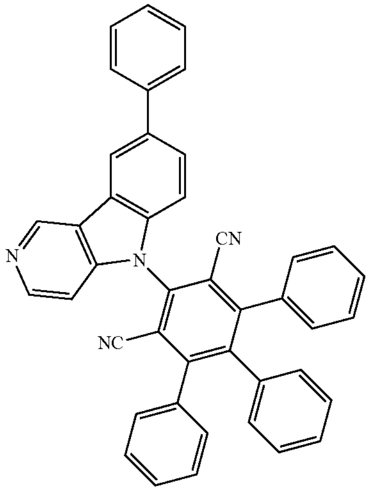
-continued
167
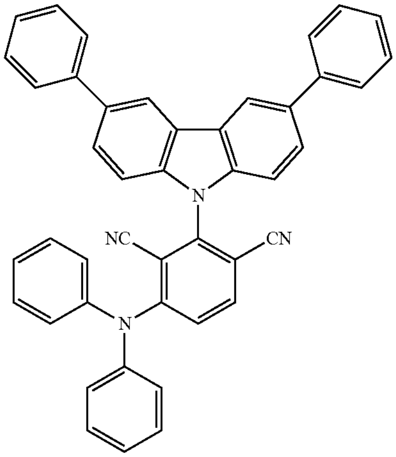
168
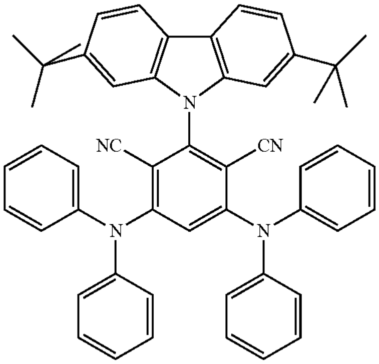
169
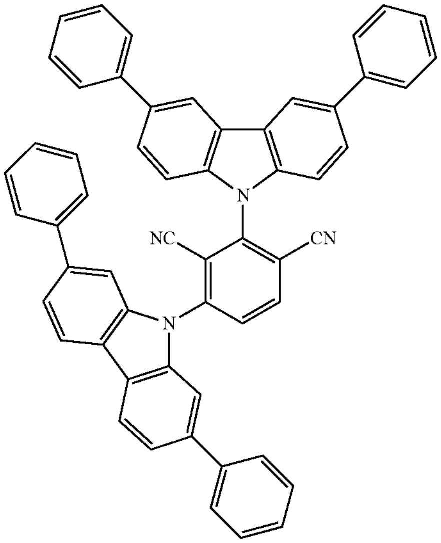

-continued
170
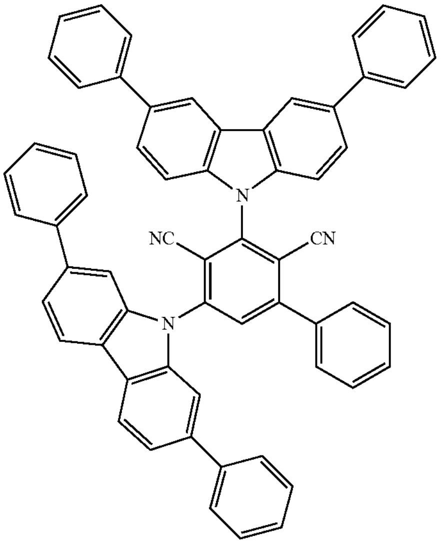
171
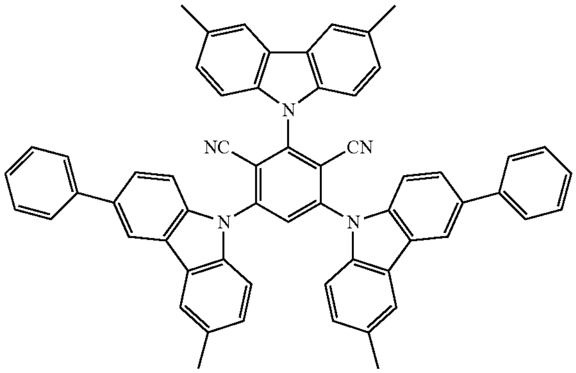
172
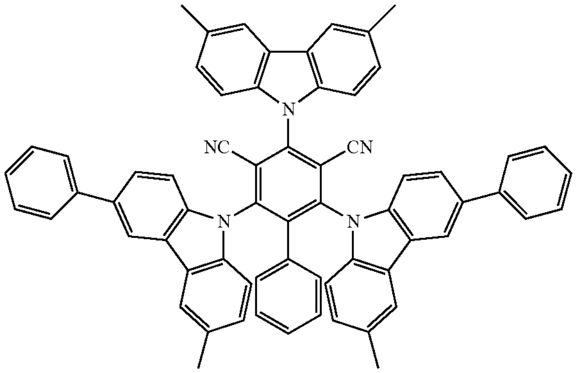
-continued
173
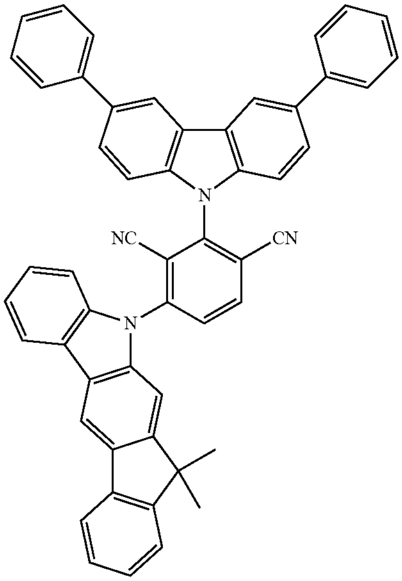
174
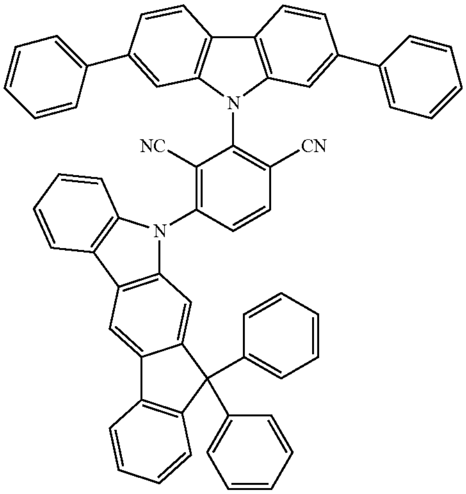
175
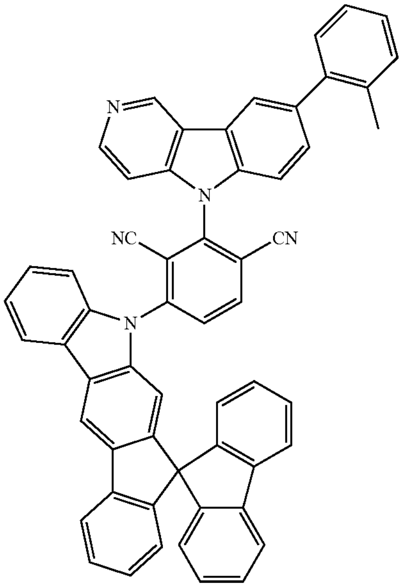

176
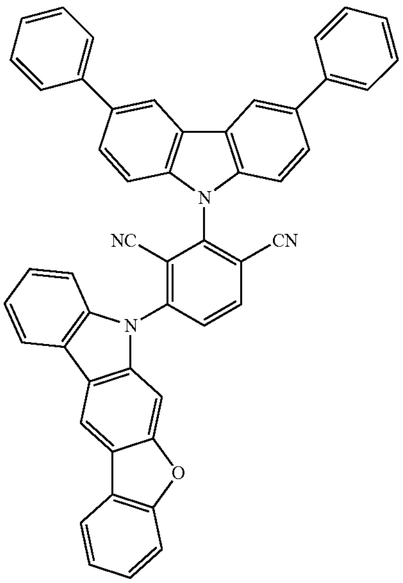
177
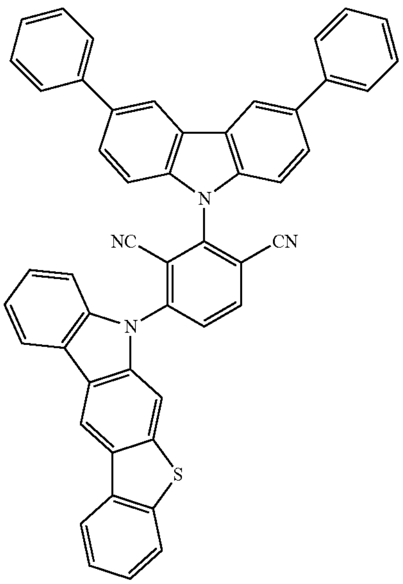
178
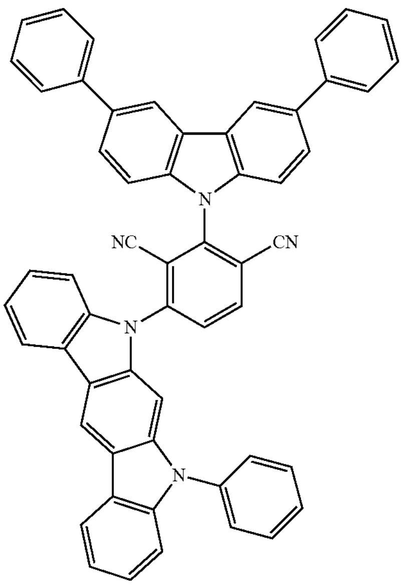
179
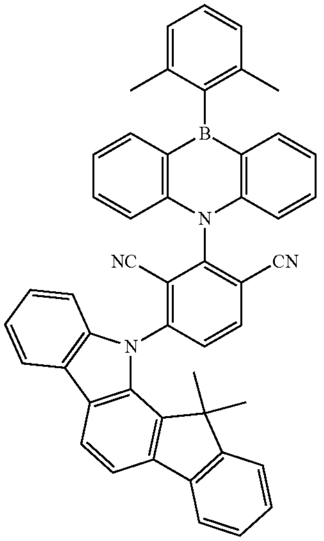
180
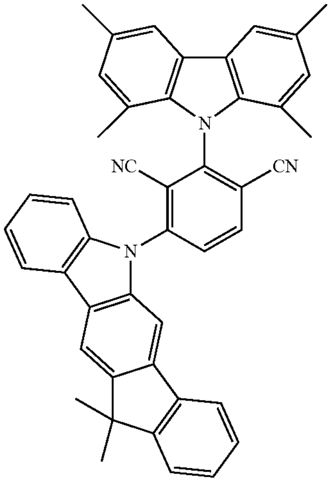

-continued
181
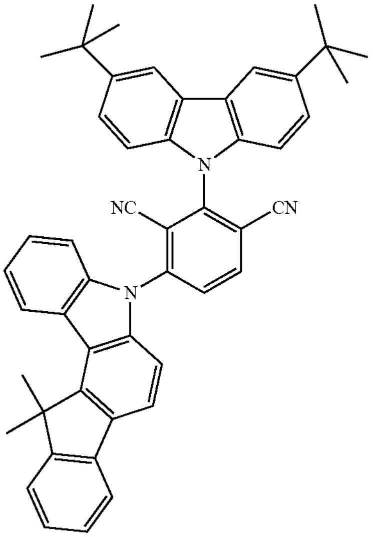
182
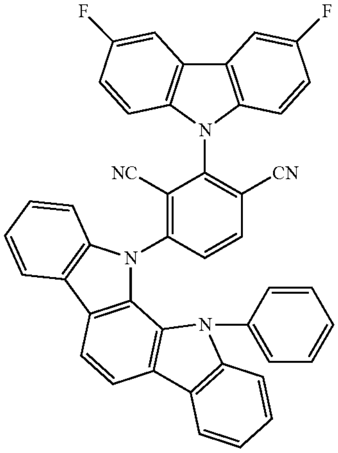
183
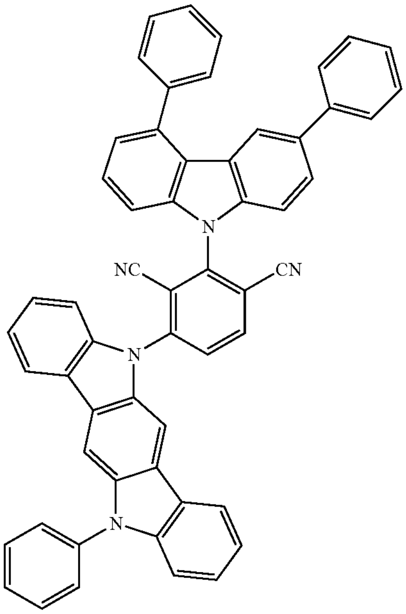
-continued
184
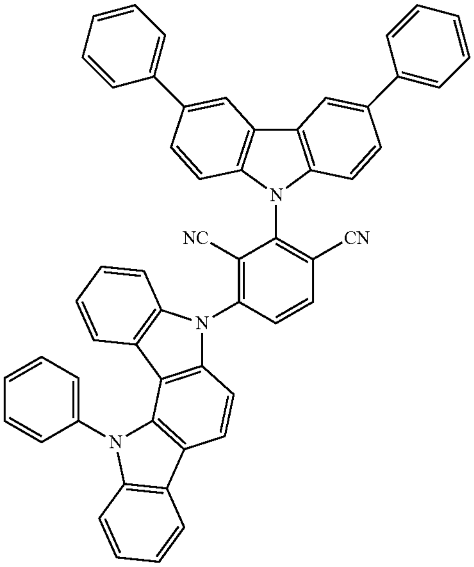
185
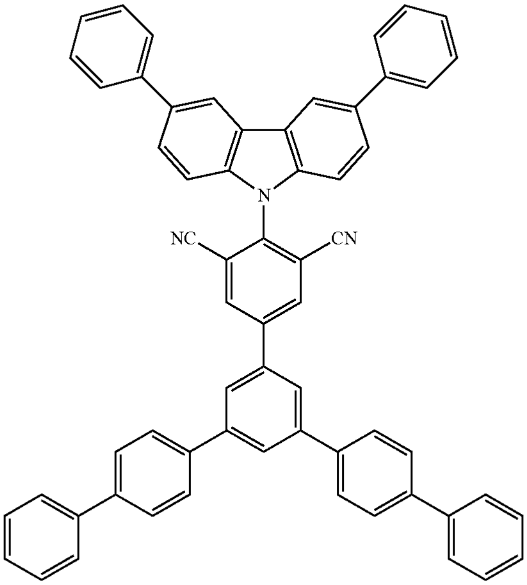
186
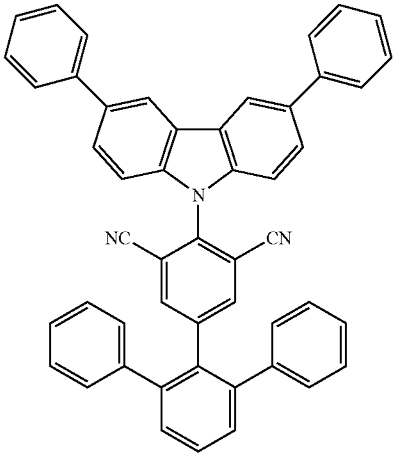

-continued
187
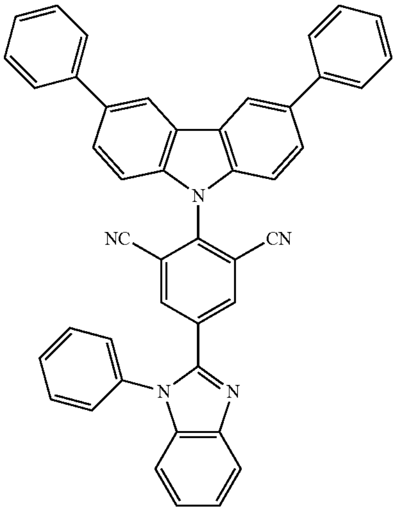
188
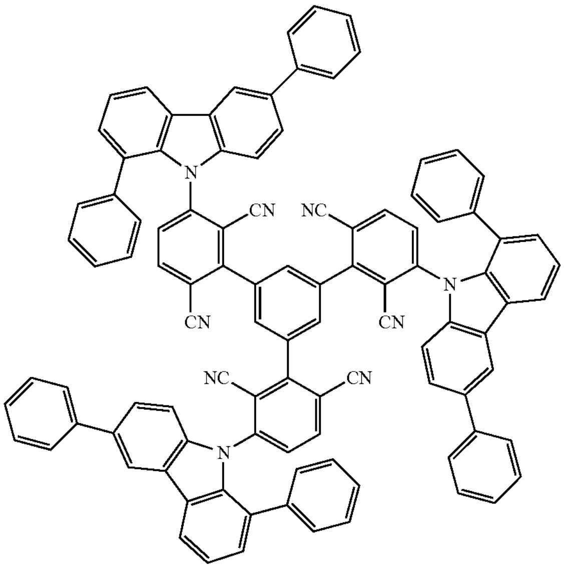
189
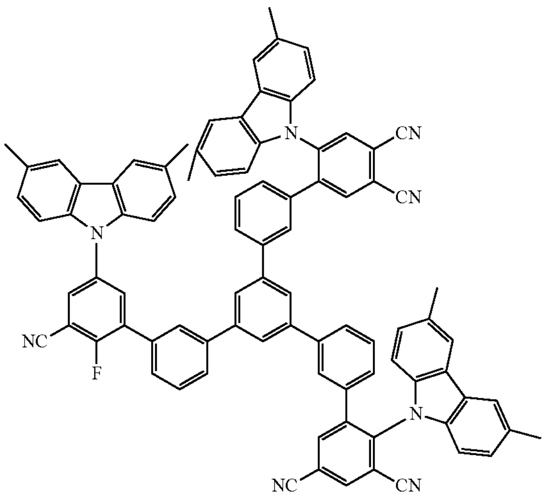
-continued
190
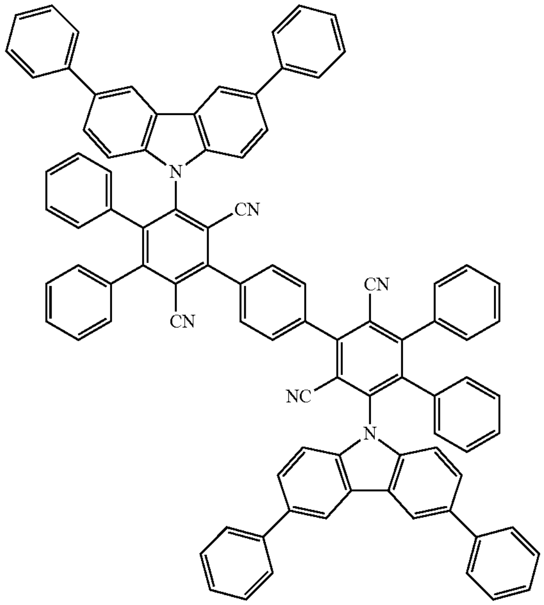
191
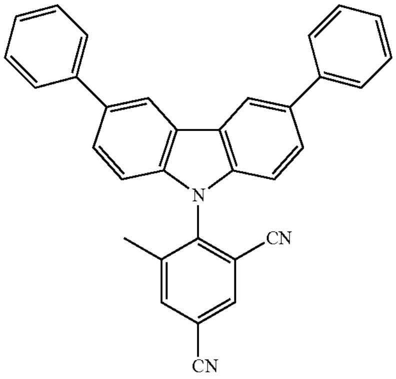
192
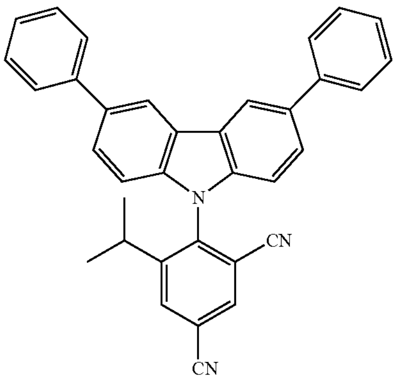

193
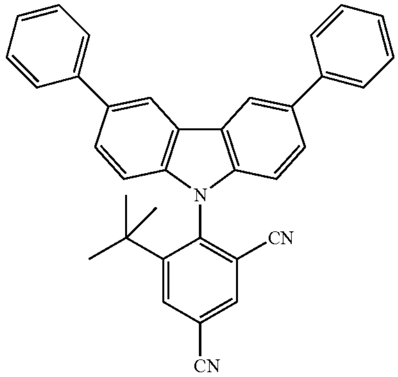
194
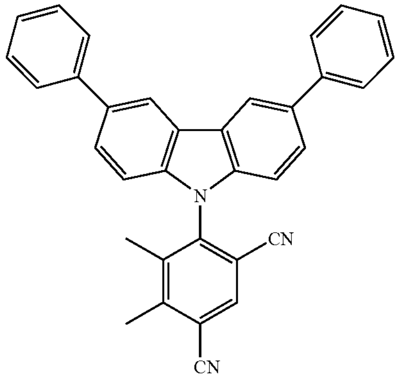
195
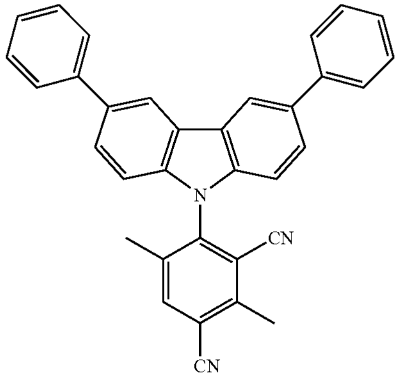
196
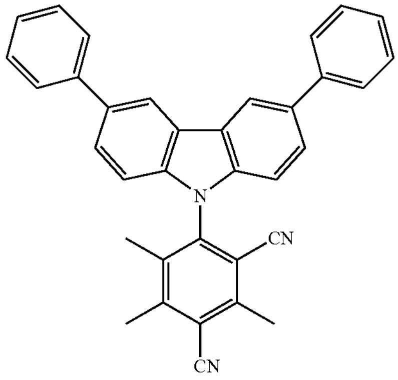
197
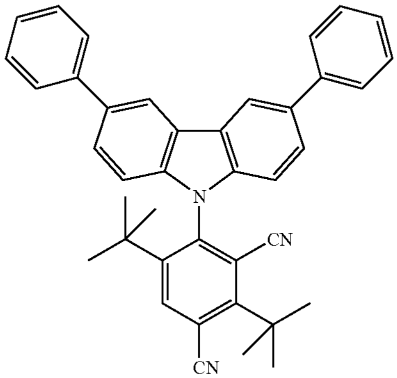
198
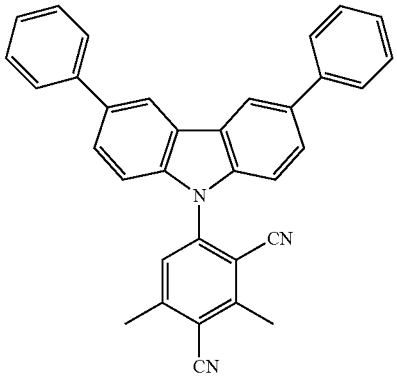
199
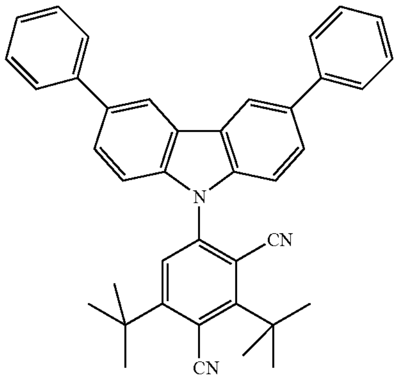
200
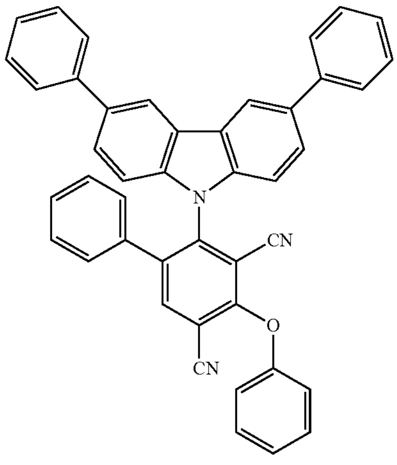

201
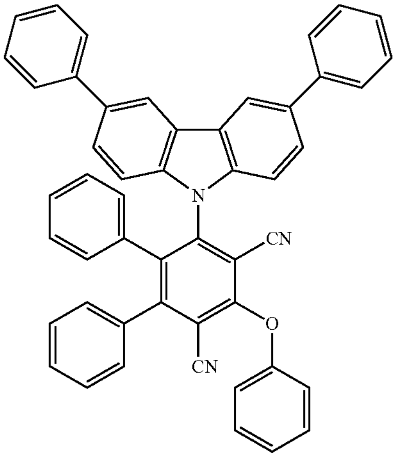
202
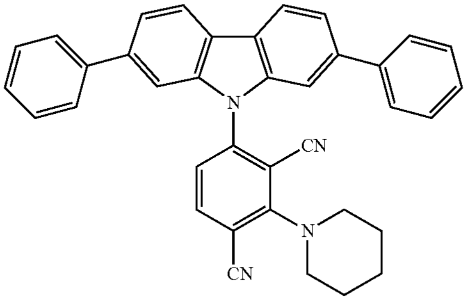
203
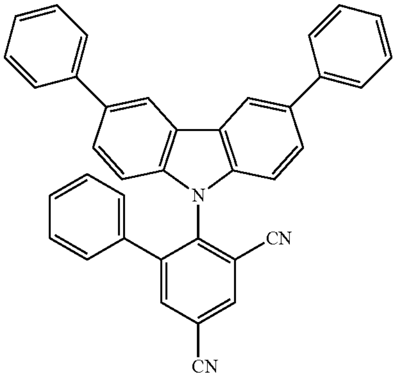
204
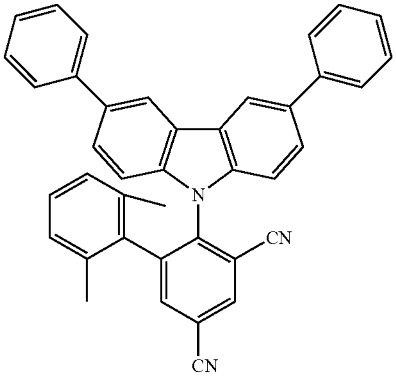
205
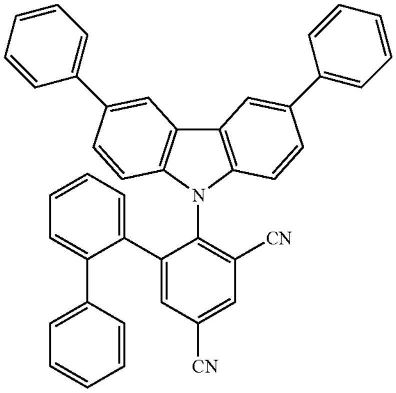
206
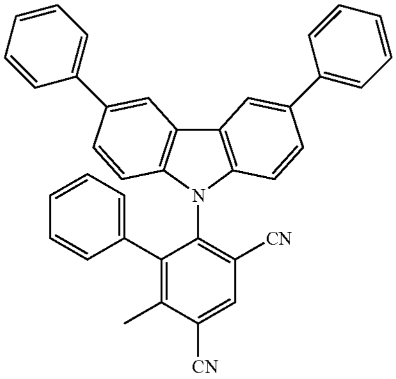
207
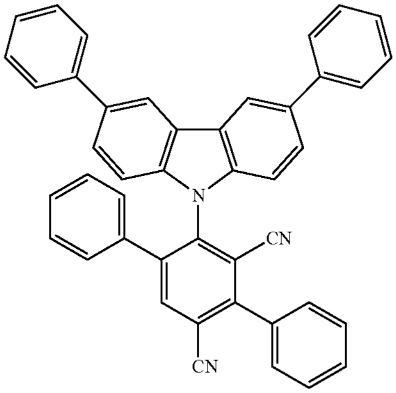
208
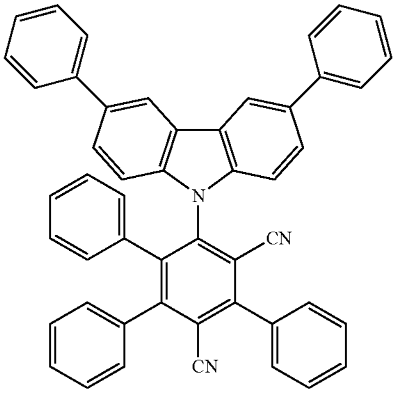

-continued
209
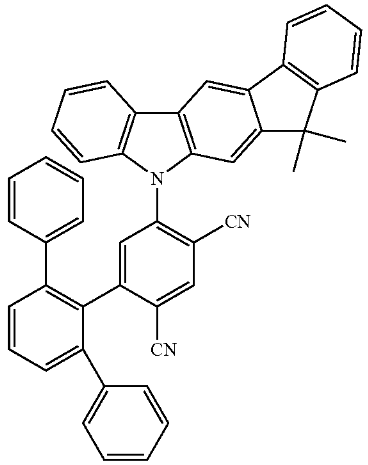
210
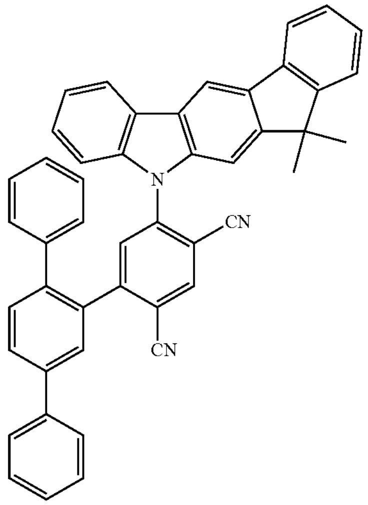
211
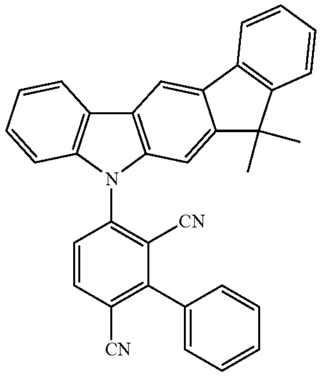
-continued
212
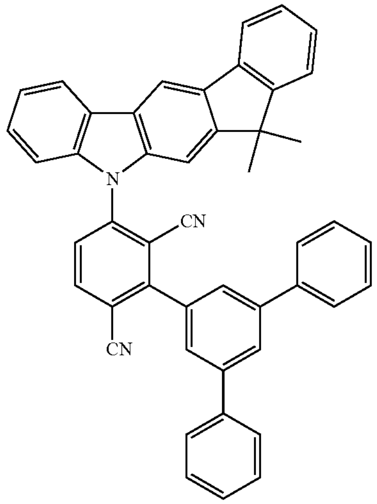
213
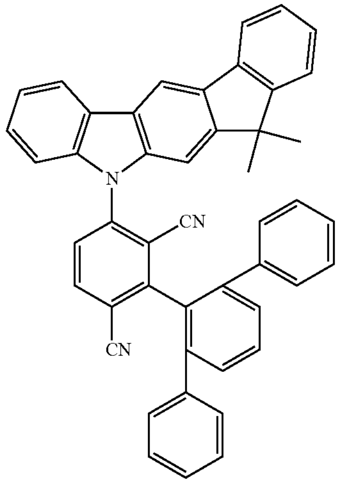
214
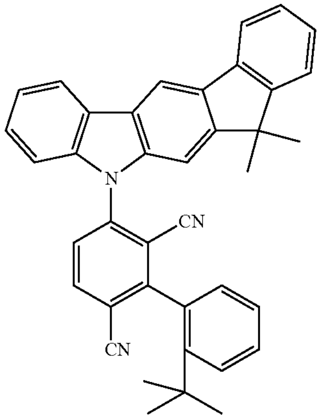

-continued
215
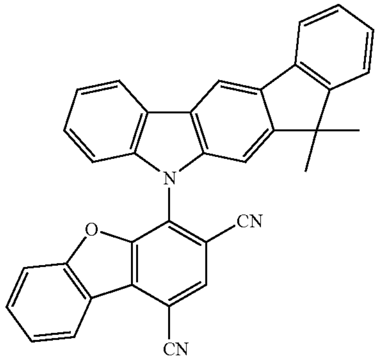
216
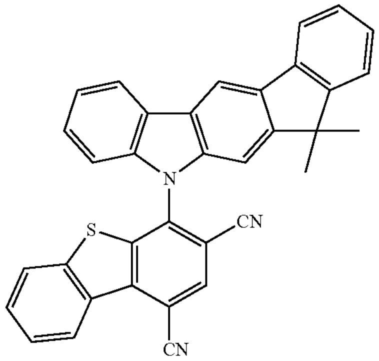
217
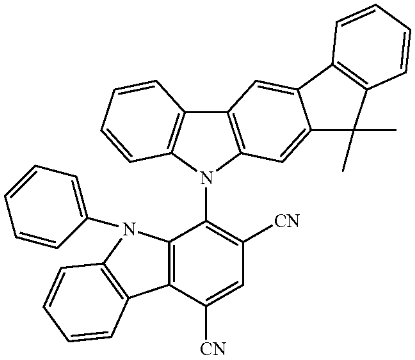
218
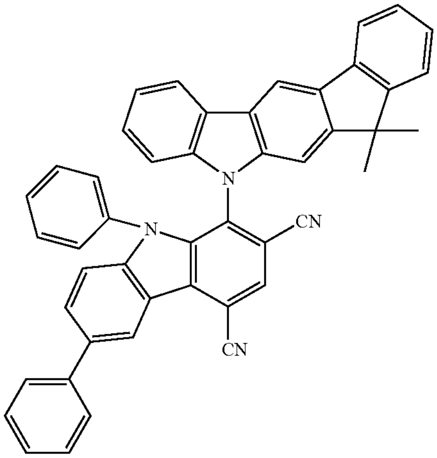
-continued
219
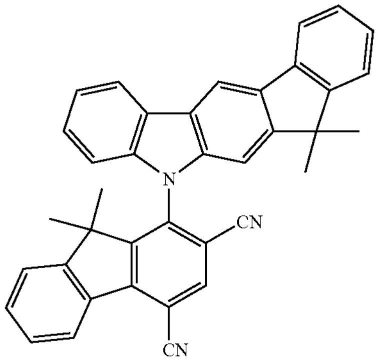
220
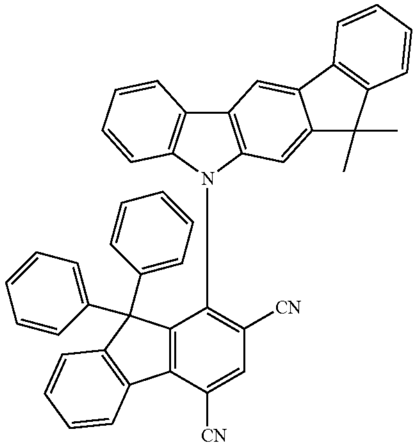
221
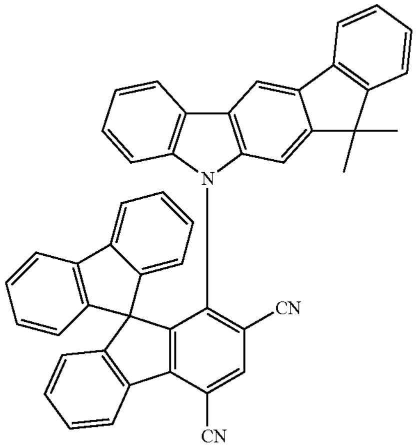
222
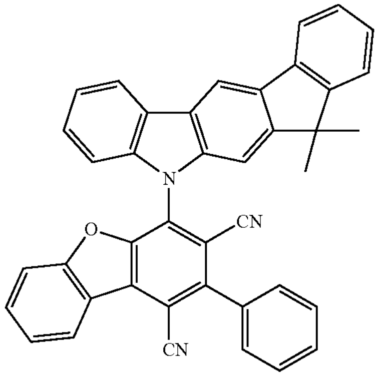

223
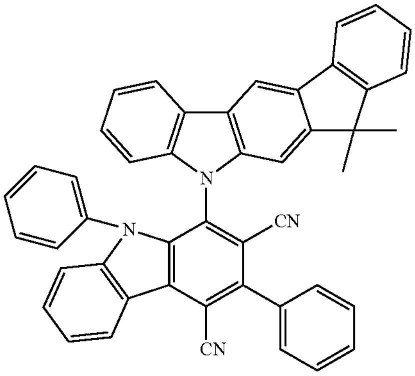
224
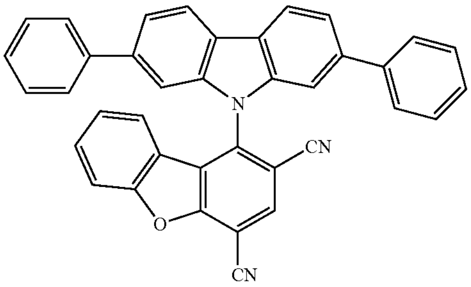
225
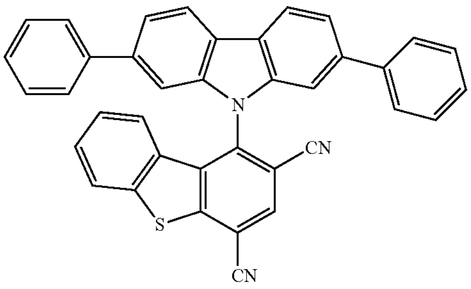
226
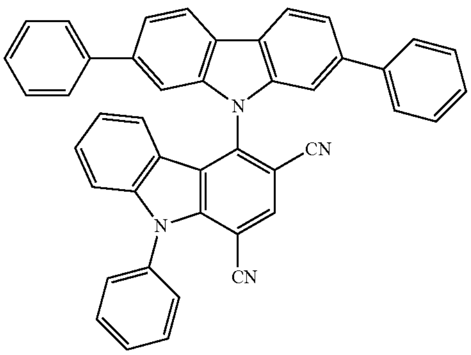
227
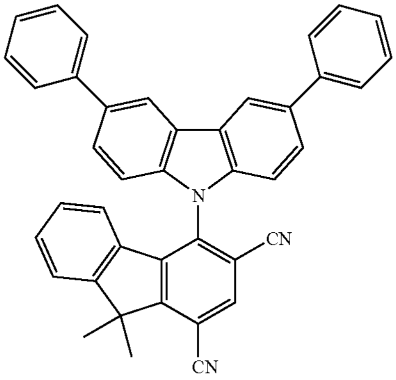
228
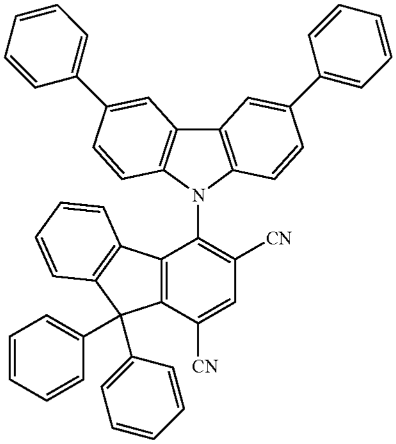
229
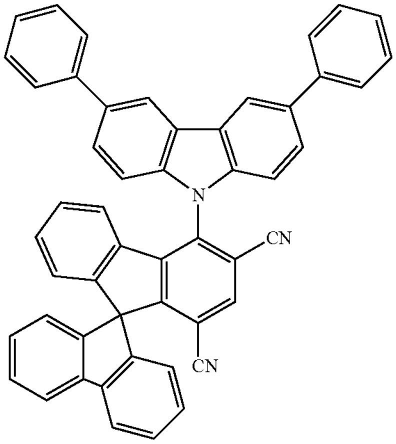

-continued
230
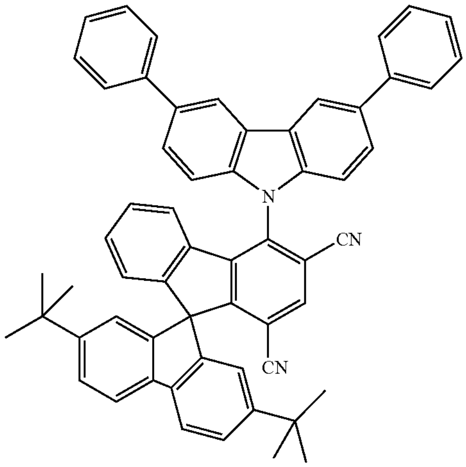
231
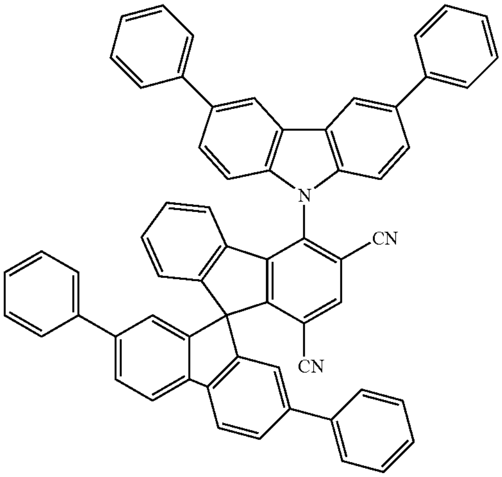
232
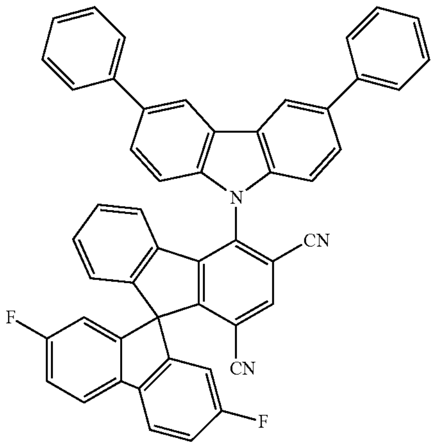
-continued
233
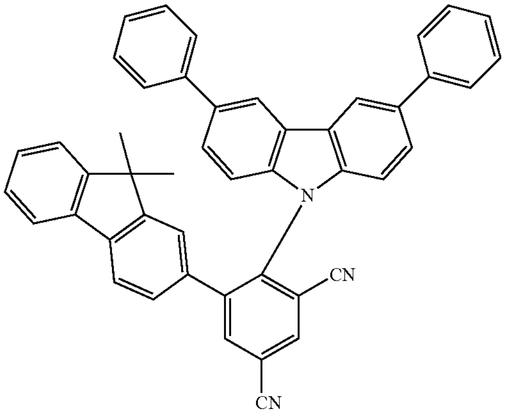
234
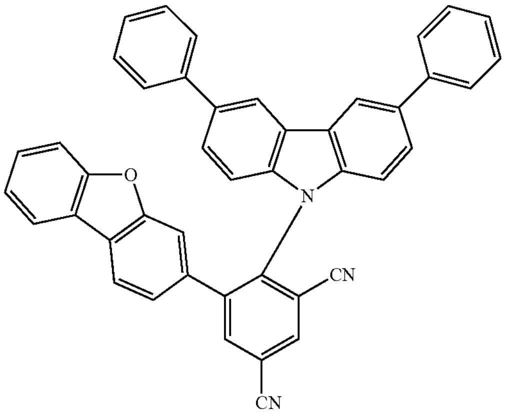
235
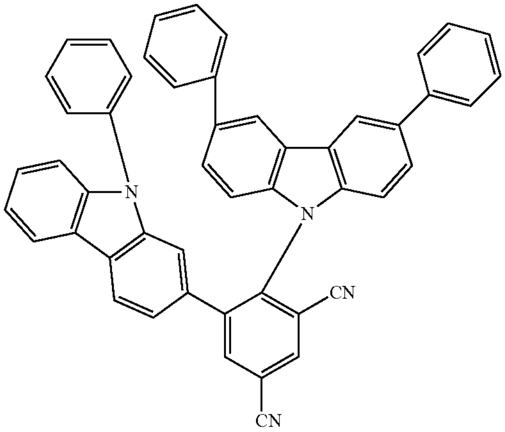

-continued
236
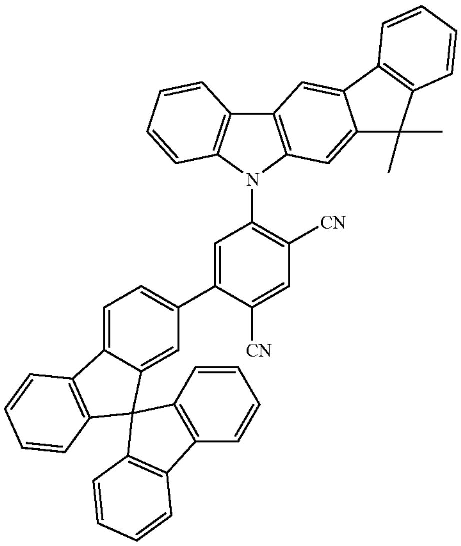
237
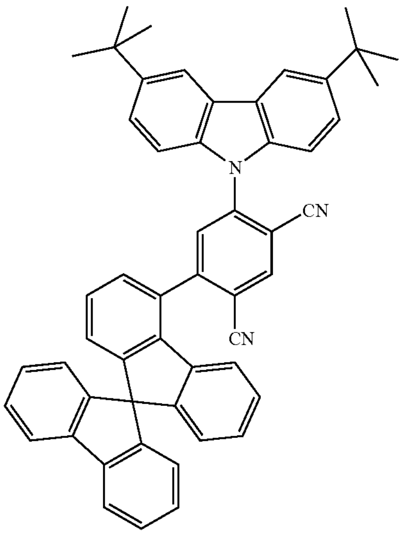
238
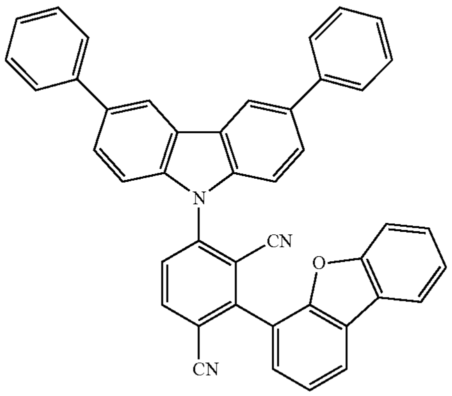
-continued
239
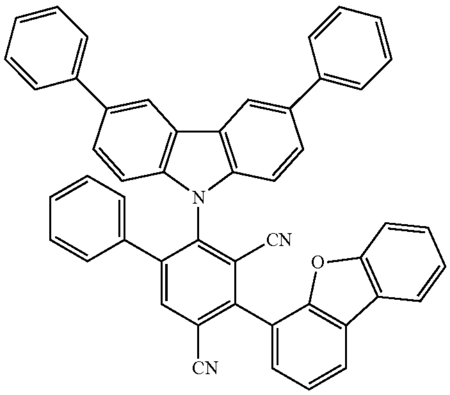
240
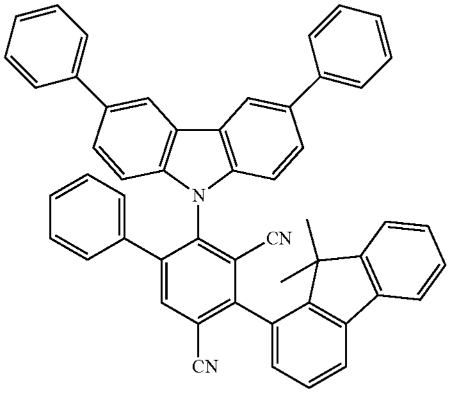
241
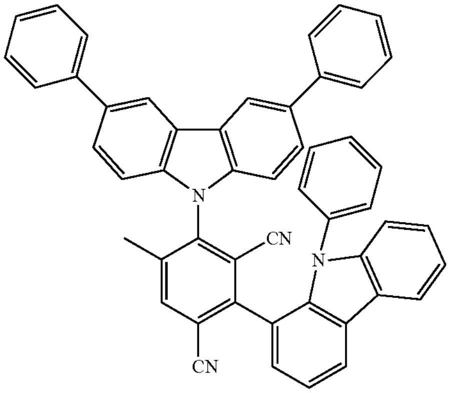
242
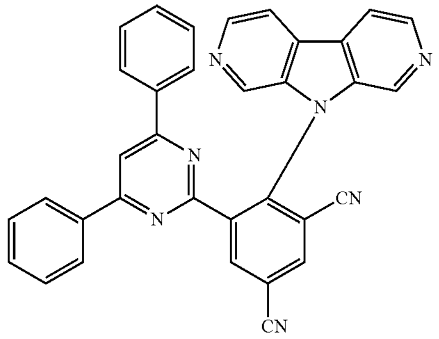

-continued
243
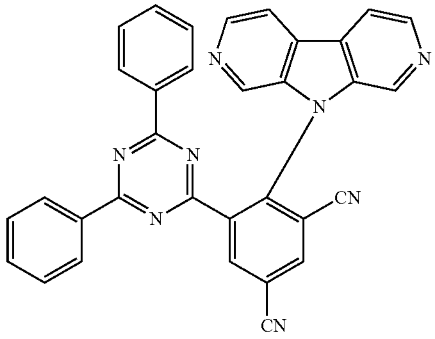
244
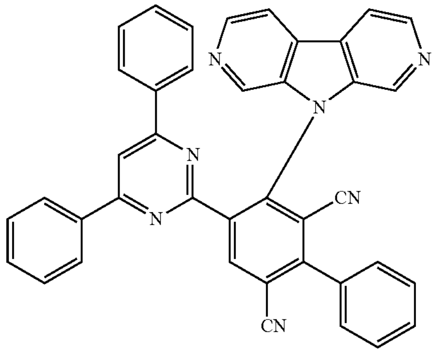
245
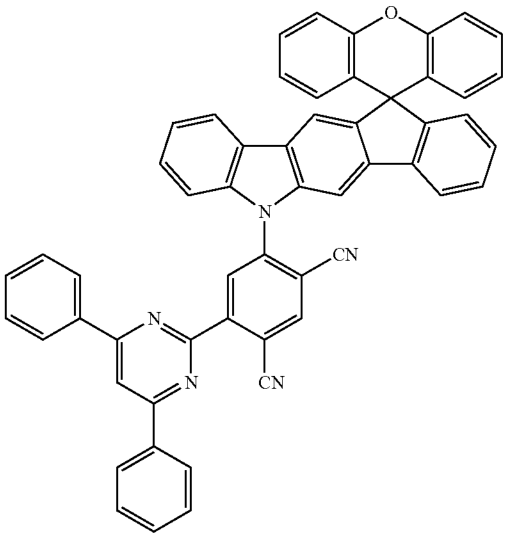
-continued
246
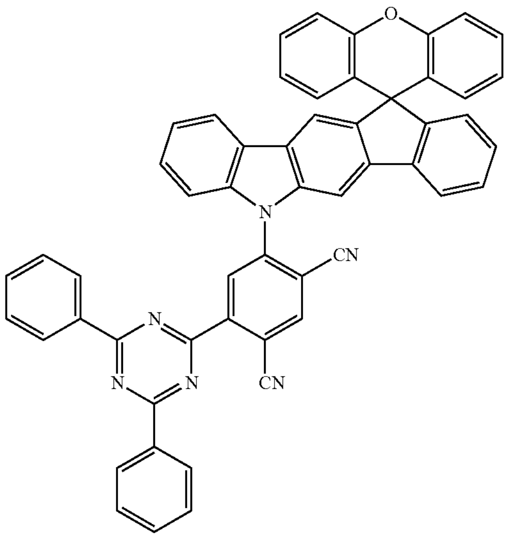
247
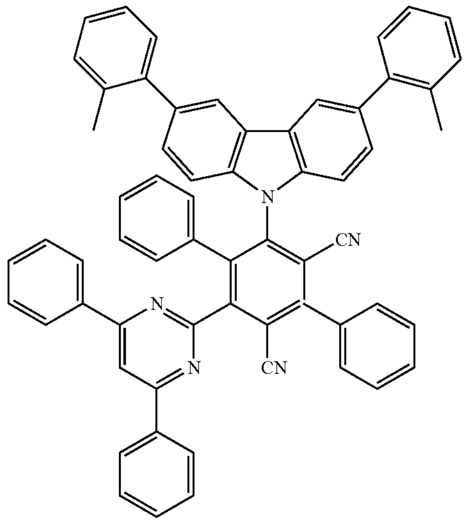
248
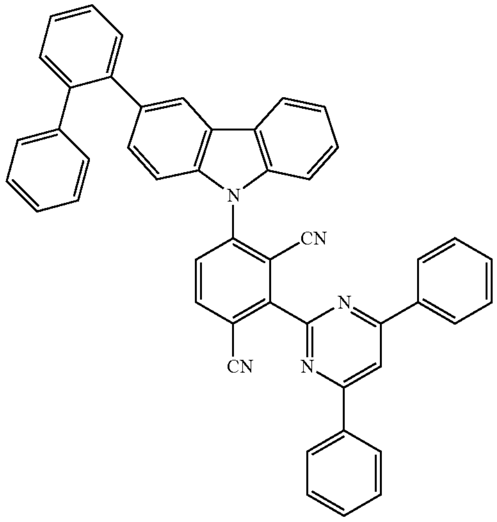

-continued
249
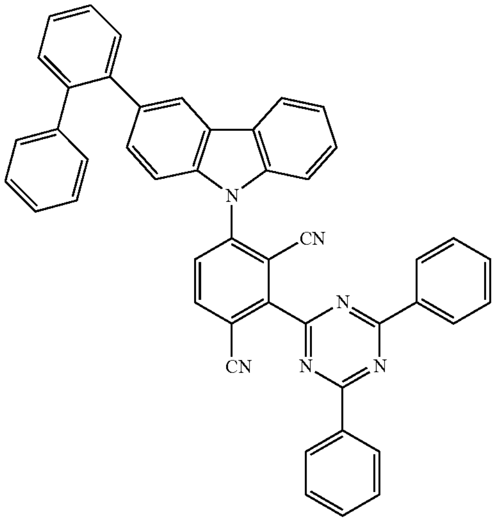
250
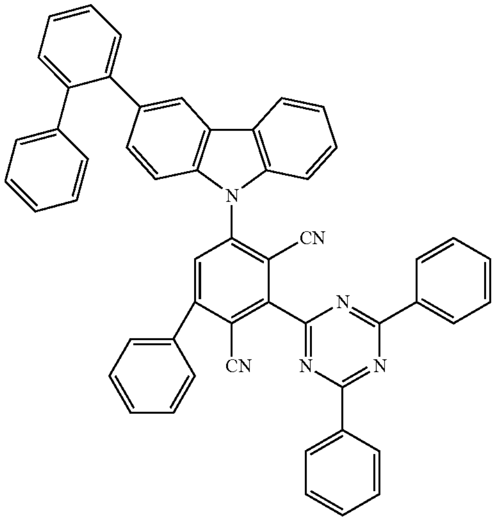
251
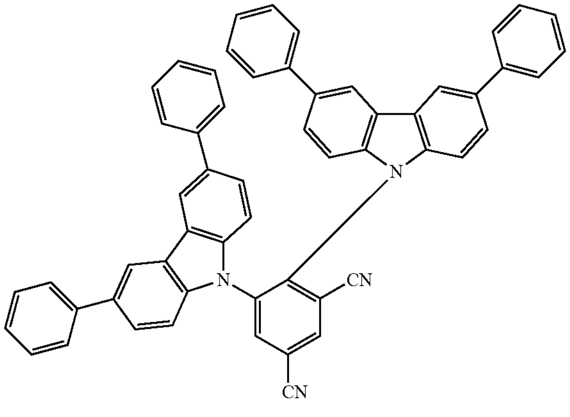
-continued
252
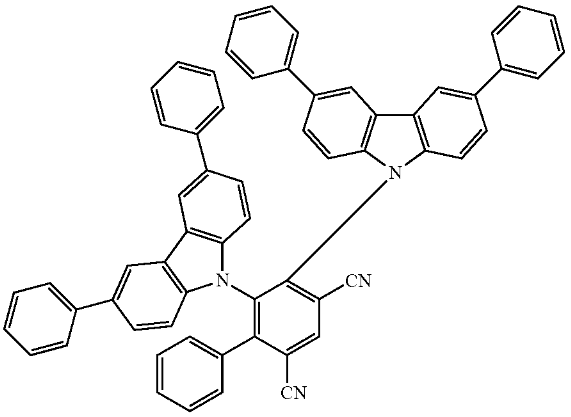
253
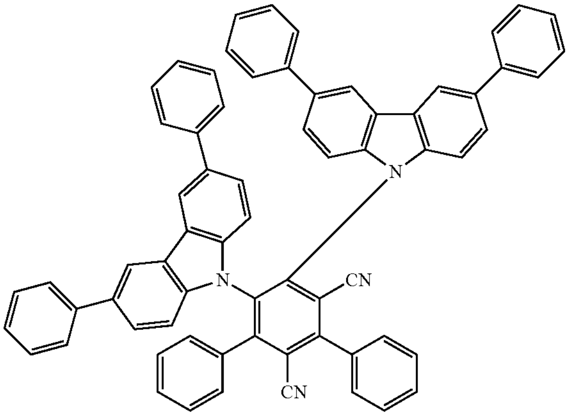
254
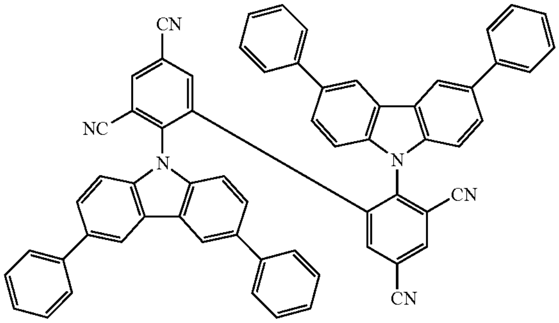
255
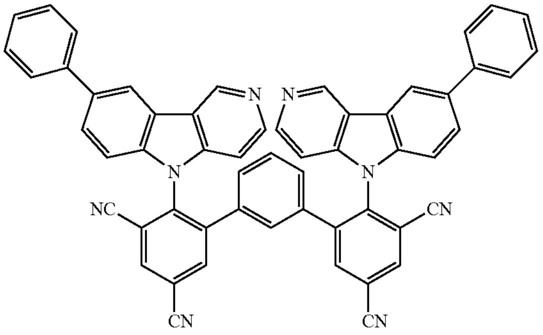

-continued
256
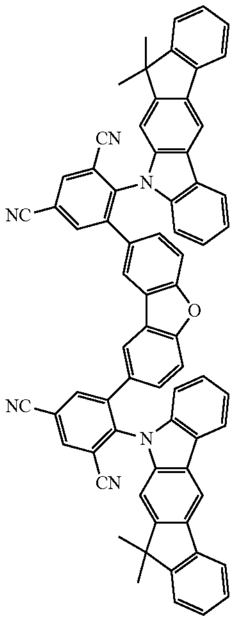
257
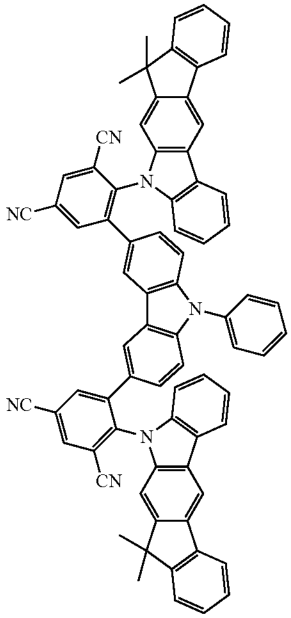
-continued
258
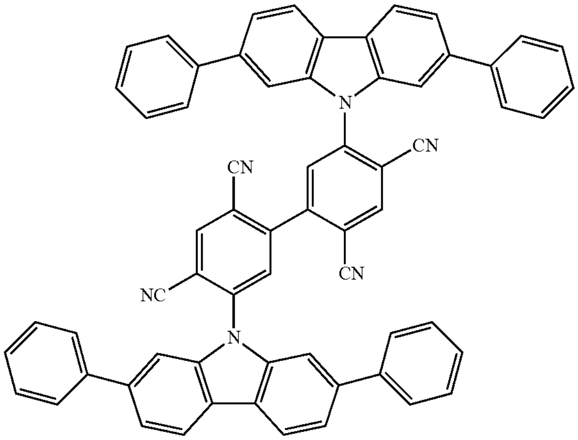
259
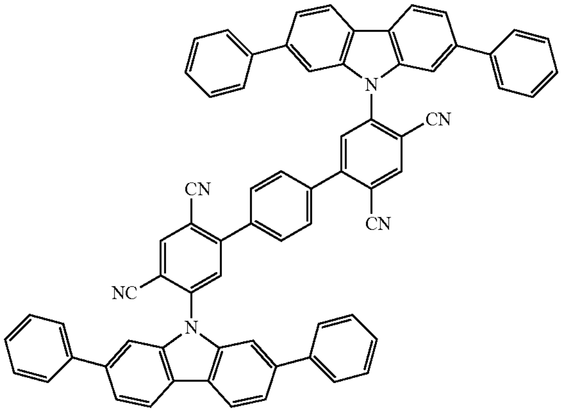
260
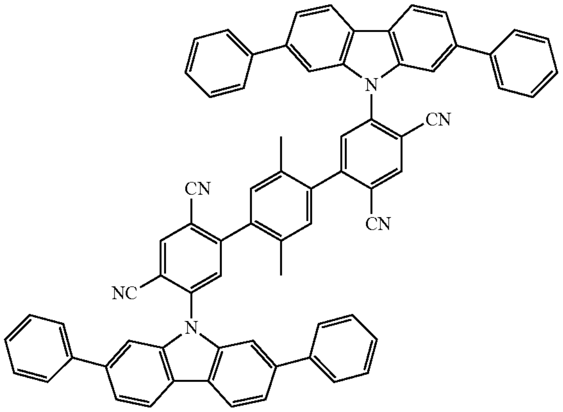

-continued

261

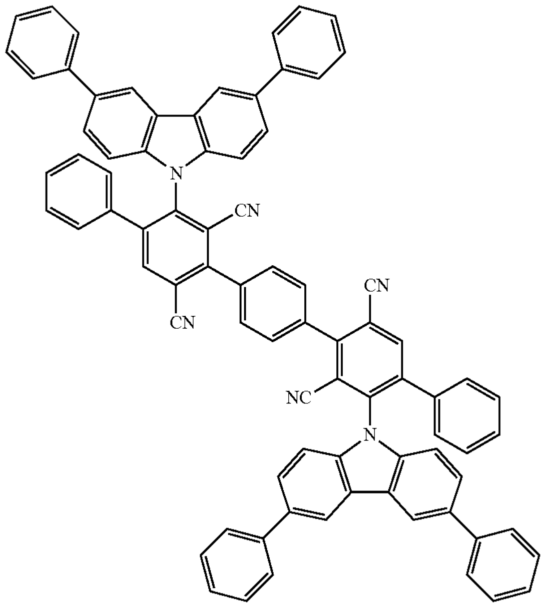

The compounds of formula (I) can be prepared using known organic chemistry synthesis steps, for example bromination, boronation, nucleophilic aromatic substitution and transition metal-catalyzed coupling reaction, for example Buchwald coupling.

Scheme 1 shows an illustrative process for preparing compounds of formula (I), which proceeds from a cyano-substituted compound (commercially available in many cases) bearing one or more fluorine substituents. In this process, one or more carbazole derivatives are introduced by nucleophilic aromatic substitution. The process can be effected stepwise, and so it is first possible to introduce a carbazole derivative, and then subsequently a further, different carbazole derivative (see bottom line). Instead of CN, it is possible to use other electron-withdrawing groups. The compounds shown may have any desired further substitution, as per the substituents defined in claim 1. This applies to all the schemes that follow which elucidate synthesis processes.

Scheme 1

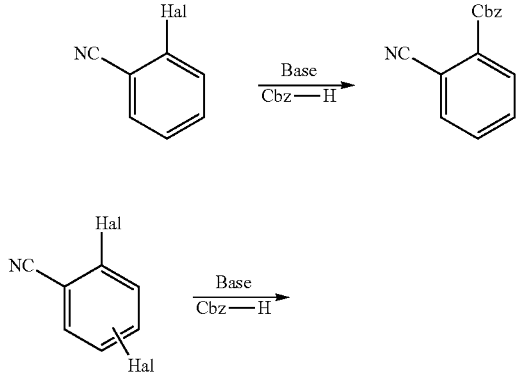

-continued

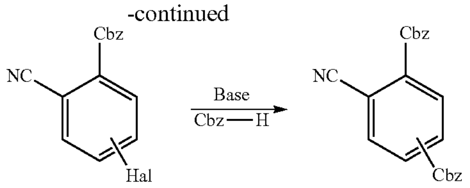

Cbz-H=optionally substituted carbazole derivative

Hal=halogen, preferably F

In addition, it is also possible to introduce carbazole derivatives into the compounds of the invention by Buchwald coupling. This is shown by way of example in scheme 2 for a compound bearing a $CF_3$ group. However, it would also be possible for other groups such as CN or F or electron-deficient heteroaromatics to be present rather than $CF_3$.

Scheme 2

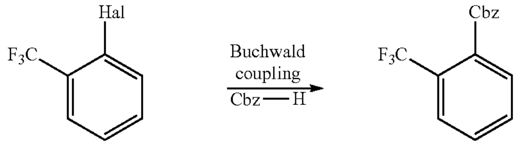

Cbz-H=optionally substituted carbazole derivative

Hal=halogen, preferably Cl, Br

An alternative process to scheme 2 for introducing a carbazole derivative is shown in scheme 3. This proceeds from a nitrobenzene derivative, which is converted to an aminobenzene derivative, which then enters into a double Buchwald coupling with a suitable halogen-substituted biaryl. Rather than the $C_6F_5$ group shown, it is also possible for other groups to be present, for example F, $CF_3$ or CN.

Scheme 3

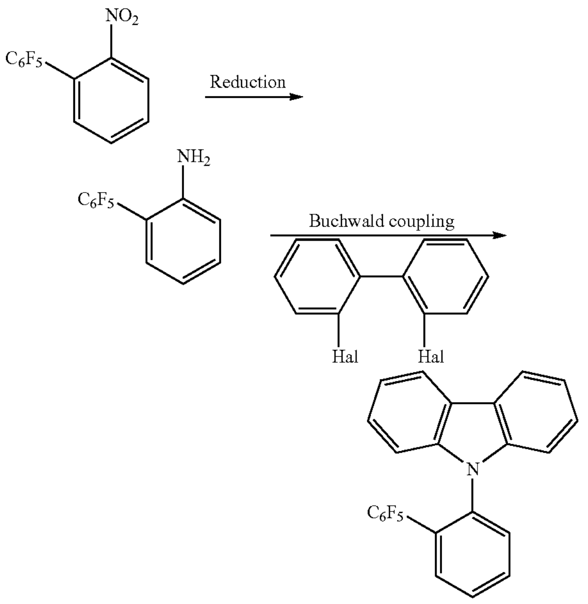

Cbz-H=optionally substituted carbazole derivative

Hal=halogen, preferably Cl, Br

Compounds in which a carbazole derivative is present in a position adjacent to an electron-withdrawing heteroaromatic system can be prepared as shown in scheme 4 below. For this purpose, the starting material is a carbazole phenyl derivative having a halogen substituent or another suitable leaving group. This compound is converted to a boronic acid, with which, in a second step, a Suzuki coupling is then conducted with an electron-deficient aromatic system. By double Suzuki coupling, it is possible to prepare compounds bearing two different heteroaryl substituents.

Scheme 4

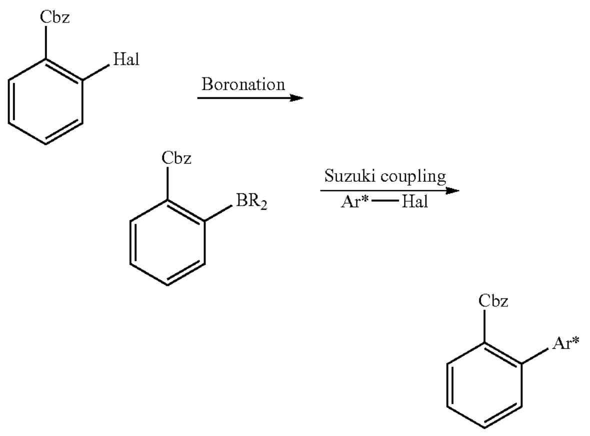

Cbz-H=optionally substituted carbazole derivative

R=any organic radical

Ar*=electron-deficient heteroaromatic system, preferably triazine or pyrimidine

Hal=halogen, preferably Cl

The synthesis processes shown above are clues for the person skilled in the art as to how compounds of the invention can be prepared over the entire scope of the claims of the present application. The person skilled in the art will consult the specific working examples present in the application for further elucidation. He will additionally drawn on his general art knowledge about organic chemistry synthesis processes and make use of commercially available compounds as starting materials, in order to prepare compounds of the invention for which no synthesis is described explicitly in the present document. In addition, within the scope of his general art knowledge, he will be able to modify the processes described here if this brings practical advantages.

In summary, the present invention provides a process for preparing a compound of formula (I), characterized in that at least one carbazole derivative is introduced by nucleophilic aromatic substitution or Buchwald coupling, or in that at least one electron-deficient heteroaryl group is introduced by Suzuki coupling. Preference is given to the specific synthesis processes specified above.

The compounds of the invention, especially compounds substituted by reactive leaving groups, such as bromine, iodine, chlorine, boronic acid or boronic ester, may find use as monomers for production of corresponding oligomers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers containing one or more compounds of formula (I), wherein the bond(s) to the oligomer may be localized at any positions substituted by $R^1$ or $R^2$ in formula (I). According to the linkage of the compound of formula (I), the compound is part of a side chain of the oligomer or part of the main chain. An oligomer in the context of this invention is understood to mean a compound formed from at least four monomer units and at most nine monomer units. The oligomers of the invention may be conjugated, partly conjugated or nonconjugated. The oligomers of the invention may be linear or branched. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched structures, it is possible, for example, for three or more units of formula (I) to be joined by a trivalent or higher-valency group, for example via a trivalent or higher-valency aromatic or heteroaromatic group, to give a branched oligomer.

For the repeat units of formula (I) in oligomers, the same preferences apply as described above for compounds of formula (I).

The oligomers of the invention can be prepared by oligomerization of one or more monomer types, of which at least one monomer leads to repeat units of the formula (I) in the oligomer. For preparation of the oligomers, the monomers of the invention are, for example, homopolymerized or copolymerized with further monomers. Suitable oligomerization reactions are known to those skilled in the art and are described in the literature.

However, the oligomers can also be prepared by stepwise organic synthesis.

The oligomers of the invention have advantageous properties, especially high lifetimes, high efficiencies and good color coordinates.

The compound of formula (I) is suitable for use in an electronic device, especially an organic electroluminescent device (OLED). Depending on the substitution, the compound of the formula (I) can be used in different functions and layers. Preference is given to use in an emitting layer, more preferably as emitting compound in an emitting layer.

The invention therefore further provides for the use of a compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides an electronic device comprising at least one compound of formula (I). This electronic device is preferably selected from the abovementioned devices.

Particular preference is given to an organic electroluminescent device comprising anode, cathode and at least one emitting layer, characterized in that at least one organic layer comprising at least one compound of formula (I) is present in the device. Preference is given to an organic electroluminescent device comprising anode, cathode and at least one emitting layer, characterized in that at least one organic layer in the device, selected from emitting layers, comprises at least one compound of formula (I).

Apart from the cathode, anode and emitting layer, the electronic device may comprise further layers. These are selected, for example, from in each case one or more hole injection layers, hole transport layers, hole blocker layers, electron transport layers, electron injection layers, electron blacker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that not every one of these layers need necessarily be present and the choice of layers always depends on the compounds used and especially also on whether the device is a fluorescent or phosphorescent electroluminescent device.

The sequence of layers in the electronic device is preferably as follows:

—anode—
—hole injection layer—
—hole transport layer—
—optionally further hole transport layers—
—emitting layer—
—electron transport layer—
—electron injection layer—
—cathode—.

It is not necessary for all the layers mentioned to be present, and further layers may additionally be present.

The person skilled in the art knows from the specialist literature of suitable compounds which can be used in the corresponding layers.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose.

Preferred anodes are materials having a high work function. Preferably, the anode has a work function of greater than 4.5 eV versus vacuum. Firstly, metals having a high redox potential are suitable for this purpose, for example Ag, Pt or Au. On the other hand, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

If the compound of formula (I) is used as emitting compound in an emitting layer, it is preferable that a matrix compound, as defined above, is present in the layer as a further component. In this case, the matrix compounds used may be the compounds known for this purpose to those skilled in the art, for example 4,4'-(biscarbazol-9-yl)biphenyl (CBP) or 2,8-bis(diphenylphosphoryl)dibenzo[b,d]thiophene (PPT).

In addition, in the case of use as emitting compound, it is preferable that the compound is present in the emitting layer in a proportion between 0.1% and 50.0% by volume, more preferably between 0.5% and 20.0% by volume and most preferably between 0.5% and 8.0% by volume.

The person skilled in the art is aware of suitable processes for production of the electronic device. More particularly, the device, after application of the layers, is structured appropriately (according to the application), contact-connected and finally sealed, in order to rule out damaging effects by water and air.

Electronic devices comprising one or more compounds of formula (I) can be used inter alia in displays, as light sources in lighting applications and as light sources in medical or cosmetic applications (e.g. light therapy).

WORKING EXAMPLES

A) Synthesis Examples:

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR.

I) Synthesis of Compounds of the Invention:

Example S1

1,3,5-Triscyano-2,4,6-tris(N-carbazolyl)benzene

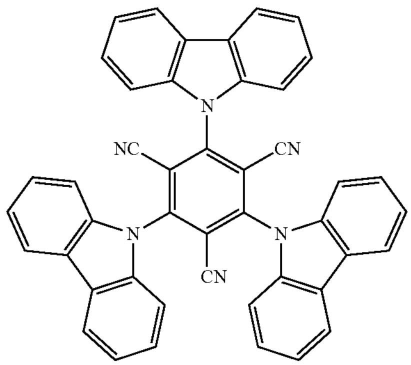 [SMILES: N#Cc1c(-n2c3ccccc3c3ccccc32)c(C#N)c(-n2c3ccccc3c3ccccc32)c(C#N)c1-n1c2ccccc2c2ccccc21]

Variant A:

To a well-stirred suspension of 16.0 g (400 mmol) of sodium hydride, 60% by weight dispersion in mineral oil, in 500 mL of THF are added in portions while cooling with ice, at about +10° C., 66.9 g (400 mmol) of carbazole [51555-21-6]—Caution! Evolution of hydrogen! Foaming! After the addition has ended, the mixture is stirred for a further 30 min and then 20.7 g (100 mmol) of 1,3,5-tricyano-2,4,6-trifluorobenzene [363897-9] are added in portions while cooling with ice in such a way that the temperature does not exceed +20° C. After the addition has ended, the mixture is stirred at +10° C. for a further 2 h, then the cooling bath is removed, and the mixture is allowed to warm to 20-25° C., stirred for a further 2 h and then heated to 40° C. for another 12 h. After cooling to room temperature, the reaction is ended by dropwise addition of 30 mL of MeOH and the reaction mixture is concentrated almost to dryness under reduced pressure. The residue is subjected to hot extractive stirring twice with 600 mL each time of a mixture of 400 mL of methanol and 200 mL of water and then once with 500 mL of methanol. Purification is effected by recrystallization from dioxane (about 5 mL/g) three times, then recrystallization from DMF (about 2.5 mL/g) five times and fractional sublimation twice (p about $1\times10^{-5}$ mbar, T about 310-320° C.). Yield: 23.6 g (36.3 mmol) 36%. Purity: 99.9% by HPLC.

Variant B:

Procedure analogous to variant A, except that the carbazole is initially charged in the THF, and then 160 mL (400 mmol) of n-BuLi, 2.5 molar in n-hexane, are added dropwise.

Yield: 19.0 g (29.3 mmol) 29%. Purity: 99.9% by HPLC.

Variant C:

A well-stirred suspension of 66.9 g (400 mmol) of carbazole [51555-21-6], 20.7 g (100 mmol) of 1,3,5-tricyano-2,4,6-trifluorobenzene, 106.1 g (500 mmol) of tripotassium phosphate (anhydrous) and 200 g of glass beads is stirred in 500 mL of dimethylacetamide at 160° C. for 16 h. After cooling, 1000 mL of water are added, the precipitated solids are filtered off, and these are washed twice with 300 mL each time of water and twice with 200 mL each time of methanol, and then dried under reduced pressure. Further purification analogously to variant A. Yield: 20.5 g (31.6 mmol) 31%. Purity: 99.9% by HPLC.

In an analogous manner, it is possible to prepare the following compounds:

| Ex. | Variant Reactants | Product | Yield |
|---|---|---|---|
| S2 | A<br>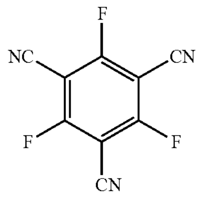<br>363897-9<br>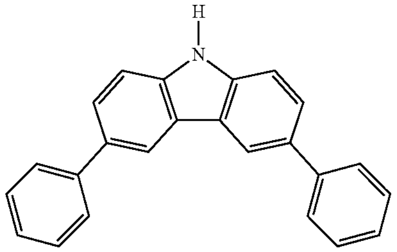<br>56525-79-2 | 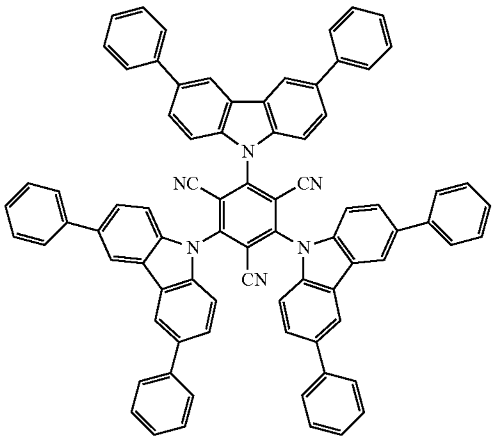 [SMILES: N#Cc1c(-n2c3ccc(-c4ccccc4)cc3c3cc(-c4ccccc4)ccc32)c(C#N)c(-n2c3ccc(-c4ccccc4)cc3c3cc(-c4ccccc4)ccc32)c(C#N)c1-n1c2ccc(-c3ccccc3)cc2c2cc(-c3ccccc3)ccc21] | 30% |
| S3 | A<br>363897-9<br>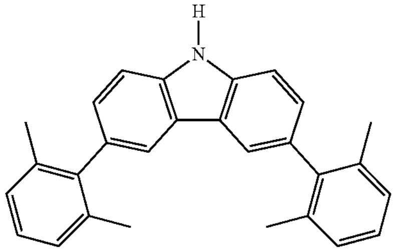<br>1246891 | 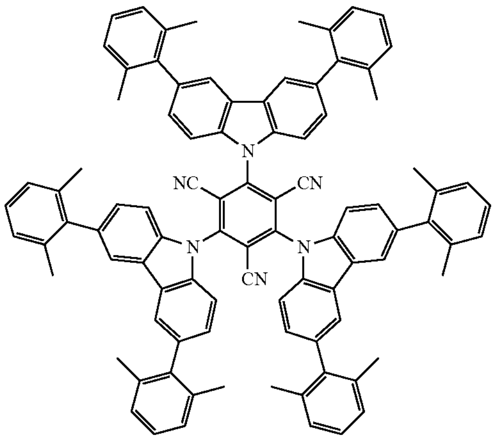 [SMILES: Cc1cccc(C)c1-c1ccc2c(c1)c1cc(-c3c(C)cccc3C)ccc1n2-c1c(C#N)c(-n2c3ccc(-c4c(C)cccc4C)cc3c3cc(-c4c(C)cccc4C)ccc32)c(C#N)c(-n2c3ccc(-c4c(C)cccc4C)cc3c3cc(-c4c(C)cccc4C)ccc32)c1C#N] | 33% |

-continued
| Ex. | Variant Reactants | Product | Yield |
| --- | --- | --- | --- |
| S4 | A<br>363897-9<br>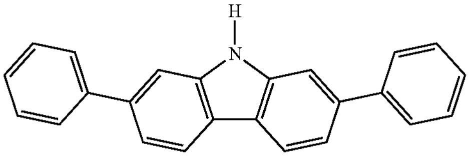<br>42448-04-4 | 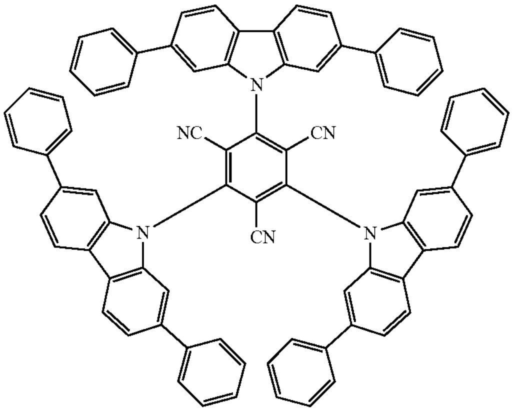 [SMILES: N#Cc1c(-n2c3cc(-c4ccccc4)ccc3c3ccc(-c4ccccc4)cc32)c(C#N)c(-n2c3cc(-c4ccccc4)ccc3c3ccc(-c4ccccc4)cc32)c(C#N)c1-n1c2cc(-c3ccccc3)ccc2c2ccc(-c3ccccc3)cc21] | 36% |
| S5 | A<br>363897-9<br>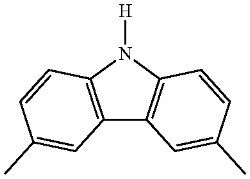<br>5599-50-9 | 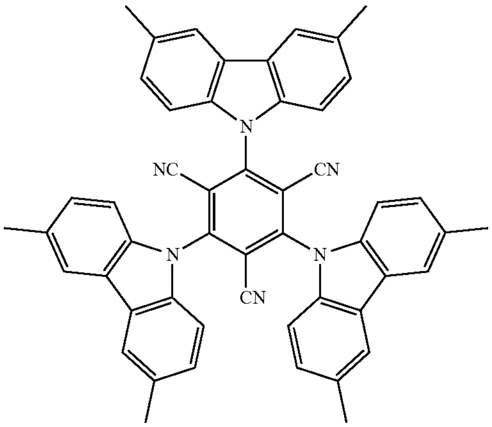 | 32% |
| S6 | A<br>363897-9<br>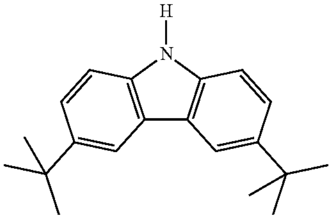<br>37500-95-1 | 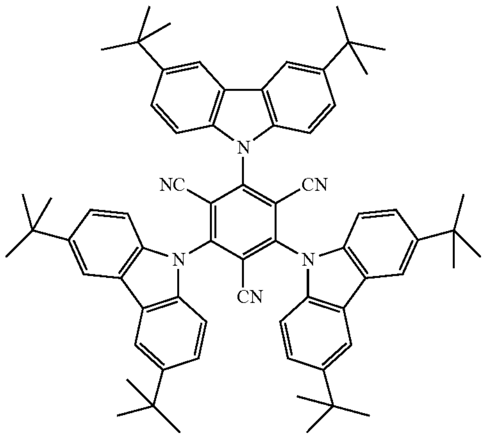 [SMILES: CC(C)(C)c1ccc2c(c1)c1cc(C(C)(C)C)ccc1n2-c1c(C#N)c(-n2c3ccc(C(C)(C)C)cc3c3cc(C(C)(C)C)ccc32)c(C#N)c(-n2c3ccc(C(C)(C)C)cc3c3cc(C(C)(C)C)ccc32)c1C#N] | 37% |

-continued
| Ex. | Variant Reactants | Product | Yield |
|---|---|---|---|
| S7 | A<br>363897-9<br>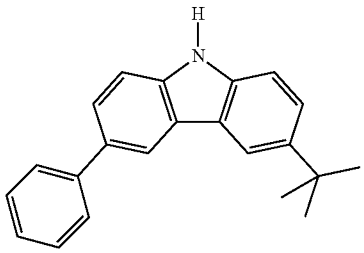<br>1335126-51-6 | 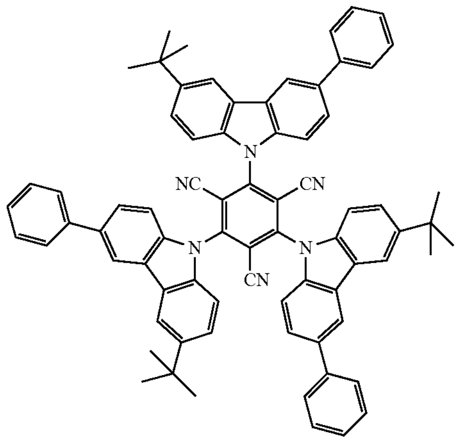 [SMILES: CC(C)(C)c1ccc2c(c1)c1cc(-c3ccccc3)ccc1n2-c1c(C#N)c(-n2c3ccc(-c4ccccc4)cc3c3cc(C(C)(C)C)ccc32)c(C#N)c(-n2c3ccc(-c4ccccc4)cc3c3cc(C(C)(C)C)ccc32)c1C#N] | 28% |
| S8 | A<br>363897-9<br>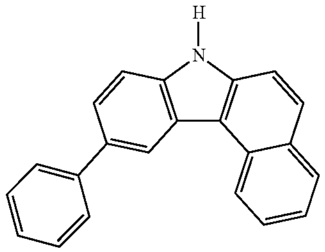<br>756822-84-1 | 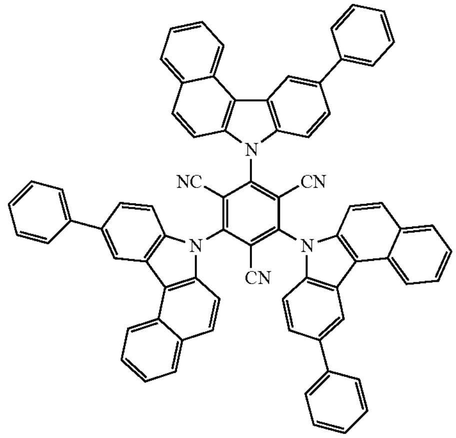 [SMILES: N#Cc1c(-n2c3ccc(-c4ccccc4)cc3c3c4ccccc4ccc32)c(C#N)c(-n2c3ccc(-c4ccccc4)cc3c3c4ccccc4ccc32)c(C#N)c1-n1c2ccc(-c3ccccc3)cc2c2c3ccccc3ccc21] | 29% |
| S9 | A<br>363897-9<br>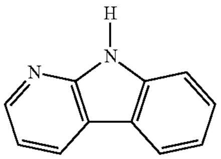<br>244-76-8 | 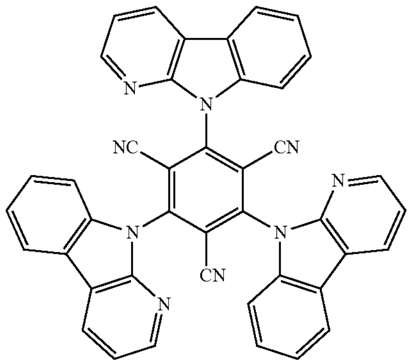 [SMILES: N#Cc1c(-n2c3ccccc3c3cccnc32)c(C#N)c(-n2c3ccccc3c3cccnc32)c(C#N)c1-n1c2ccccc2c2cccnc21] | 34% |

-continued
| Ex. | Variant Reactants | Product | Yield |
|---|---|---|---|
| S10 | C<br>363897-9<br>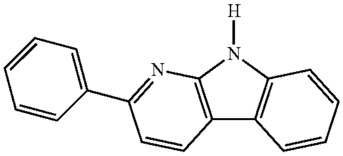<br>64677-58-3 | 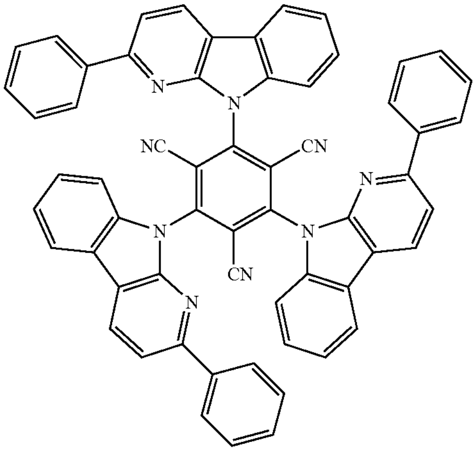 [SMILES: N#Cc1c(-n2c3ccccc3c3ccc(-c4ccccc4)nc32)c(C#N)c(-n2c3ccccc3c3ccc(-c4ccccc4)nc32)c(C#N)c1-n1c2ccccc2c2ccc(-c3ccccc3)nc21] | 28% |
| S11 | A<br>363897-9<br>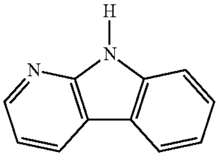<br>244-63-3 | 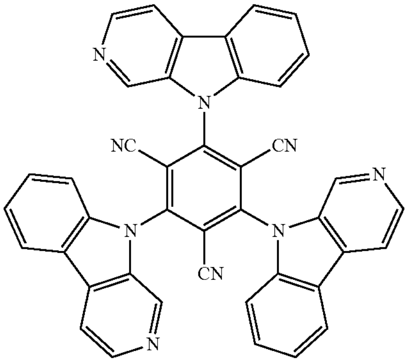 [SMILES: N#Cc1c(-n2c3ccccc3c3ccncc32)c(C#N)c(-n2c3ccccc3c3ccncc32)c(C#N)c1-n1c2ccccc2c2ccncc21] | 30% |
| S12 | A<br>363897-9<br>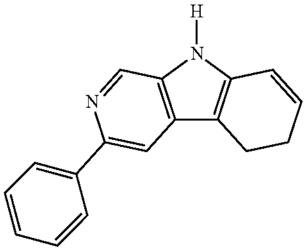<br>91944-01-3 | 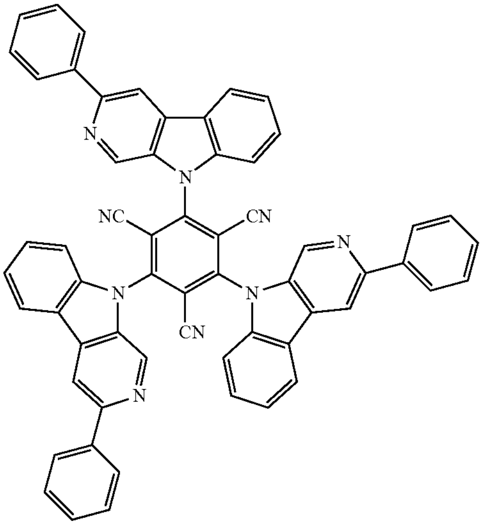 [SMILES: N#Cc1c(-n2c3ccccc3c3cc(-c4ccccc4)ncc32)c(C#N)c(-n2c3ccccc3c3cc(-c4ccccc4)ncc32)c(C#N)c1-n1c2ccccc2c2cc(-c3ccccc3)ncc21] | 31% |

-continued
| Ex. | Variant Reactants | Product | Yield |
|---|---|---|---|
| S13 | A<br>363897-9<br>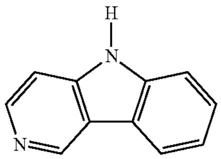<br>244-69-9 | 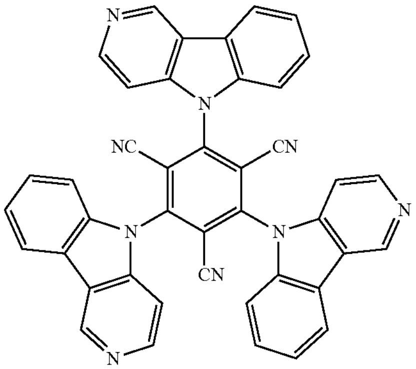 [SMILES: N#Cc1c(-n2c3ccccc3c3cnccc32)c(C#N)c(-n2c3ccccc3c3cnccc32)c(C#N)c1-n1c2ccccc2c2cnccc21] | 26% |
| S14 | A<br>363897-9<br>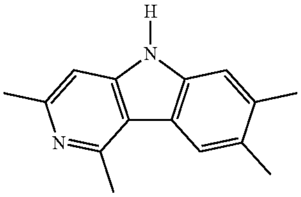<br>180520-52-9 | 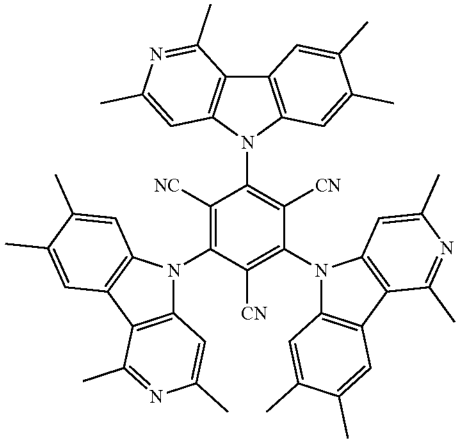 | 35% |
| S15 | A<br>363897-9<br>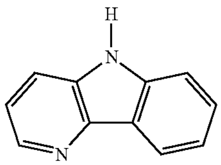<br>245-08-9 | 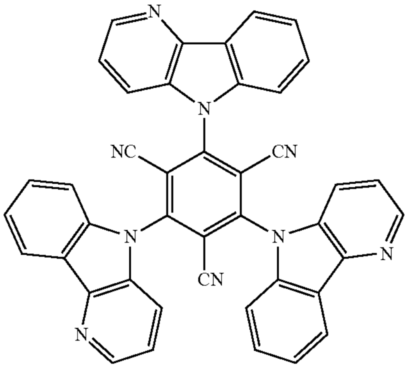 [SMILES: N#Cc1c(-n2c3ccccc3c3ncccc32)c(C#N)c(-n2c3ccccc3c3ncccc32)c(C#N)c1-n1c2ccccc2c2ncccc21] | 34% |

-continued
| Ex. | Variant Reactants | Product | Yield |
| --- | --- | --- | --- |
| S16 | A<br>363897-9<br>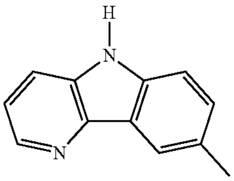<br>1041015-29-5 | 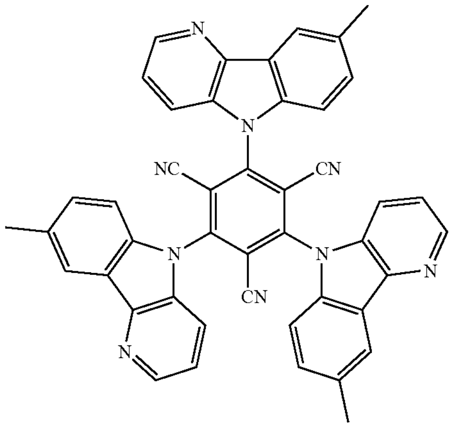 [SMILES: Cc1ccc2c(c1)c1ncccc1n2-c1c(C#N)c(-n2c3ccc(C)cc3c3ncccc32)c(C#N)c(-n2c3ccc(C)cc3c3ncccc32)c1C#N] | 32% |
| S17 | A<br>363897-9<br>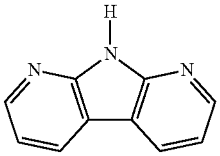<br>17966-00-6 | 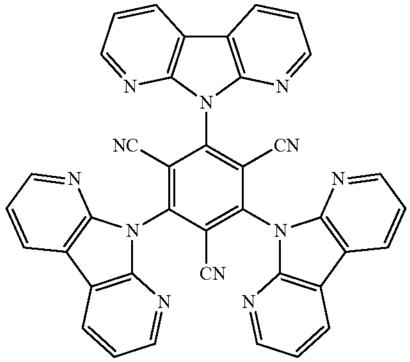 [SMILES: N#Cc1c(-n2c3ncccc3c3cccnc32)c(C#N)c(-n2c3ncccc3c3cccnc32)c(C#N)c1-n1c2ncccc2c2cccnc21] | 23% |
| S18 | A<br>363897-9<br>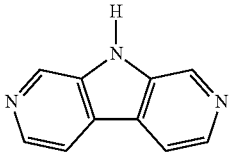<br>77200-36-3 | 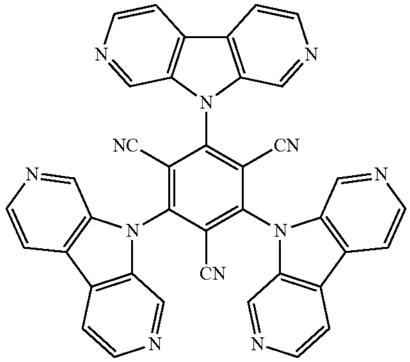 [SMILES: N#Cc1c(-n2c3cnccc3c3ccncc32)c(C#N)c(-n2c3cnccc3c3ccncc32)c(C#N)c1-n1c2cnccc2c2ccncc21] | 25% |
| S19 | A<br>363897-9<br>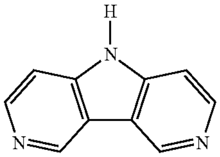<br>244-78-0 | 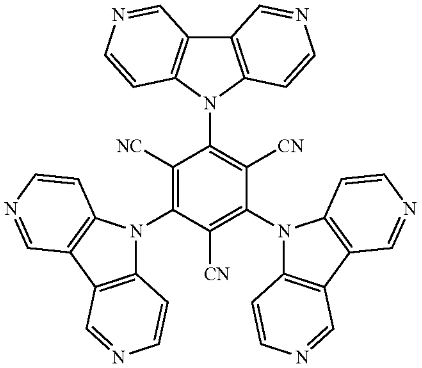 [SMILES: N#Cc1c(-n2c3ccncc3c3cnccc32)c(C#N)c(-n2c3ccncc3c3cnccc32)c(C#N)c1-n1c2ccncc2c2cnccc21] | 26% |

-continued
| Ex. | Variant Reactants | Product | Yield |
| --- | --- | --- | --- |
| S20 | C<br>363897-9<br>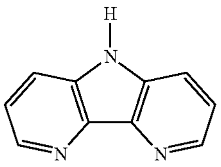<br>75449-34-2 | 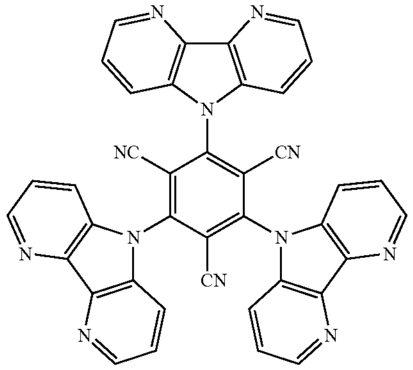 [SMILES: N#Cc1c(-n2c3cccnc3c3ncccc32)c(C#N)c(-n2c3cccnc3c3ncccc32)c(C#N)c1-n1c2cccnc2c2ncccc21] | 30% |
| S21 | A<br>363897-9<br>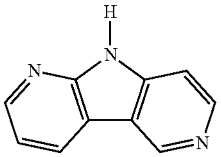<br>26422-85-5 | 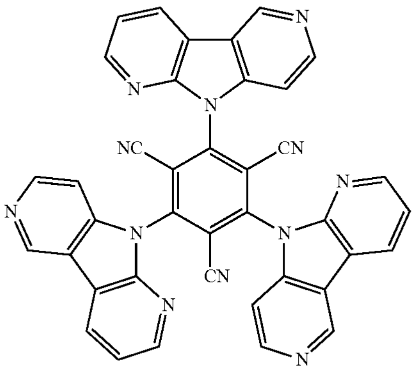 [SMILES: N#Cc1c(-n2c3ccncc3c3cccnc32)c(C#N)c(-n2c3ccncc3c3cccnc32)c(C#N)c1-n1c2ccncc2c2cccnc21] | 21% |
| S22 | A<br>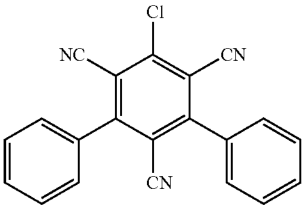<br>274258-60-5<br>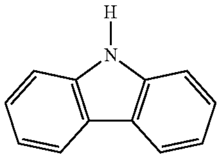<br>51555-21-6 | 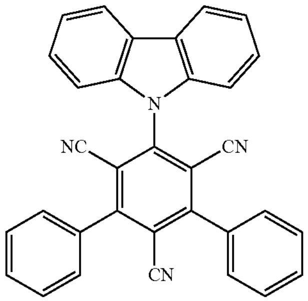<br>200 mmol of carbazole starting material are used- and hereinafter as well.<br>The mixture is stirred at 60° C. for a further 16 h. | 45% |

-continued
| Ex. | Variant Reactants | Product | Yield |
|---|---|---|---|
| S23 | A<br>274258-60-5<br>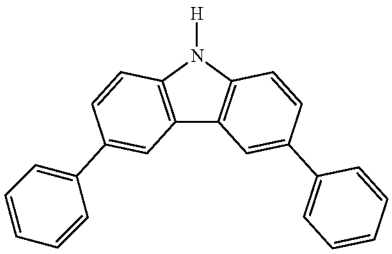<br>56525-79-2 | 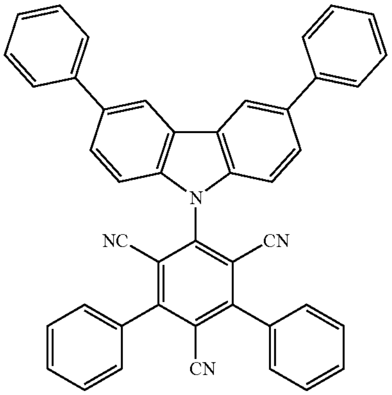 [SMILES: N#Cc1c(-c2ccccc2)c(C#N)c(-n2c3ccc(-c4ccccc4)cc3c3cc(-c4ccccc4)ccc32)c(C#N)c1-c1ccccc1] | 40% |
| S24 | A<br>274258-60-5<br>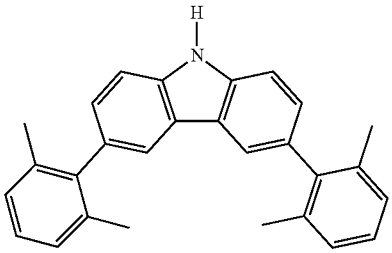<br>1246891 | 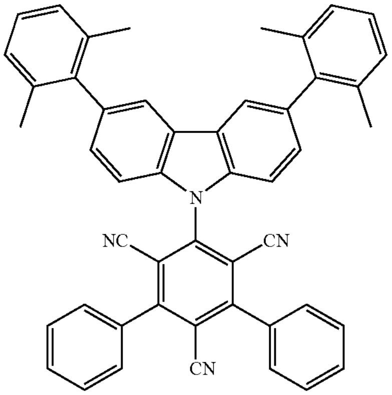 [SMILES: Cc1cccc(C)c1-c1ccc2c(c1)c1cc(-c3c(C)cccc3C)ccc1n2-c1c(C#N)c(-c2ccccc2)c(C#N)c(-c2ccccc2)c1C#N] | 41% |
| S25 | A<br>274258-60-5<br>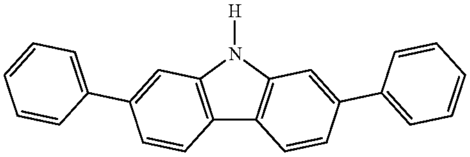<br>42448-04-4 | 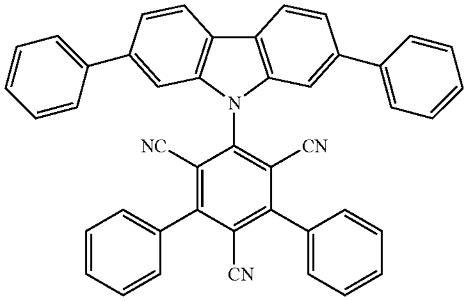 [SMILES: N#Cc1c(-c2ccccc2)c(C#N)c(-n2c3cc(-c4ccccc4)ccc3c3ccc(-c4ccccc4)cc32)c(C#N)c1-c1ccccc1] | 38% |
| S26 | B<br>274258-60-5<br>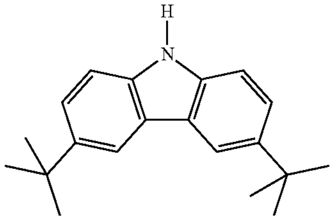<br>37500-95-1 | 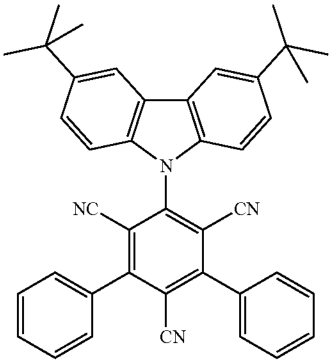 [SMILES: CC(C)(C)c1ccc2c(c1)c1cc(C(C)(C)C)ccc1n2-c1c(C#N)c(-c2ccccc2)c(C#N)c(-c2ccccc2)c1C#N] | 39% |

-continued
| Ex. | Variant Reactants | Product | Yield |
| --- | --- | --- | --- |
| S27 | A<br>274258-60-5<br>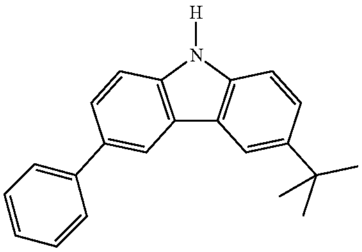<br>1335126-51-6 | 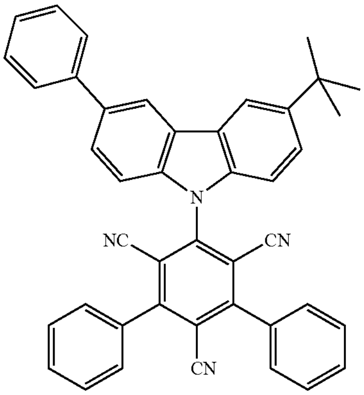 [SMILES: CC(C)(C)c1ccc2c(c1)c1cc(-c3ccccc3)ccc1n2-c1c(C#N)c(-c2ccccc2)c(C#N)c(-c2ccccc2)c1C#N] | 34% |
| S28 | A<br>274258-60-5<br>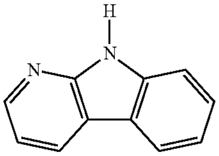<br>244-76-8 | 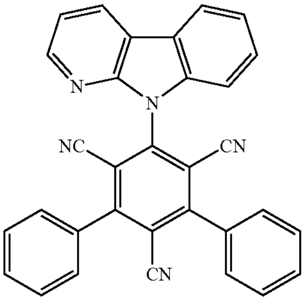 [SMILES: N#Cc1c(-c2ccccc2)c(C#N)c(-n2c3ccccc3c3cccnc32)c(C#N)c1-c1ccccc1] | 35% |
| S29 | B<br>274258-60-5<br>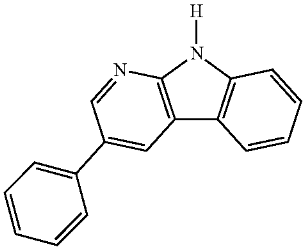<br>91944-01-3 | 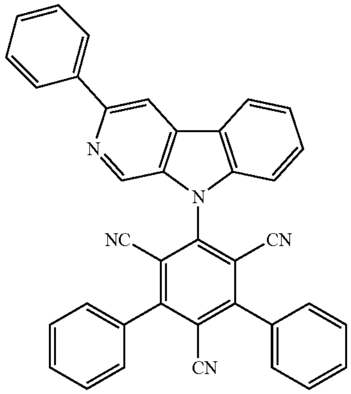 [SMILES: N#Cc1c(-c2ccccc2)c(C#N)c(-n2c3ccccc3c3cc(-c4ccccc4)ncc32)c(C#N)c1-c1ccccc1] | 33% |
| S30 | A<br>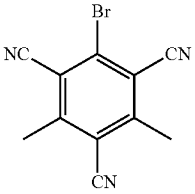<br>80717-48-2<br>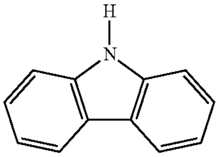<br>51555-21-6 | 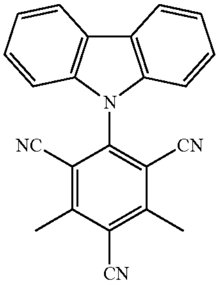<br>200 mmol of carbazole starting material are used- and hereinafter as well. The mixture is stirred at 60° C. for a further 16 h. | 16% |

-continued
| Ex. | Variant Reactants | Product | Yield |
|---|---|---|---|
| S31 | A<br>80717-48-2<br>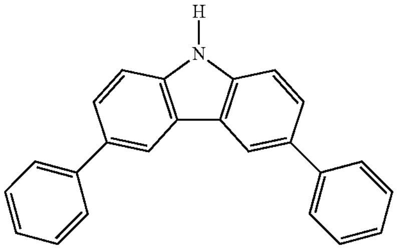<br>56525-79-2 | 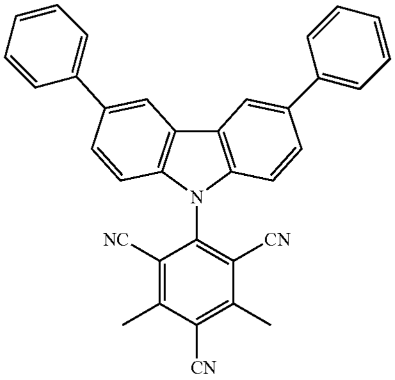 [SMILES: Cc1c(C#N)c(C)c(C#N)c(-n2c3ccc(-c4ccccc4)cc3c3cc(-c4ccccc4)ccc32)c1C#N] | 15% |
| S32 | B<br>80717-48-2<br>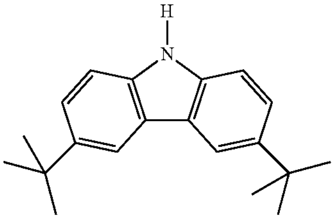<br>37500-95-1 | 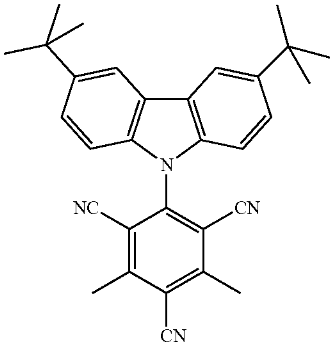 [SMILES: Cc1c(C#N)c(C)c(C#N)c(-n2c3ccc(C(C)(C)C)cc3c3cc(C(C)(C)C)ccc32)c1C#N] | 17% |
| S33 | C<br>80717-48-2<br>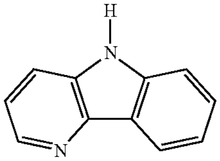<br>245-08-9 | 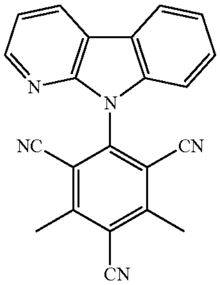 [SMILES: Cc1c(C#N)c(C)c(C#N)c(-n2c3ccccc3c3cccnc32)c1C#N] | 13% |
| S34 | A<br>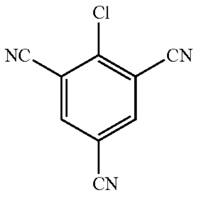<br>34760-78-8<br>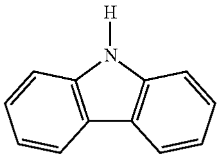<br>51555-21-6 | 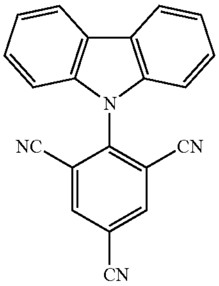<br>200 mmol of carbazole starting material are used- and hereinafter as well. The mixture is stirred at 60° C. for a further 16 h. | 36% |

-continued
| Ex. | Variant Reactants | Product | Yield |
|---|---|---|---|
| S35 | A<br>34760-78-8<br>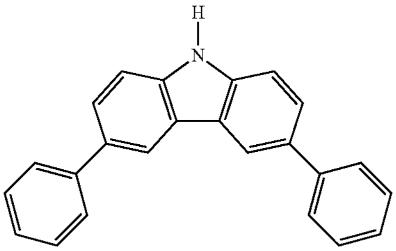<br>56525-79-2 | 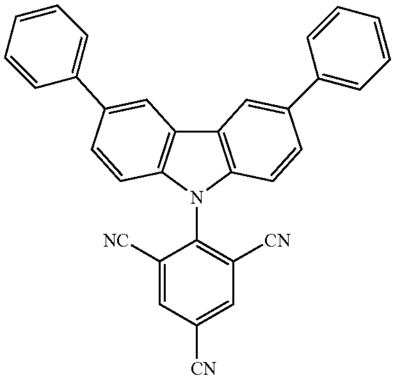 [SMILES: N#Cc1cc(C#N)c(-n2c3ccc(-c4ccccc4)cc3c3cc(-c4ccccc4)ccc32)c(C#N)c1] | 35% |
| S36 | A<br>34760-78-8<br>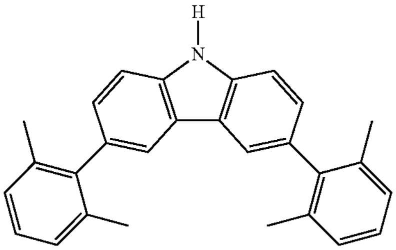<br>1246891 | 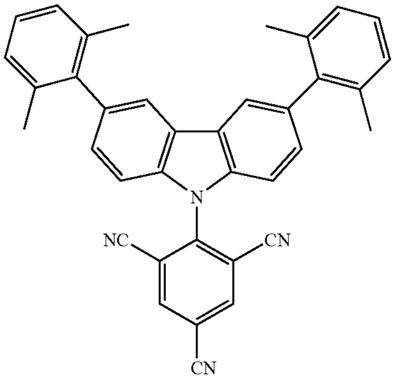 [SMILES: Cc1cccc(C)c1-c1ccc2c(c1)c1cc(-c3c(C)cccc3C)ccc1n2-c1c(C#N)cc(C#N)cc1C#N] | 31% |
| S37 | A<br>34760-78-8<br>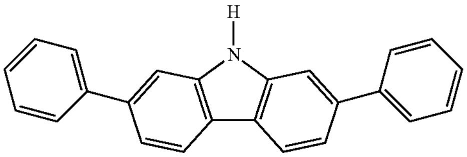<br>42448-04-4 | 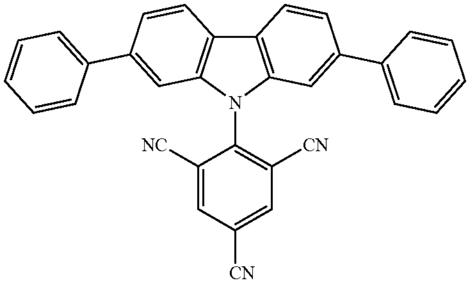 [SMILES: N#Cc1cc(C#N)c(-n2c3cc(-c4ccccc4)ccc3c3ccc(-c4ccccc4)cc32)c(C#N)c1] | 34% |
| S38 | A<br>34760-78-8<br>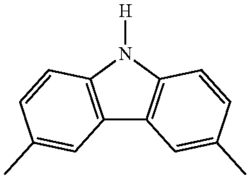<br>5599-50-8 | 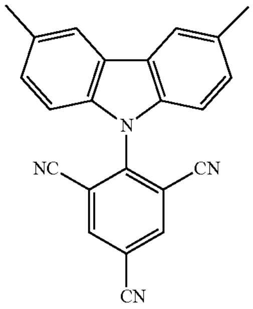 | 33% |

-continued
| Ex. | Variant Reactants | Product | Yield |
| --- | --- | --- | --- |
| S39 | C<br>34760-78-8<br>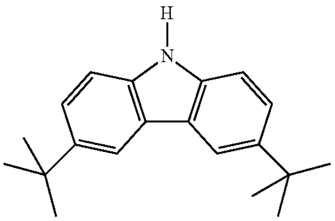<br>37500-95-1 | 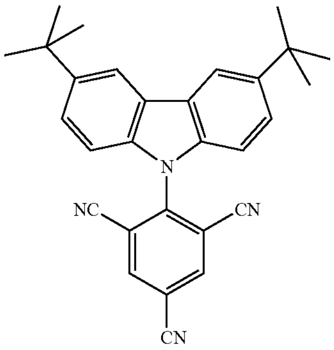 [SMILES: CC(C)(C)c1ccc2c(c1)c1cc(C(C)(C)C)ccc1n2-c1c(C#N)cc(C#N)cc1C#N] | 29% |
| S40 | A<br>34760-78-8<br>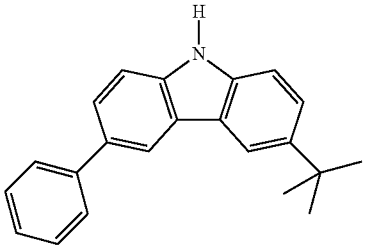<br>1335126-51-6 | 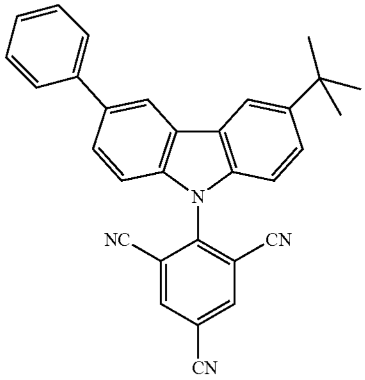 [SMILES: CC(C)(C)c1ccc2c(c1)c1cc(-c3ccccc3)ccc1n2-c1c(C#N)cc(C#N)cc1C#N] | 30% |
| S41 | A<br>34760-78-8<br>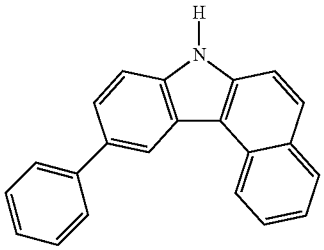<br>756822-84-1 | 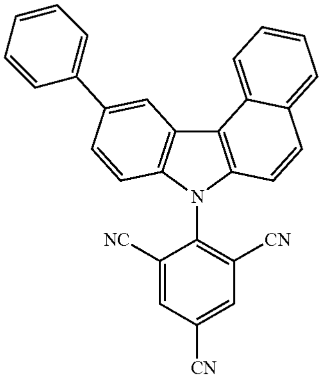 [SMILES: N#Cc1cc(C#N)c(-n2c3ccc(-c4ccccc4)cc3c3c4ccccc4ccc32)c(C#N)c1] | 26% |
| S42 | A<br>34760-78-8<br>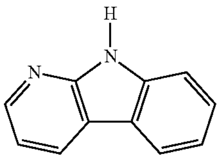<br>244-76-8 | 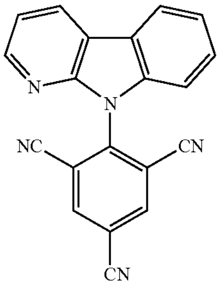 [SMILES: N#Cc1cc(C#N)c(-n2c3ccccc3c3cccnc32)c(C#N)c1] | 28% |

-continued
| Ex. | Variant Reactants | Product | Yield |
|---|---|---|---|
| S43 | A<br>34760-78-8<br>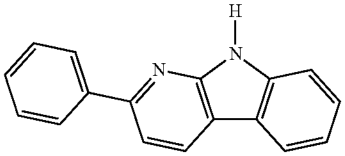<br>64677-58-3 | 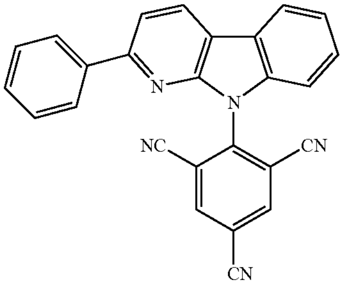 [SMILES: N#Cc1cc(C#N)c(-n2c3ccccc3c3ccc(-c4ccccc4)nc32)c(C#N)c1] | 32% |
| S44 | A<br>34760-78-8<br>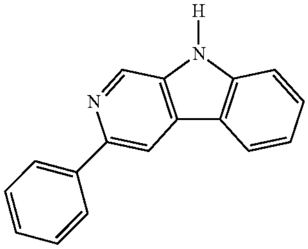<br>91944-01-3 | 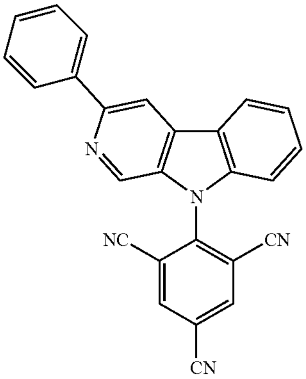 [SMILES: N#Cc1cc(C#N)c(-n2c3ccccc3c3cc(-c4ccccc4)ncc32)c(C#N)c1] | 31% |
| S45 | B<br>34760-78-8<br>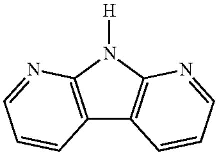<br>17966-00-6 | 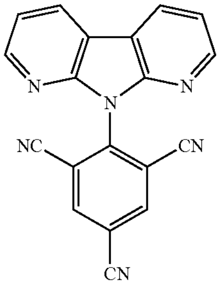 [SMILES: N#Cc1cc(C#N)c(-n2c3ncccc3c3cccnc32)c(C#N)c1] | 24% |
| S46 | A<br>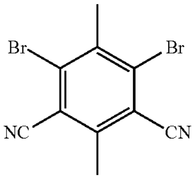<br>499154-29-9<br>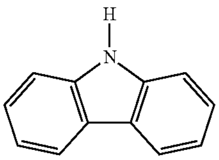<br>51555-21-6 | 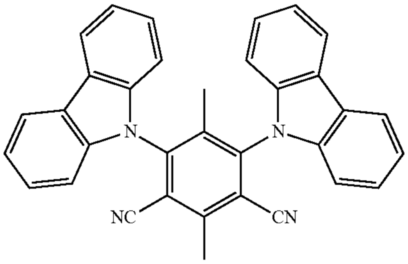<br>200 mmol of carbazole starting material are used- and hereinafter as well. The mixture is stirred at 60° C. for a further 16 h. | 19% |

-continued
| Ex. | Variant Reactants | Product | Yield |
|---|---|---|---|
| S47 | A<br>499154-29-9<br>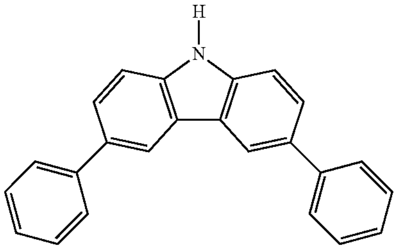<br>56525-79-2 | 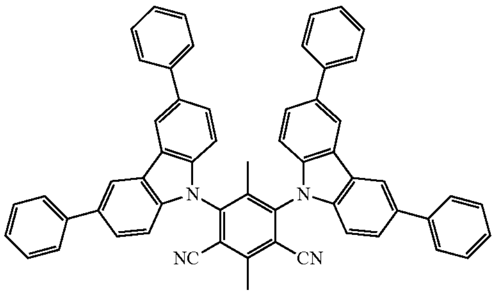 [SMILES: Cc1c(C#N)c(-n2c3ccc(-c4ccccc4)cc3c3cc(-c4ccccc4)ccc32)c(C)c(-n2c3ccc(-c4ccccc4)cc3c3cc(-c4ccccc4)ccc32)c1C#N] | 18% |
| S48 | A<br>499154-29-9<br>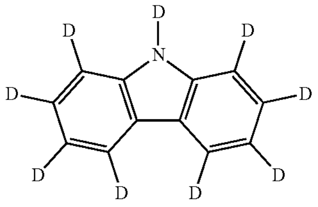<br>97960-58-2 | 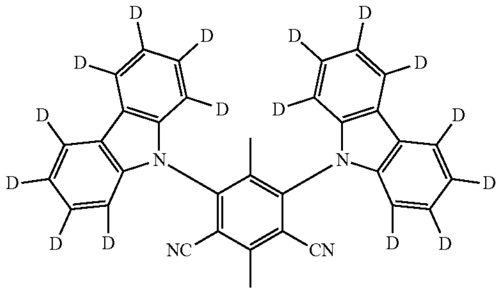 [SMILES: [2H]c1c([2H])c([2H])c2c(c1[2H])c1c([2H])c([2H])c([2H])c([2H])c1n2-c1c(C)c(-n2c3c([2H])c([2H])c([2H])c([2H])c3c3c([2H])c([2H])c([2H])c([2H])c32)c(C#N)c(C)c1C#N] | 20% |
| S49 | A<br>499154-29-9<br>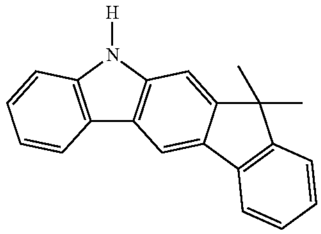<br>1257220-47-5 | 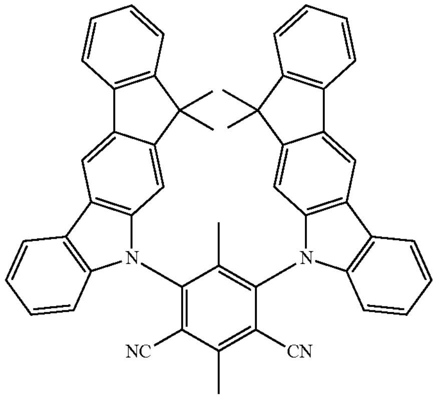 [SMILES: Cc1c(C#N)c(-n2c3ccccc3c3cc4c(cc32)C(C)(C)c2ccccc2-4)c(C)c(-n2c3ccccc3c3cc4c(cc32)C(C)(C)c2ccccc2-4)c1C#N] | 19% |
| S50 | A<br>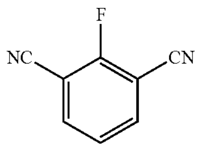<br>23039-06-7<br>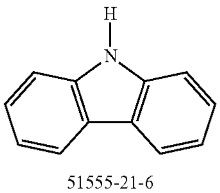<br>51555-21-6 | 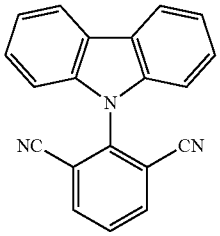<br>200 mmol of carbazole starting material are used- and hereinafter as well. | 53% |

-continued
| Ex. | Variant Reactants | Product | Yield |
|---|---|---|---|
| S51 | A<br>23039-06-7<br>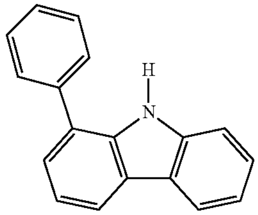<br>104636-53-5 | 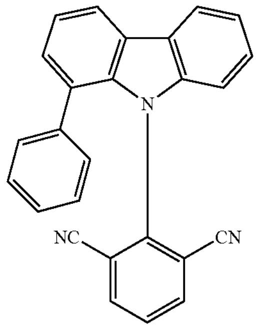 [SMILES: N#Cc1cccc(C#N)c1-n1c2ccccc2c2cccc(-c3ccccc3)c21] | 13% |
| S52 | A<br>23039-06-7<br>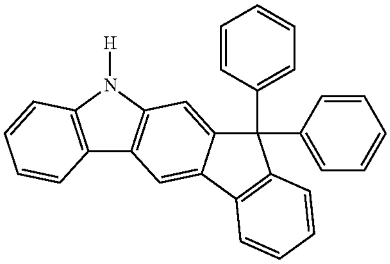<br>1257220-52-5 | 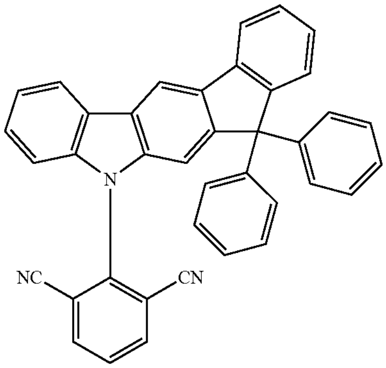 [SMILES: N#Cc1cccc(C#N)c1-n1c2ccccc2c2cc3c(cc21)C(c1ccccc1)(c1ccccc1)c1ccccc1-3] | 32% |
| S53 | A<br>23039-06-7<br>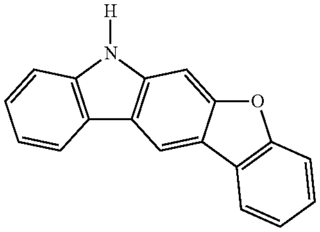<br>1246308-83-7 | 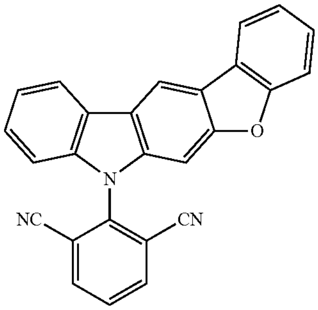 [SMILES: N#Cc1cccc(C#N)c1-n1c2ccccc2c2cc3c(cc21)oc1ccccc13] | 34% |
| S54 | A<br>23039-06-7<br>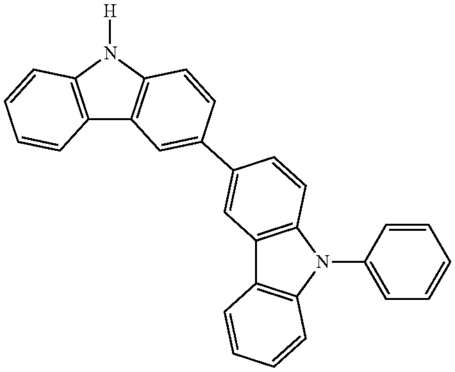<br>1060735-14-9 | 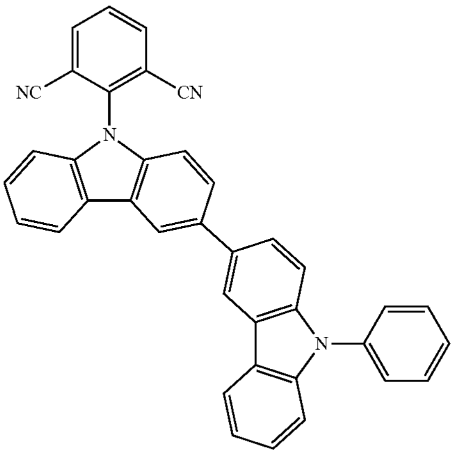 [SMILES: N#Cc1cccc(C#N)c1-n1c2ccccc2c2cc(-c3ccc4c(c3)c3ccccc3n4-c3ccccc3)ccc21] | 28% |

-continued
| Ex. | Variant Reactants | Product | Yield |
|---|---|---|---|
| S55 | A<br>23039-06-7<br>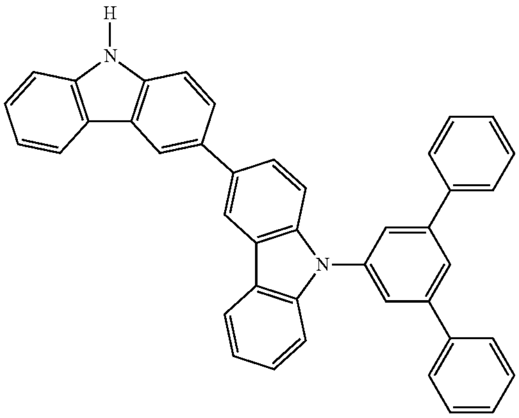<br>1415349-61-9 | 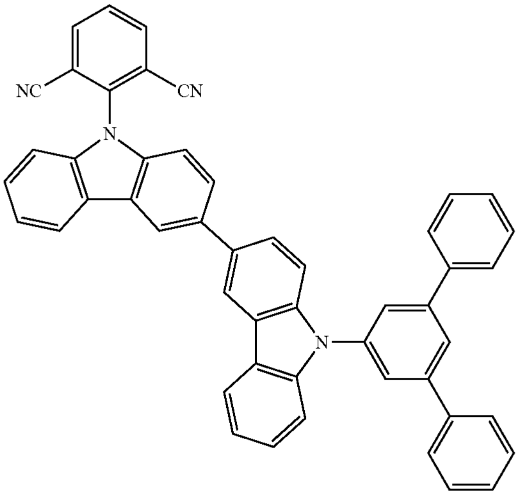 [SMILES: N#Cc1cccc(C#N)c1-n1c2ccccc2c2cc(-c3ccc4c(c3)c3ccccc3n4-c3cc(-c4ccccc4)cc(-c4ccccc4)c3)ccc21] | 33% |
| S56 | A<br>23039-06-7<br>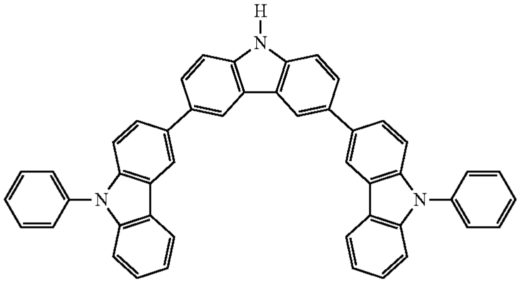<br>1060735-19-4 | 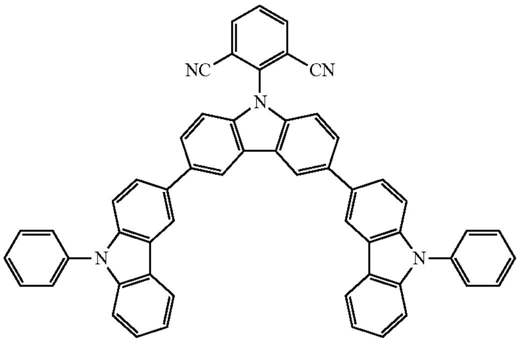 [SMILES: N#Cc1cccc(C#N)c1-n1c2ccc(-c3ccc4c(c3)c3ccccc3n4-c3ccccc3)cc2c2cc(-c3ccc4c(c3)c3ccccc3n4-c3ccccc3)ccc21] | 28% |
| S57 | A<br>23039-06-7<br>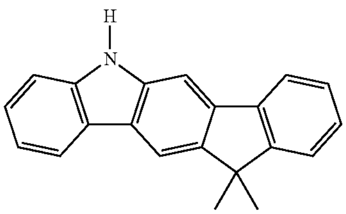<br>1260228-95-2 | 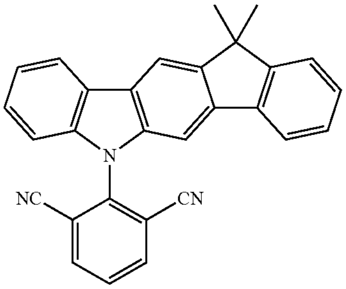 [SMILES: CC1(C)c2ccccc2-c2cc3c(cc21)c1ccccc1n3-c1c(C#N)cccc1C#N] | 30% |

-continued
| Ex. | Variant Reactants | Product | Yield |
|---|---|---|---|
| S58 | A<br>23039-06-7<br>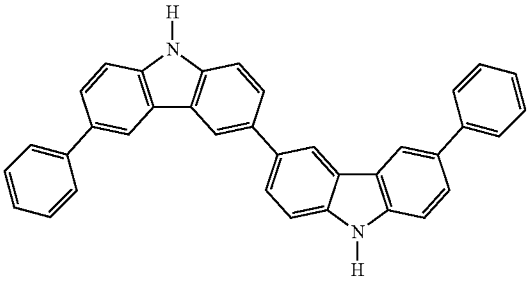<br>1303472-75-4 | 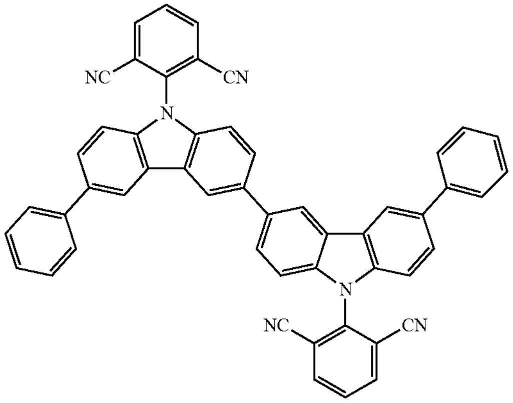 [SMILES: N#Cc1cccc(C#N)c1-n1c2ccc(-c3ccccc3)cc2c2cc(-c3ccc4c(c3)c3cc(-c5ccccc5)ccc3n4-c3c(C#N)cccc3C#N)ccc21] | 18% |
| S59 | A<br>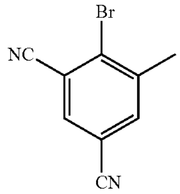<br>75344-78-4<br>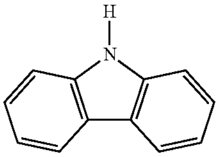<br>51555-21-6 | 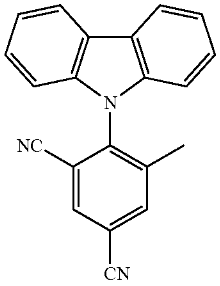<br>200 mmol of carbazole starting material are used- and hereinafter as well. The mixture is stirred at 60° C. for a further 16 h. | 16% |
| S60 | A<br>75344-78-4<br>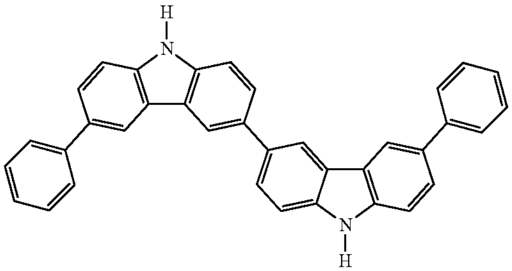<br>1303472-75-4 | 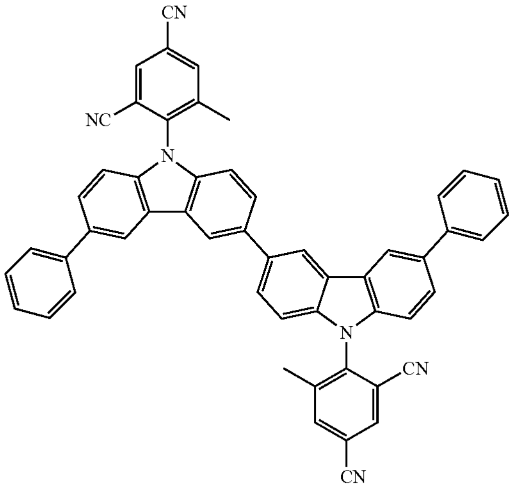 [SMILES: Cc1cc(C#N)cc(C#N)c1-n1c2ccc(-c3ccccc3)cc2c2cc(-c3ccc4c(c3)c3cc(-c5ccccc5)ccc3n4-c3c(C)cc(C#N)cc3C#N)ccc21] | 22% |

-continued
| Ex. | Variant Reactants | Product | Yield |
|---|---|---|---|
| S61 | A<br>75344-78-4<br>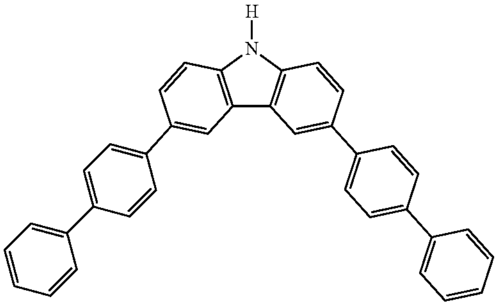<br>850264-79-8 | 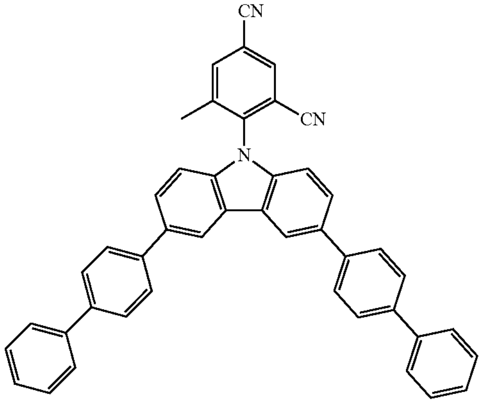 [SMILES: Cc1cc(C#N)cc(C#N)c1-n1c2ccc(-c3ccc(-c4ccccc4)cc3)cc2c2cc(-c3ccc(-c4ccccc4)cc3)ccc21] | 21% |
| S62 | A<br>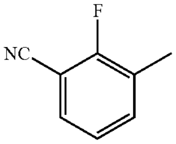<br>18547-07-3<br>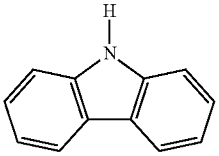<br>51555-21-6 | 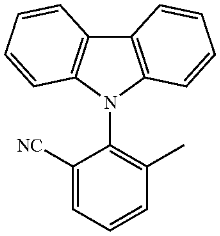<br>200 mmol of carbazole starting material are used- and hereinafter as well. | 28% |
| S63 | A<br>18547-07-3<br>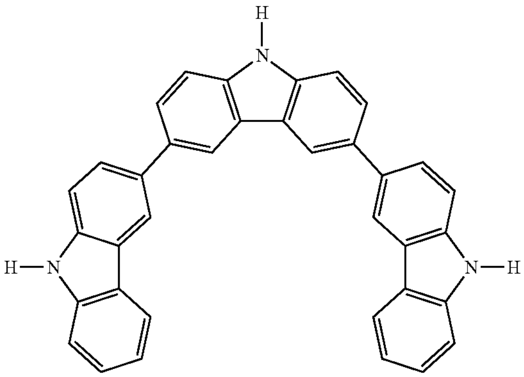<br>1346675-22-6 | 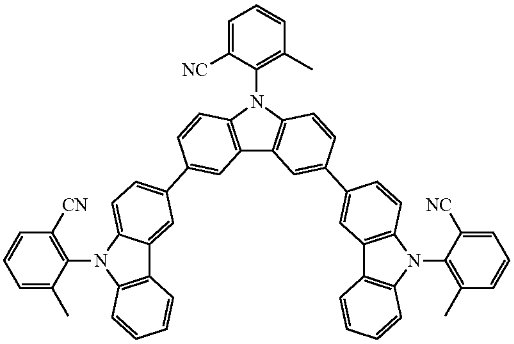 [SMILES: Cc1cccc(C#N)c1-n1c2ccccc2c2cc(-c3ccc4c(c3)c3cc(-c5ccc6c(c5)c5ccccc5n6-c5c(C)cccc5C#N)ccc3n4-c3c(C)cccc3C#N)ccc21] | 13% |

Example S64

1,3,5-Triscyano-2-(N-carbazolyl)-4,6-bis-(N-3,6-diphenylcarbazolyl)benzene, S64

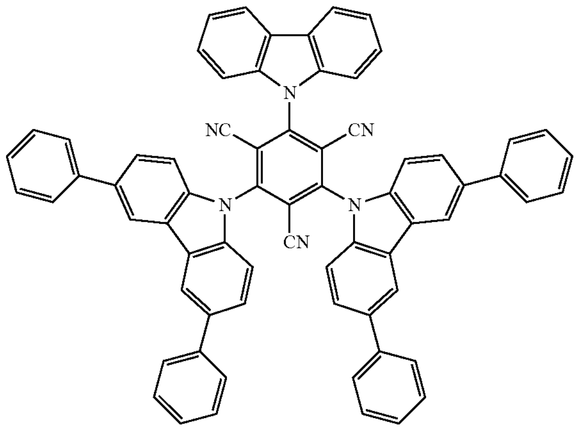 [SMILES: N#Cc1c(-n2c3ccccc3c3ccccc32)c(C#N)c(-n2c3ccc(-c4ccccc4)cc3c3cc(-c4ccccc4)ccc32)c(C#N)c1-n1c2ccc(-c3ccccc3)cc2c2cc(-c3ccccc3)ccc21]

To a well-stirred suspension of 4.0 g (100 mmol) of sodium hydride, 60% by weight dispersion in mineral oil, in 500 mL of THF are added in portions while cooling with ice, at about +10° C., 16.7 g (100 mmol) of carbazole [51555-21-6]—Caution! Evolution of hydrogen! Foaming! After the addition has ended, the mixture is stirred for a further 30 min and then 20.7 g (100 mmol) of 1,3,5-tricyano-2-fluoro-4,6-dichlorobenzene [25751-93-7] are added in portions while cooling with ice in such a way that the temperature does not exceed +20° C. After the addition has ended, the mixture is stirred at +10° C. for a further 2 h, then the cooling bath is removed, and the mixture is allowed to warm to 20-25° C., stirred for a further 2 h and then heated to 40° C. for another 6 h. After cooling to room temperature, 12.0 g (300 mmol) of sodium hydride, 60% by weight dispersion in mineral oil, are added, the reaction mixture is cooled to +10° C., and then 95.8 g (300 mmol) of 3,6-diphenylcarbazole [56525-79-2] are added in portions—Caution! Evolution of hydrogen! Foaming! After the addition has ended, the mixture is stirred at +10° C. for a further 2 h, then the cooling bath is removed, and the mixture is allowed to warm to 20-25° C., stirred for a further 2 h and then heated to 60° C. for another 16 h. After cooling to room temperature, the reaction is ended by dropwise addition of 30 mL of MeOH and the reaction mixture is then concentrated almost to dryness under reduced pressure. The residue is subjected to hot extractive stirring twice with 600 mL each time of a mixture of 400 mL of methanol and 200 mL of water and then once with 500 mL of methanol. Purification is effected by recrystallization from dioxane (about 3.5 mL/g) three times, then recrystallization from DMF (about 2 mL/g) five times and fractional sublimation twice (p about $1\times10^{-5}$ mbar, T about 330-340° C.). Yield: 22.9 g (24.0 mmol) 24%. Purity: 99.9% by HPLC.

In an analogous manner, the following compounds are prepared:

| Ex. | Reactants | Product | Yield |
|---|---|---|---|
| S65 | 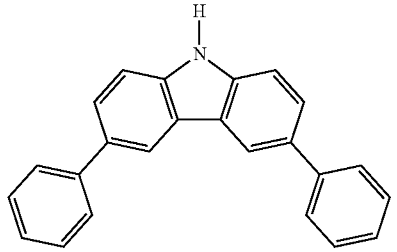 [SMILES: c1ccc(-c2ccc3[nH]c4ccc(-c5ccccc5)cc4c3c2)cc1] 56525-79-2 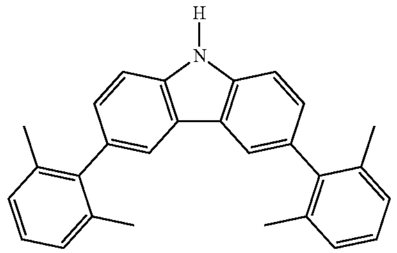 [SMILES: Cc1cccc(C)c1-c1ccc2[nH]c3ccc(-c4c(C)cccc4C)cc3c2c1] 1246891 | 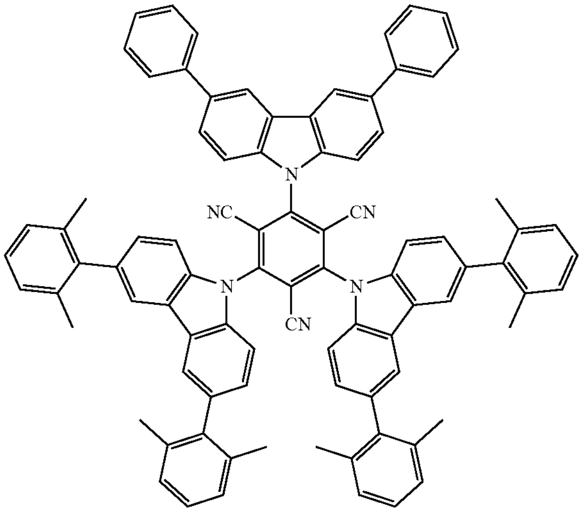 [SMILES: Cc1cccc(C)c1-c1ccc2c(c1)c1cc(-c3c(C)cccc3C)ccc1n2-c1c(C#N)c(-n2c3ccc(-c4ccccc4)cc3c3cc(-c4ccccc4)ccc32)c(C#N)c(-n2c3ccc(-c4c(C)cccc4C)cc3c3cc(-c4c(C)cccc4C)ccc32)c1C#N] | 20% |

-continued
| Ex. | Reactants | Product | Yield |
| --- | --- | --- | --- |
| S66 | 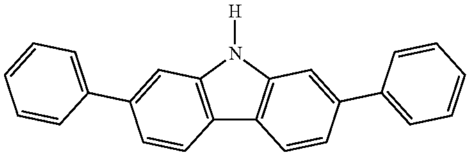 [SMILES: c1ccc(-c2ccc3c(c2)[nH]c2cc(-c4ccccc4)ccc23)cc1]<br>42448-04-4<br>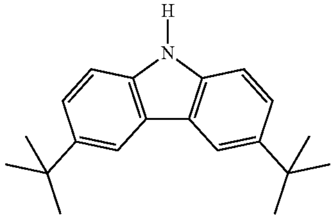 [SMILES: CC(C)(C)c1ccc2[nH]c3ccc(C(C)(C)C)cc3c2c1]<br>37500-95-1 | 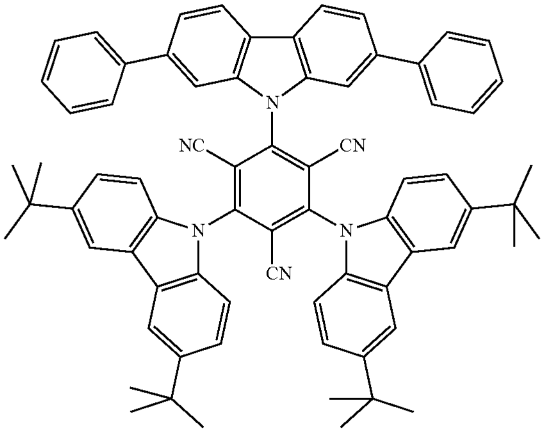 [SMILES: CC(C)(C)c1ccc2c(c1)c1cc(C(C)(C)C)ccc1n2-c1c(C#N)c(-n2c3ccc(C(C)(C)C)cc3c3cc(C(C)(C)C)ccc32)c(C#N)c(-n2c3cc(-c4ccccc4)ccc3c3ccc(-c4ccccc4)cc32)c1C#N] | 19% |
| S67 | 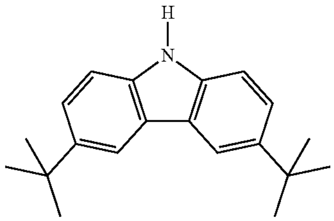 [SMILES: CC(C)(C)c1ccc2[nH]c3ccc(C(C)(C)C)cc3c2c1]<br>37500-95-1<br>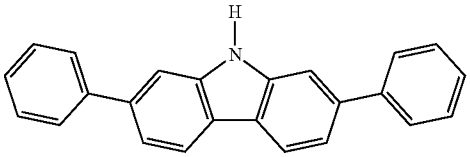 [SMILES: c1ccc(-c2ccc3c(c2)[nH]c2cc(-c4ccccc4)ccc23)cc1]<br>42448-04-4 | 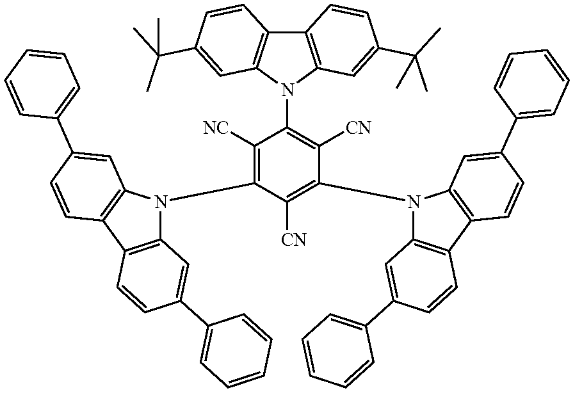 [SMILES: CC(C)(C)c1ccc2c3ccc(C(C)(C)C)cc3n(-c3c(C#N)c(-n4c5cc(-c6ccccc6)ccc5c5ccc(-c6ccccc6)cc54)c(C#N)c(-n4c5cc(-c6ccccc6)ccc5c5ccc(-c6ccccc6)cc54)c3C#N)c2c1] | 21% |
| S68 | 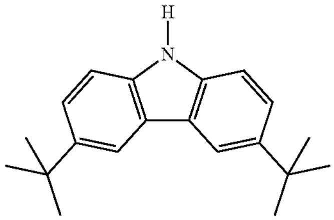 [SMILES: CC(C)(C)c1ccc2[nH]c3ccc(C(C)(C)C)cc3c2c1]<br>37500-95-1<br>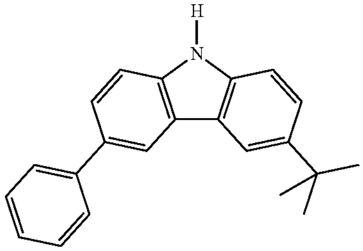 [SMILES: CC(C)(C)c1ccc2[nH]c3ccc(-c4ccccc4)cc3c2c1]<br>1335126-51-6 | 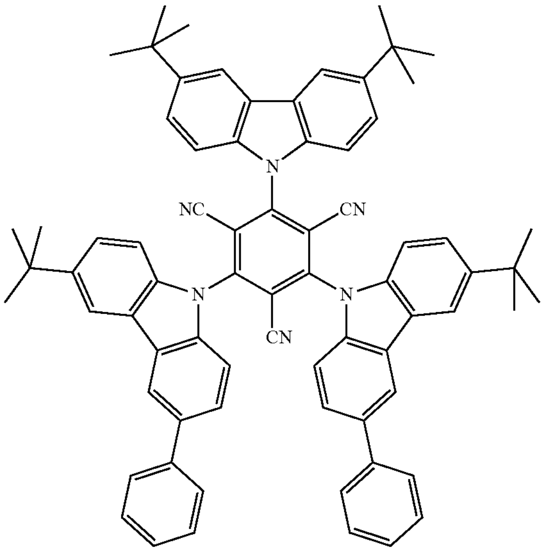 [SMILES: CC(C)(C)c1ccc2c(c1)c1cc(-c3ccccc3)ccc1n2-c1c(C#N)c(-n2c3ccc(-c4ccccc4)cc3c3cc(C(C)(C)C)ccc32)c(C#N)c(-n2c3ccc(C(C)(C)C)cc3c3cc(C(C)(C)C)ccc32)c1C#N] | 24% |

-continued
| Ex. | Reactants | Product | Yield |
| --- | --- | --- | --- |
| S69 | 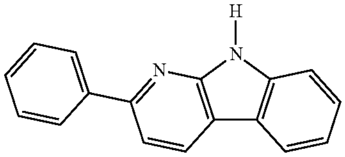 [SMILES: c1ccc(-c2ccc3c(n2)[nH]c2ccccc23)cc1]<br>64677-58-3<br>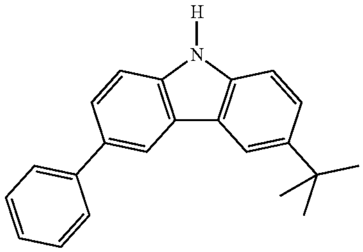 [SMILES: CC(C)(C)c1ccc2[nH]c3ccc(-c4ccccc4)cc3c2c1]<br>1335126-51-6 | 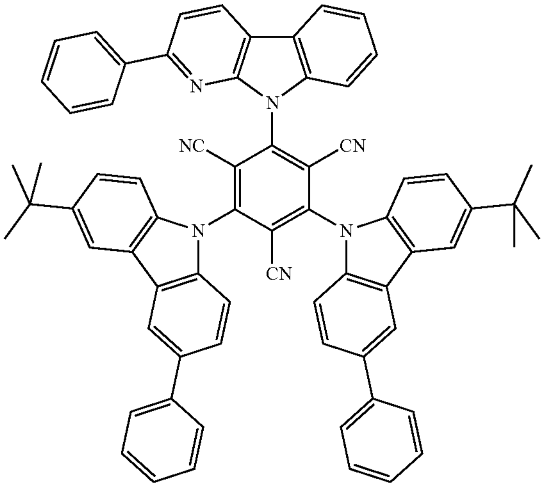 [SMILES: CC(C)(C)c1ccc2c(c1)c1cc(-c3ccccc3)ccc1n2-c1c(C#N)c(-n2c3ccc(-c4ccccc4)cc3c3cc(C(C)(C)C)ccc32)c(C#N)c(-n2c3ccccc3c3ccc(-c4ccccc4)nc32)c1C#N] | 17% |
| S70 | 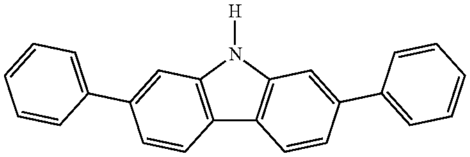 [SMILES: c1ccc(-c2ccc3c(c2)[nH]c2cc(-c4ccccc4)ccc23)cc1]<br>42448-04-4<br>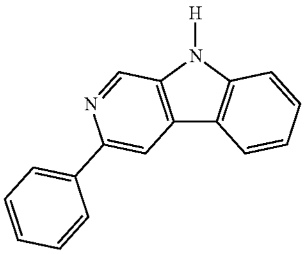 [SMILES: c1ccc(-c2cc3c(cn2)[nH]c2ccccc23)cc1]<br>91944-01-3 | 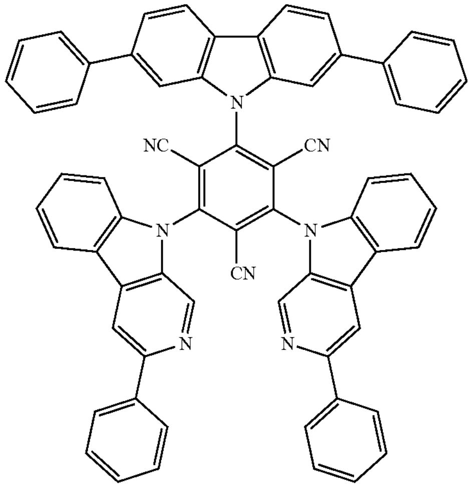 [SMILES: N#Cc1c(-n2c3ccccc3c3cc(-c4ccccc4)ncc32)c(C#N)c(-n2c3cc(-c4ccccc4)ccc3c3ccc(-c4ccccc4)cc32)c(C#N)c1-n1c2ccccc2c2cc(-c3ccccc3)ncc21] | 18% |
| S71 | 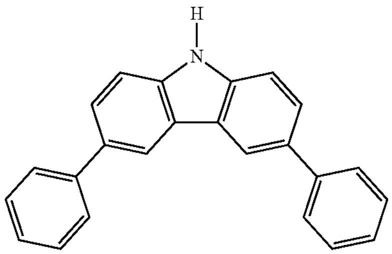 [SMILES: c1ccc(-c2ccc3[nH]c4ccc(-c5ccccc5)cc4c3c2)cc1]<br>56525-79-2<br>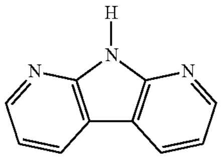 [SMILES: c1cnc2[nH]c3ncccc3c2c1]<br>17966-00-6 | 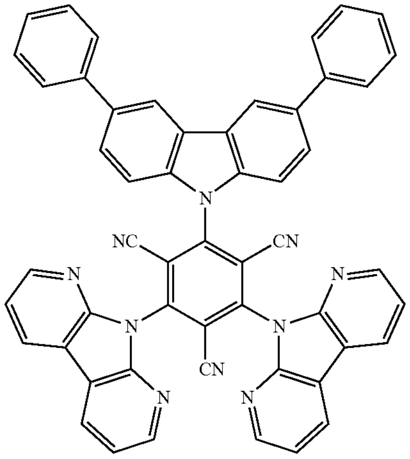 [SMILES: N#Cc1c(-n2c3ccc(-c4ccccc4)cc3c3cc(-c4ccccc4)ccc32)c(C#N)c(-n2c3ncccc3c3cccnc32)c(C#N)c1-n1c2ncccc2c2cccnc21] | 20% |

II) Synthesis of Precursors

Example S72-V

9-(2,6-Dibromophenyl)-9H-carbazole

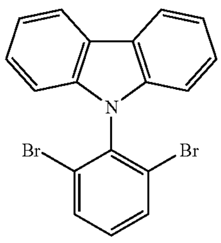 [SMILES: Brc1cccc(Br)c1-n1c2ccccc2c2ccccc21]

A well-stirred suspension of 66.9 g (400 mmol) of carbazole [51555-21-6], 25.4 g (100 mmol) of 1,3-dibromo-2-fluorobenzene [363897-9], 106.1 g (500 mmol) of tripotassium phosphate (anhydrous) and 200 g of glass beads is stirred in 500 mL of dimethylacetamide at 160° C. for 16 h. After cooling, 1000 mL of water are added, the precipitated solids are filtered off, and these are washed twice with 300 mL each time of water and twice with 200 mL each time of methanol, and then dried under reduced pressure. After a single recrystallization from toluene/heptane, 18.9 g (47.2 mmol, 47%) are obtained and then converted further.

The following are converted analogously:

| Ex. | Reactants | Product | Yield |
|---|---|---|---|
| S73-V | 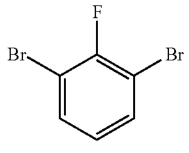 363897-9 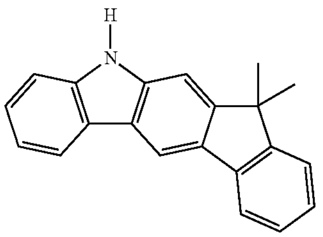 1.1 equivalents 51555-21-6 | 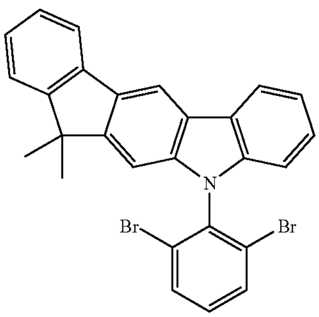 [SMILES: CC1(C)c2ccccc2-c2cc3c4ccccc4n(-c4c(Br)cccc4Br)c3cc21] | 28% |

Example S74-V

9-[2-Bromo-6-(4,4,5,5-tetramethyl-[1,3,2]dioxaborolanyl)phenyl]-9H-carbazole

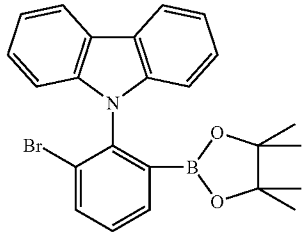 [SMILES: CC1(C)OB(c2cccc(Br)c2-n2c3ccccc3c3ccccc32)OC1(C)C]

18.5 (46.1 mmol, 1 eq) of S72-V are initially charged together with 14.1 g (55.3 mmol, 1.2 eq) of bis(pinacolato) diborane (CAS 73183-34-3) and 15.8 g (161 mmol, 3.5 eq) of potassium acetate (CAS 127-08-2) in 100 mL of THF and, after degassing, 2.26 g (0.06 eq) of 1,1-bis(diphenylphosphino)ferrocenedichloropalladium(II) complex with DCM (CAS 95464-05-4) are added. The mixture is heated at reflux for 14 h and, after the reaction has ended, water is added. The organic phase is removed and the aqueous phase is extracted repeatedly with dichloromethane. The combined organic phases are dried over sodium sulfate and the solvent is removed under reduced pressure. 15.3 g (34.1 mmol, 74%) of the product S74-V are obtained.

The following are converted analogously:

| Ex. | Reactants | Product | Yield |
|---|---|---|---|
| S75-V | 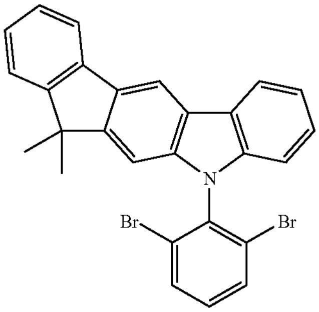 [SMILES: CC1(C)c2ccccc2-c2cc3c4ccccc4n(-c4c(Br)cccc4Br)c3cc21] | 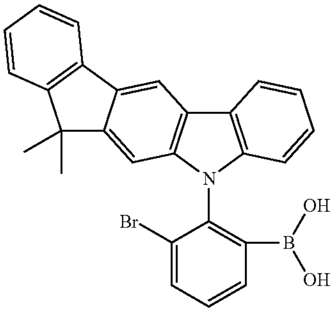 [SMILES: CC1(C)c2ccccc2-c2cc3c4ccccc4n(-c4c(Br)cccc4B(O)O)c3cc21] | 67% |

Example S76-V

9-[2-Bromo-6-(4,6-diphenyl-[1,3,5]triazin-2-yl)phenyl]-9H-carbazole S76-V

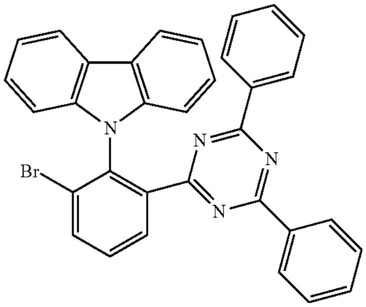 [SMILES: Brc1cccc(-c2nc(-c3ccccc3)nc(-c3ccccc3)n2)c1-n1c2ccccc2c2ccccc21]

Variant A 15.0 g (33.5 mmol) of S74-V, 11.6 g (43.5 mmol, 1.3 eq) of 2-chloro-4,6-diphenyl-1,3,5-triazine (CAS 3842-55-5) and 5.3 g of sodium carbonate are suspended in 200 mL of dioxane, 200 mL of toluene and 100 mL of water. To this suspension are added 1.94 g (1.68 mmol, 0.05 eq.) of $Pd(PPh_3)_4$. The reaction mixture is heated under reflux overnight. After cooling, the precipitated solids are filtered off with suction, washed with water and ethanol, and dried. The residue is subjected to hot extraction with toluene and recrystallized from toluene/heptane. 7.23 g (13.1 mmol, 39%) of the product S76-V are obtained.

The following are converted analogously:

| Ex. | Variant | Reactants | Product | Yield |
|---|---|---|---|---|
| S77-V | B | 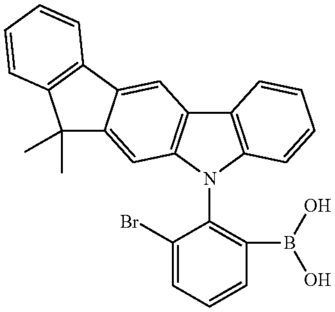 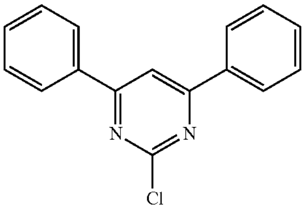 2915-16-4 | 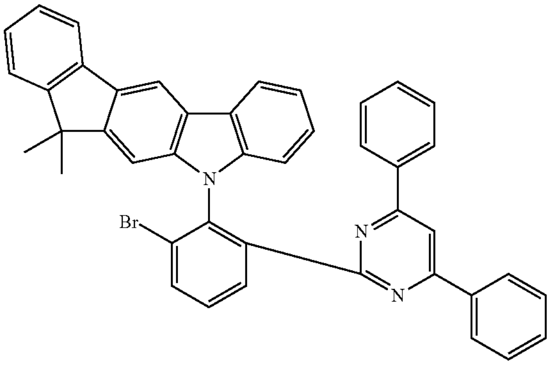 Product is converted further after single recrystallization | 39% |

III) Synthesis of Compounds of the Invention and Precursors:

Example S78

9-[3-(4,6-Diphenyl-[1,3,5]triazin-2-yl)-biphenyl-2-yl]-9H-carbazole

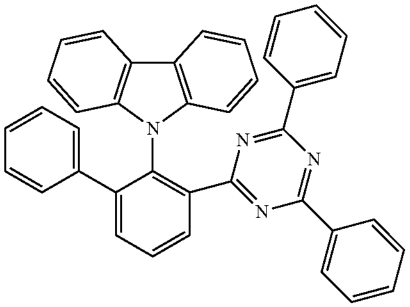 [SMILES: c1ccc(-c2nc(-c3ccccc3)nc(-c3cccc(-c4ccccc4)c3-n3c4ccccc4c4ccccc43)n2)cc1]

7.1 g (12.8 mmol) of S76-V, 1.72 g (14.1 mmol, 1.1 eq) of phenylboronic acid (CAS 98-80-6) and 5.45 g (25.7 mmol, 2 eq) of tripotassium phosphate are dissolved in 100 mL of dioxane, 100 mL of toluene and 50 mL of water, and degassed for 30 minutes. Subsequently, 86 mg (0.38 mmol, 0.03 eq.) of palladium(II) acetate and 230 mg (0.77 mmol, 0.06 eq.) of tri-o-tolylphosphine are added and the mixture is heated to reflux. After the reaction has ended, the mixture is cooled, and the aqueous phase is removed and extracted repeatedly with toluene. The combined organic phases are washed with water and dried over sodium sulfate, and the solvent is removed under reduced pressure. The residue is subjected to hot extraction with toluene and recrystallized from toluene/heptane. After sublimation, 4.1 g (7.4 mmol, 58%) of the desired product S78 are obtained with an HPLC purity of >99.9%.

| Ex. | Variant Reactants | Product | Yield |
|---|---|---|---|
| S79 | B 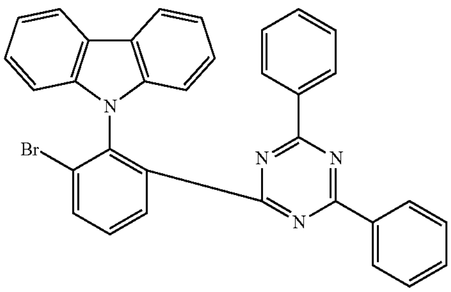 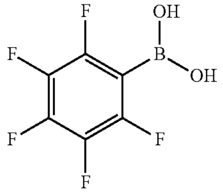 1582-24-7 | 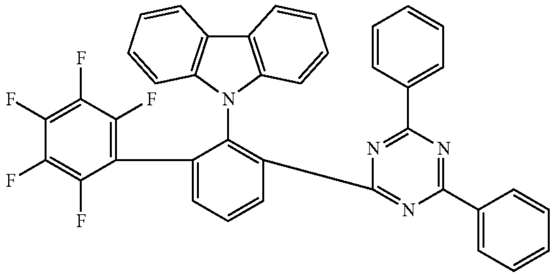 [SMILES: Fc1c(F)c(F)c(-c2cccc(-c3nc(-c4ccccc4)nc(-c4ccccc4)n3)c2-n2c3ccccc3c3ccccc32)c(F)c1F] | 37% |
| S80 | A 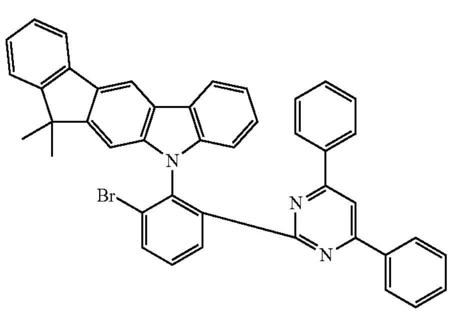 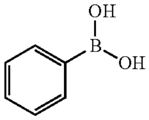 98-80-6 | 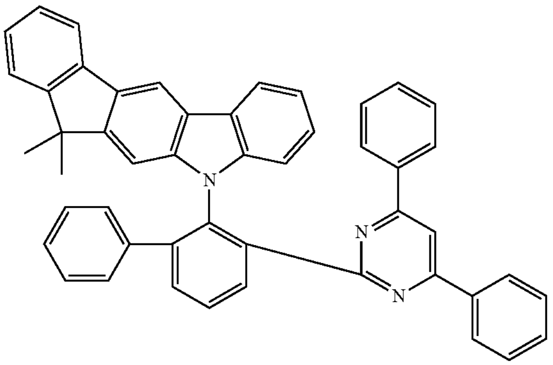 [SMILES: CC1(C)c2ccccc2-c2cc3c4ccccc4n(-c4c(-c5ccccc5)cccc4-c4nc(-c5ccccc5)cc(-c5ccccc5)n4)c3cc21] | 64% |

IV) Synthesis of Precursors:

Example S81-V

4'-Bromo-2,3,4,5,6-pentafluoro-3',5'-bis(trifluoromethyl)biphenyl

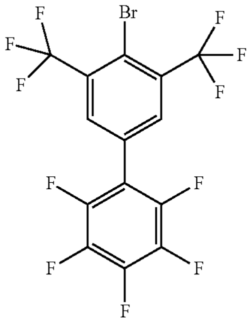 [SMILES: Fc1c(F)c(F)c(-c2cc(C(F)(F)F)c(Br)c(C(F)(F)F)c2)c(F)c1F]

To a solution of 11.4 g (30 mmol) of 2,3,4,5,6-pentafluoro-3',5'-bis(trifluoromethyl)biphenyl [1363958-46-6] in 300 mL of dichloromethane is added dropwise, with exclusion of light, a mixture of 1.7 mL (32 mmol) of bromine and 20 mL of chloroform. After stirring at 40° C. for 16 h, 200 mL of ethanol and then 50 mL of saturated sodium sulfite solution are added. The colorless solid is filtered off with suction, washed three times with 200 mL of water and three times with 100 mL of ethanol, dried under reduced pressure and then separated from isomers by recrystallizing in DMF and toluene. Yield: 4.1 g (9 mmol), 30% of theory In an analogous manner, it is possible to obtain the following compounds:

| Ex. | Reactant 1 | Product | Yield |
|---|---|---|---|
| S82-V | 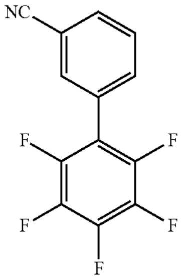 [SMILES: N#Cc1cccc(-c2c(F)c(F)c(F)c(F)c2F)c1] [1261665-44-4] | 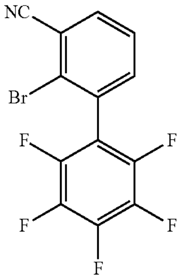 [SMILES: N#Cc1cccc(-c2c(F)c(F)c(F)c(F)c2F)c1Br] | 32% |
| S83-V | 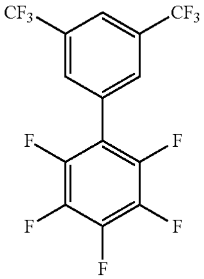 [SMILES: Fc1c(F)c(F)c(-c2cc(C(F)(F)F)cc(C(F)(F)F)c2)c(F)c1F] [1363958-46-6] | 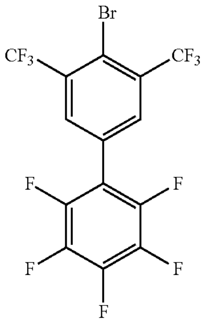 [SMILES: Fc1c(F)c(F)c(-c2cc(C(F)(F)F)c(Br)c(C(F)(F)F)c2)c(F)c1F] | 69% |
| S84-V | 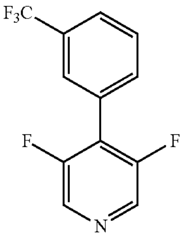 [SMILES: Fc1cncc(F)c1-c1cccc(C(F)(F)F)c1] [1261886-30-9] | 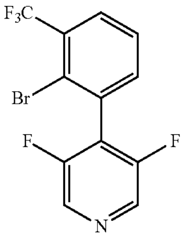 [SMILES: Fc1cncc(F)c1-c1cccc(C(F)(F)F)c1Br] | 31% |

-continued
| Ex. | Reactant 1 | Product | Yield |
|---|---|---|---|
| S85-V | 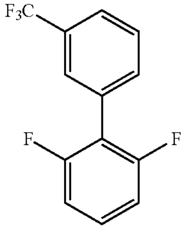 [SMILES: Fc1cccc(F)c1-c1cccc(C(F)(F)F)c1] [1261805-15-5] | 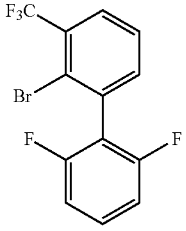 [SMILES: Fc1cccc(F)c1-c1cccc(C(F)(F)F)c1Br] | 27% |
| S86-V | 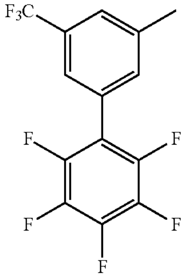 [SMILES: Cc1cc(-c2c(F)c(F)c(F)c(F)c2F)cc(C(F)(F)F)c1] [1261494-38-5] | 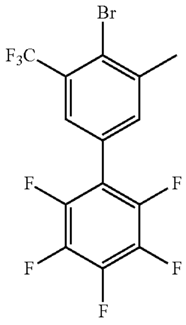 [SMILES: Cc1cc(-c2c(F)c(F)c(F)c(F)c2F)cc(C(F)(F)F)c1Br] | 55% |
| S87-V | 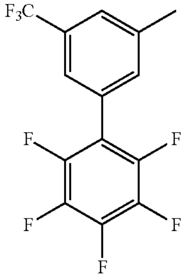 [SMILES: Cc1cc(-c2c(F)c(F)c(F)c(F)c2F)cc(C(F)(F)F)c1] [1261494-38-5] | 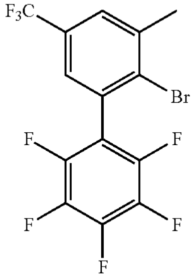 | 30% |
| S88-V | 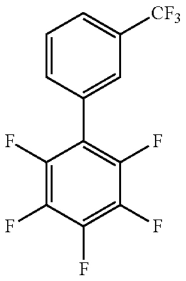 [SMILES: Fc1c(F)c(F)c(-c2cccc(C(F)(F)F)c2)c(F)c1F] [56880-53-6] | 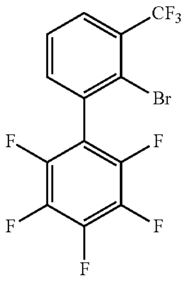 [SMILES: Fc1c(F)c(F)c(-c2cccc(C(F)(F)F)c2Br)c(F)c1F] | 29% |

-continued

| Ex. | Reactant 1 | Product | Yield |
|---|---|---|---|
| S89-V | 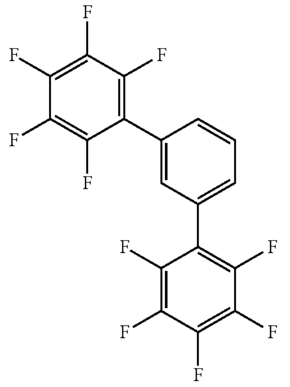 [SMILES: Fc1c(F)c(F)c(-c2cccc(-c3c(F)c(F)c(F)c(F)c3F)c2)c(F)c1F] [54826-31-2] | 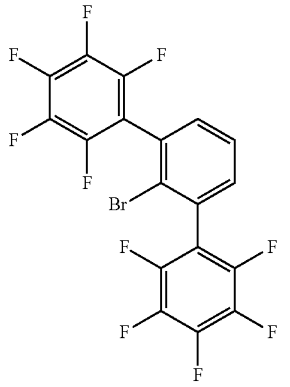 [SMILES: Fc1c(F)c(F)c(-c2cccc(-c3c(F)c(F)c(F)c(F)c3F)c2Br)c(F)c1F] | 27% |
| S90-V | 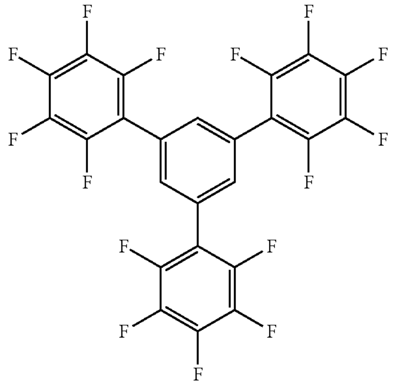 [SMILES: Fc1c(F)c(F)c(-c2cc(-c3c(F)c(F)c(F)c(F)c3F)cc(-c3c(F)c(F)c(F)c(F)c3F)c2)c(F)c1F] [61371-30-0] | 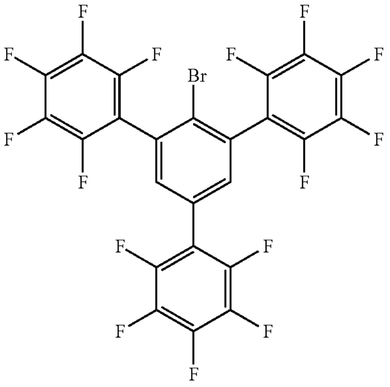 [SMILES: Fc1c(F)c(F)c(-c2cc(-c3c(F)c(F)c(F)c(F)c3F)c(Br)c(-c3c(F)c(F)c(F)c(F)c3F)c2)c(F)c1F] | 37% |

V) Synthesis of Compounds of the Invention:

Example S91

9-(2,6-Dimethylphenyl)-9H-[3,9']bicarbazolyl

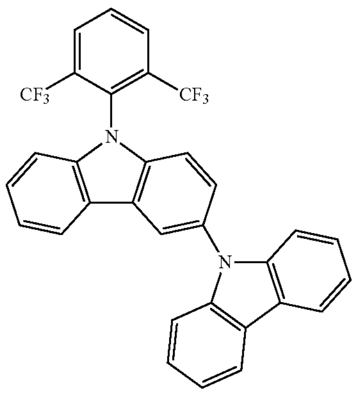 [SMILES: FC(F)(F)c1cccc(C(F)(F)F)c1-n1c2ccccc2c2cc(-n3c4ccccc4c4ccccc43)ccc21]

12.6 g (38.32 mmol) of 9H-[3,9']bicarbazolyl [18628-07-4], 7 g (38.32 mmol) of 2-bromo-1,3-ditrifluoromethylbenzene [118527-30-3] and 16 g of $K_2CO_3$ are suspended in 300 mL of p-xylene. To the suspension are added 0.86 g (3.84 mmol) of $Pd(OAc)_2$ and 7.6 mL of a 1M tri-tert-butylphosphine solution. The reaction mixture is heated under reflux for 16 h. After cooling, the organic phase is removed, washed three times with 200 mL of water and then concentrated to dryness. The residue is subjected to hot extraction with toluene, recrystallized from toluene and finally sublimed under high vacuum. Yield: 14.5 g (35 mmol), 87% of theory; purity 99.9%

In an analogous manner, it is possible to obtain the following compounds:

| | Reactant 1 | Reactant 1 | Product | Yield |
|---|---|---|---|---|
| S92 | 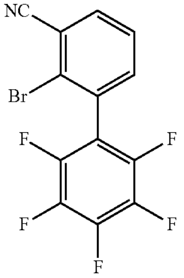 [SMILES: N#Cc1cccc(-c2c(F)c(F)c(F)c(F)c2F)c1Br] | 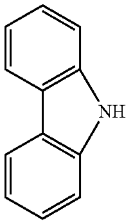 [SMILES: c1ccc2c(c1)[nH]c1ccccc12] | 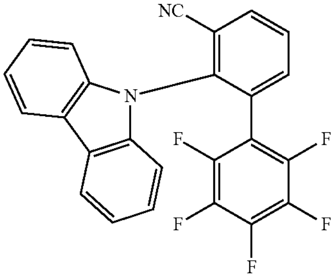 [SMILES: N#Cc1cccc(-c2c(F)c(F)c(F)c(F)c2F)c1-n1c2ccccc2c2ccccc21] | 77% |
| S93 | 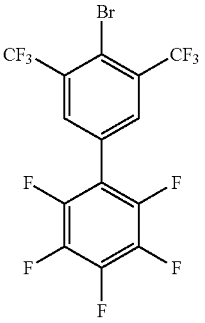 [SMILES: Fc1c(F)c(F)c(-c2cc(C(F)(F)F)c(Br)c(C(F)(F)F)c2)c(F)c1F] | 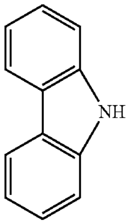 [SMILES: c1ccc2c(c1)[nH]c1ccccc12] | 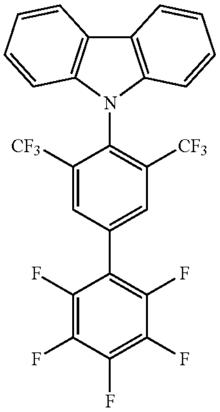 [SMILES: Fc1c(F)c(F)c(-c2cc(C(F)(F)F)c(-n3c4ccccc4c4ccccc43)c(C(F)(F)F)c2)c(F)c1F] | 68% |
| S94 | 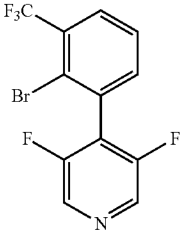 [SMILES: Fc1cncc(F)c1-c1cccc(C(F)(F)F)c1Br] | 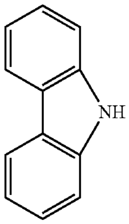 [SMILES: c1ccc2c(c1)[nH]c1ccccc12] | 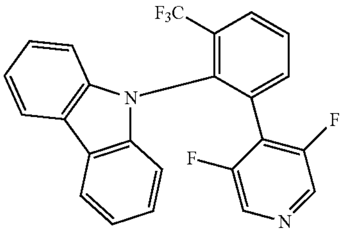 [SMILES: Fc1cncc(F)c1-c1cccc(C(F)(F)F)c1-n1c2ccccc2c2ccccc21] | 76% |
| S95 | 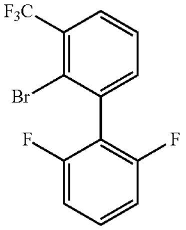 [SMILES: Fc1cccc(F)c1-c1cccc(C(F)(F)F)c1Br] | 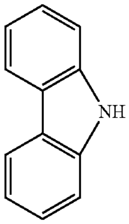 [SMILES: c1ccc2c(c1)[nH]c1ccccc12] | 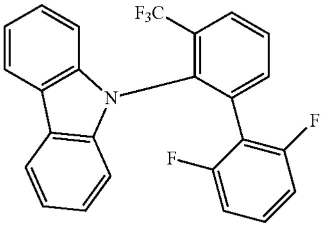 [SMILES: Fc1cccc(F)c1-c1cccc(C(F)(F)F)c1-n1c2ccccc2c2ccccc21] | 69% |
| S96 | 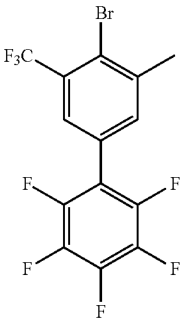 [SMILES: Cc1cc(-c2c(F)c(F)c(F)c(F)c2F)cc(C(F)(F)F)c1Br] | 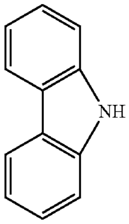 [SMILES: c1ccc2c(c1)[nH]c1ccccc12] | 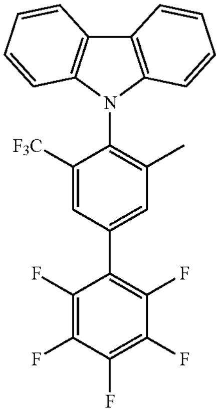 [SMILES: Cc1cc(-c2c(F)c(F)c(F)c(F)c2F)cc(C(F)(F)F)c1-n1c2ccccc2c2ccccc21] | 81% |

-continued
| | Reactant 1 | Reactant 1 | Product | Yield |
|---|---|---|---|---|
| S97 | 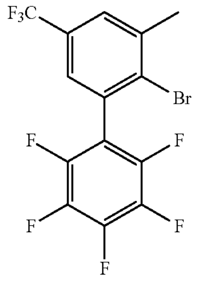 [SMILES: Cc1cc(C(F)(F)F)cc(-c2c(F)c(F)c(F)c(F)c2F)c1Br] | 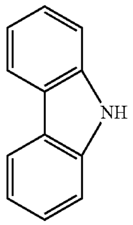 [SMILES: c1ccc2c(c1)[nH]c1ccccc12] | 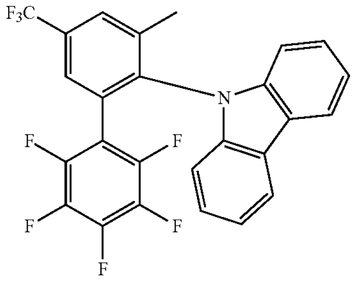 [SMILES: Cc1cc(C(F)(F)F)cc(-c2c(F)c(F)c(F)c(F)c2F)c1-n1c2ccccc2c2ccccc21] | 63% |
| S98 | 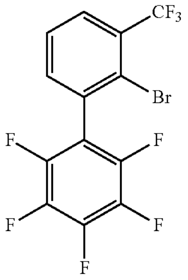 [SMILES: Fc1c(F)c(F)c(-c2cccc(C(F)(F)F)c2Br)c(F)c1F] | 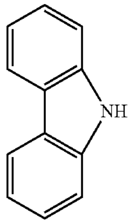 [SMILES: c1ccc2c(c1)[nH]c1ccccc12] | 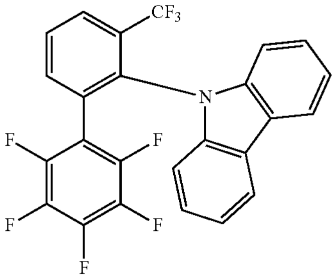 [SMILES: Fc1c(F)c(F)c(-c2cccc(C(F)(F)F)c2-n2c3ccccc3c3ccccc32)c(F)c1F] | 59% |
| S99 | 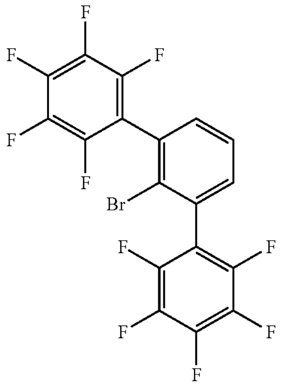 [SMILES: Fc1c(F)c(F)c(-c2cccc(-c3c(F)c(F)c(F)c(F)c3F)c2Br)c(F)c1F] | 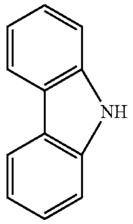 [SMILES: c1ccc2c(c1)[nH]c1ccccc12] | 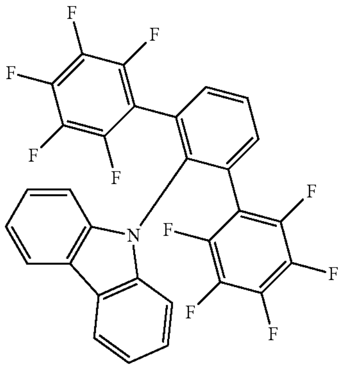 [SMILES: Fc1c(F)c(F)c(-c2cccc(-c3c(F)c(F)c(F)c(F)c3F)c2-n2c3ccccc3c3ccccc32)c(F)c1F] | 52% |
| S100 | 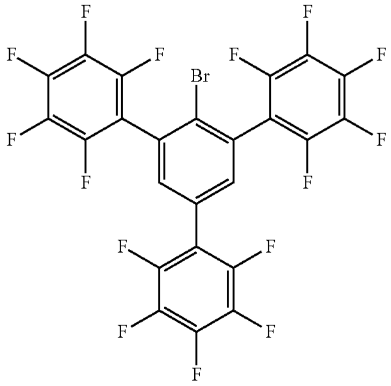 [SMILES: Fc1c(F)c(F)c(-c2cc(-c3c(F)c(F)c(F)c(F)c3F)c(Br)c(-c3c(F)c(F)c(F)c(F)c3F)c2)c(F)c1F] | 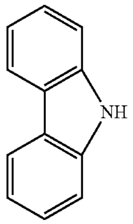 [SMILES: c1ccc2c(c1)[nH]c1ccccc12] | 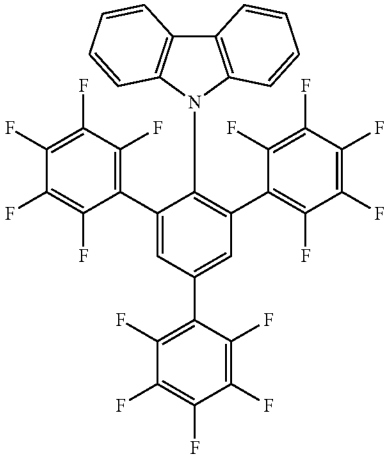 [SMILES: Fc1c(F)c(F)c(-c2cc(-c3c(F)c(F)c(F)c(F)c3F)c(-n3c4ccccc4c4ccccc43)c(-c3c(F)c(F)c(F)c(F)c3F)c2)c(F)c1F] | 48% |

-continued
| | Reactant 1 | Reactant 1 | Product | Yield |
|---|---|---|---|---|
| S101 | 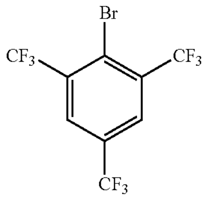 [SMILES: FC(F)(F)c1cc(C(F)(F)F)c(Br)c(C(F)(F)F)c1] [95606-57-8] | 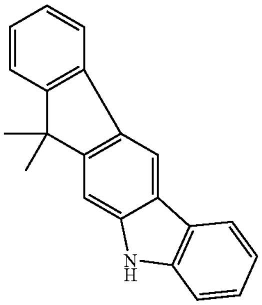 [SMILES: CC1(C)c2ccccc2-c2cc3c(cc21)[nH]c1ccccc13] [1257220-47-5] | 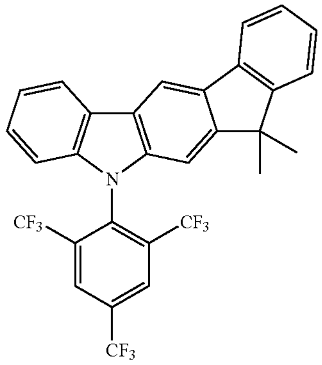 [SMILES: CC1(C)c2ccccc2-c2cc3c4ccccc4n(-c4c(C(F)(F)F)cc(C(F)(F)F)cc4C(F)(F)F)c3cc21] | 79% |
| S102 | 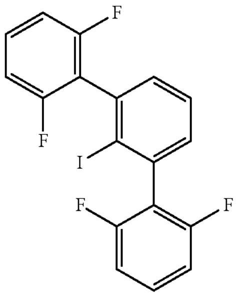 [SMILES: Fc1cccc(F)c1-c1cccc(-c2c(F)cccc2F)c1I] [1231208-09-5] | 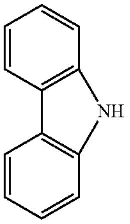 [SMILES: c1ccc2c(c1)[nH]c1ccccc12] | 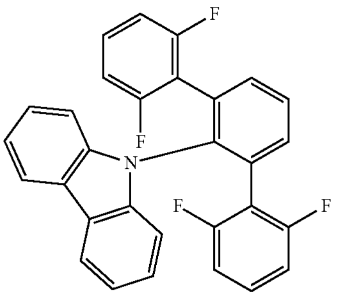 [SMILES: Fc1cccc(F)c1-c1cccc(-c2c(F)cccc2F)c1-n1c2ccccc2c2ccccc21] | 74% |
| S103 | 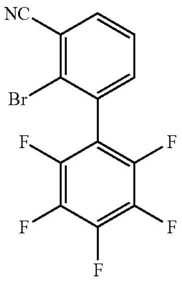 [SMILES: N#Cc1cccc(-c2c(F)c(F)c(F)c(F)c2F)c1Br] | 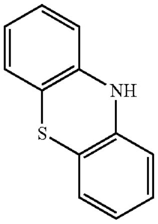 [SMILES: c1ccc2c(c1)Nc1ccccc1S2] [92-84-2] | 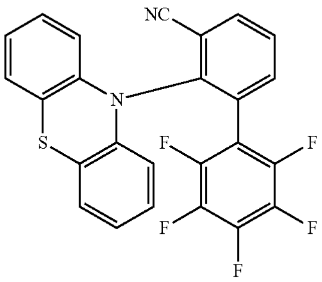 [SMILES: N#Cc1cccc(-c2c(F)c(F)c(F)c(F)c2F)c1N1c2ccccc2Sc2ccccc21] | 76% |
| S104 | 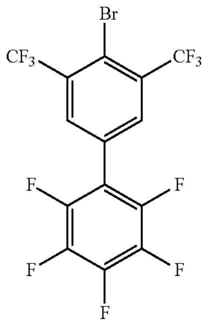 [SMILES: Fc1c(F)c(F)c(-c2cc(C(F)(F)F)c(Br)c(C(F)(F)F)c2)c(F)c1F] | 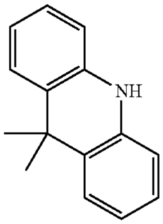 [SMILES: CC1(C)c2ccccc2Nc2ccccc21] [6267-02-3] | 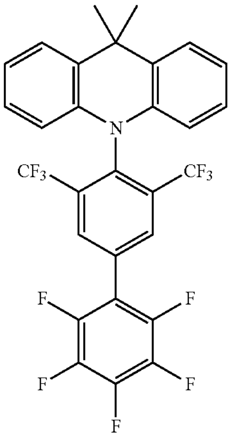 [SMILES: CC1(C)c2ccccc2N(c2c(C(F)(F)F)cc(-c3c(F)c(F)c(F)c(F)c3F)cc2C(F)(F)F)c2ccccc21] | 71% |

-continued

| | Reactant 1 | Reactant 1 | Product | Yield |
|---|---|---|---|---|
| S105 | 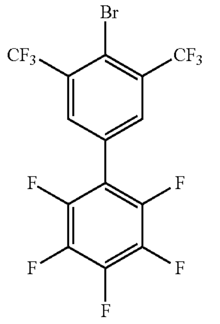 [SMILES: Fc1c(F)c(F)c(-c2cc(C(F)(F)F)c(Br)c(C(F)(F)F)c2)c(F)c1F] | 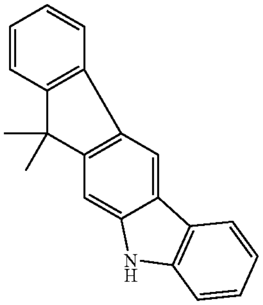 [SMILES: CC1(C)c2ccccc2-c2cc3c(cc21)[nH]c1ccccc13] [1257220-47-5] | 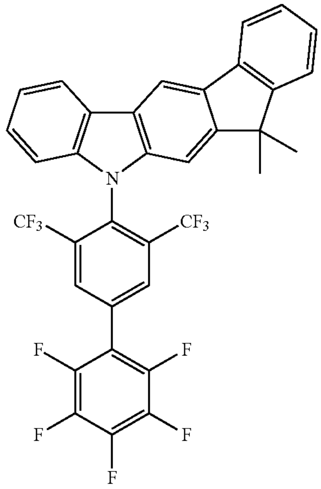 [SMILES: CC1(C)c2ccccc2-c2cc3c4ccccc4n(-c4c(C(F)(F)F)cc(-c5c(F)c(F)c(F)c(F)c5F)cc4C(F)(F)F)c3cc21] | 75% |

VI) Synthesis of Precursors:

Example S106-V

2',3',4',5',6'-Pentafluoro-3-trifluoromethylbiphenyl-2-ylamine

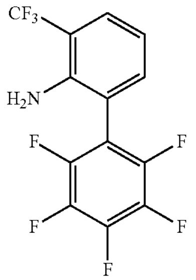 [SMILES: Nc1c(-c2c(F)c(F)c(F)c(F)c2F)cccc1C(F)(F)F]

294 mL of concentrated hydrochloric acid, 700 mL of ethanol and 38 g (126 mmol) of 2,3,4,5,6-pentafluoro-2'-nitro-3'-trifluoromethylbiphenyl [1261680-28-7] are initially charged, and 35 g (294 mmol) of tin powder are added in portions at room temperature. After the addition, the mixture is stirred at room temperature for 3 h. Thereafter, the reaction mixture is adjusted to pH=12 by addition of NaOH (solid) while cooling with ice. The residue is filtered off, washed with dichloromethane and recrystallized from heptane. This gives 22 g (79 mmol) of a white solid, corresponding to 63% of theory.

In an analogous manner, it is possible to obtain the following compounds with 2 eq. of tin powder:

| | Reactant 1 | Product | Yield |
|---|---|---|---|
| S107-V | 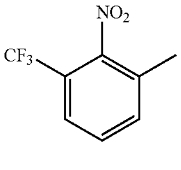 | 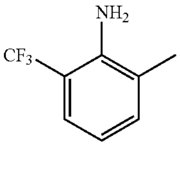 | 61% |

-continued

| | Reactant 1 | Product | Yield |
|---|---|---|---|
| S108-V | 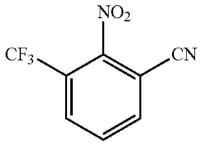 | 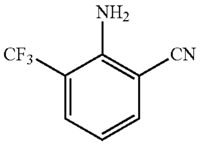 [SMILES: N#Cc1cccc(C(F)(F)F)c1N] | 68% |

VII) Synthesis of Compounds of the Invention:

Example S109

9-(3,2',3',4',5',6'-Hexafluorobiphenyl-2-yl)-9H-carbazole

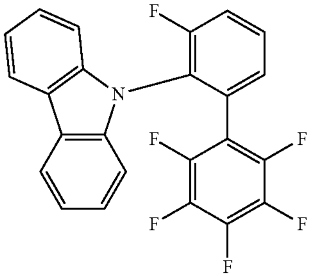 [SMILES: Fc1cccc(-c2c(F)c(F)c(F)c(F)c2F)c1-n1c2ccccc2c2ccccc21]

15.6 g (50 mmol) of 2,2'-dibromobiphenyl are admixed with 500 mL of toluene, 2.3 g (2.5 mmol) of tris(dibenzylideneacetone)dipalladium(0), 10 mL of 1M t-$Bu_3P$ in toluene and 11.5 g (120 mmol) of sodium tert-butoxide. Subsequently, 11.8 g (40 mmol) of 2',3',4',5',6'-pentafluoro-3-trifluoromethylbiphenyl-2-ylamine are added. The mixture is heated to 110° C. for 20 h, then cooled to room temperature, and 400 mL of water are added. The mixture is extracted with ethyl acetate, then the combined organic phases are dried over sodium sulfate and concentrated under reduced pressure. The residue is recrystallized from toluene and from dichloromethane/isopropanol and finally sublimed under high vacuum. The purity is 99.9%. The yield is 10 g (23 mmol), corresponding to 59% of theory.
In an analogous manner, it is possible to obtain the following compounds:
| | Reactant 1 | | Product | Yield |
|---|---|---|---|---|
| S110 | 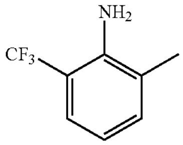 [88301-98-8] | 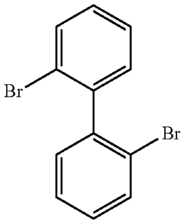 [SMILES: Brc1ccccc1-c1ccccc1Br] [13029-09-9] | 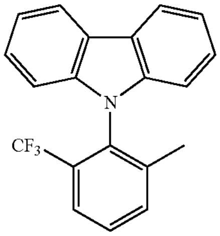 [SMILES: Cc1cccc(C(F)(F)F)c1-n1c2ccccc2c2ccccc21] | 67% |
| S111 | 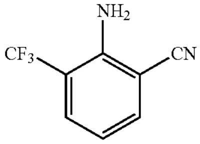 [SMILES: N#Cc1cccc(C(F)(F)F)c1N] [58458-14-3] | 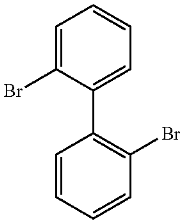 [SMILES: Brc1ccccc1-c1ccccc1Br] [13029-09-9] | 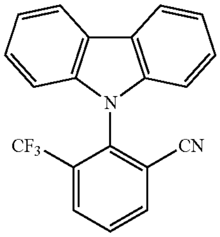 [SMILES: N#Cc1cccc(C(F)(F)F)c1-n1c2ccccc2c2ccccc21] | 67% |
| S112 | 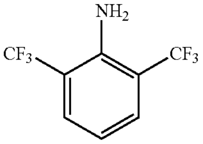 [SMILES: Nc1c(C(F)(F)F)cccc1C(F)(F)F] [313-13-3] | 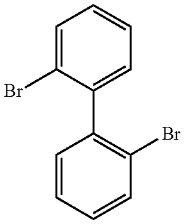 [SMILES: Brc1ccccc1-c1ccccc1Br] [13029-09-9] | 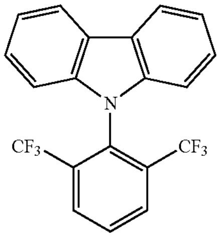 [SMILES: FC(F)(F)c1cccc(C(F)(F)F)c1-n1c2ccccc2c2ccccc21] | 59% |
| S113 | 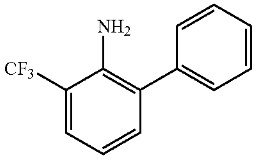 [SMILES: Nc1c(-c2ccccc2)cccc1C(F)(F)F] [1214363-65-1] | 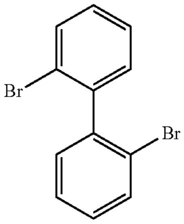 [SMILES: Brc1ccccc1-c1ccccc1Br] [13029-09-9] | 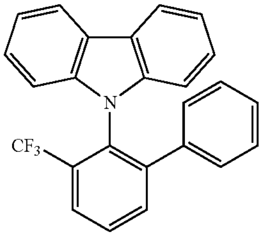 [SMILES: FC(F)(F)c1cccc(-c2ccccc2)c1-n1c2ccccc2c2ccccc21] | 58% |
| S114 | 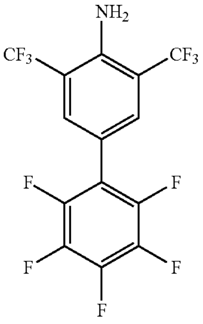 [SMILES: Nc1c(C(F)(F)F)cc(-c2c(F)c(F)c(F)c(F)c2F)cc1C(F)(F)F] | 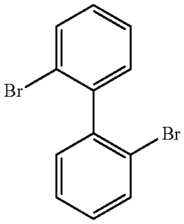 [SMILES: Brc1ccccc1-c1ccccc1Br] [13029-09-9] | 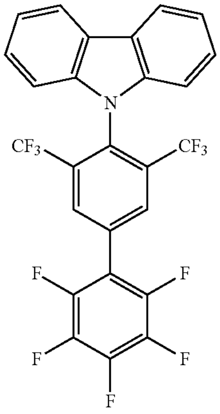 [SMILES: Fc1c(F)c(F)c(-c2cc(C(F)(F)F)c(-n3c4ccccc4c4ccccc43)c(C(F)(F)F)c2)c(F)c1F] | 68% |

-continued
| | Reactant 1 | | Product | Yield |
| --- | --- | --- | --- | --- |
| S115 | 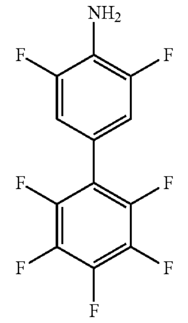 [SMILES: Nc1c(F)cc(-c2c(F)c(F)c(F)c(F)c2F)cc1F] [1261616-30-1] | 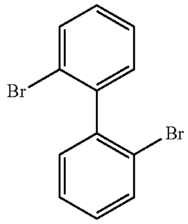 [SMILES: Brc1ccccc1-c1ccccc1Br] [13029-09-9] | 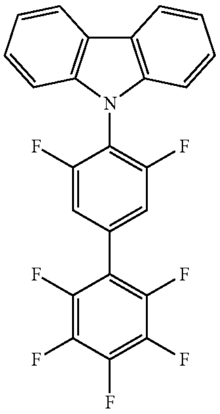 [SMILES: Fc1cc(-c2c(F)c(F)c(F)c(F)c2F)cc(F)c1-n1c2ccccc2c2ccccc21] | 63% |
| S116 | 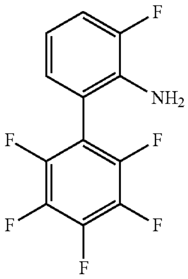 [SMILES: Nc1c(F)cccc1-c1c(F)c(F)c(F)c(F)c1F] [1261759-86-7] | 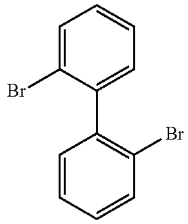 [SMILES: Brc1ccccc1-c1ccccc1Br] [13029-09-9] | 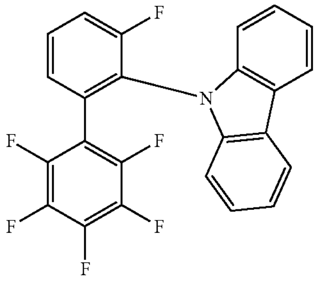 [SMILES: Fc1cccc(-c2c(F)c(F)c(F)c(F)c2F)c1-n1c2ccccc2c2ccccc21] | 55% |
| S117 | 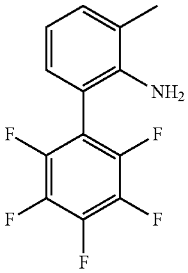 [SMILES: Cc1cccc(-c2c(F)c(F)c(F)c(F)c2F)c1N] [264926-99-0] | 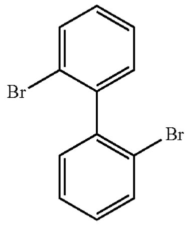 [SMILES: Brc1ccccc1-c1ccccc1Br] [13029-09-9] | 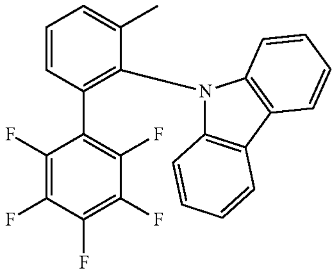 [SMILES: Cc1cccc(-c2c(F)c(F)c(F)c(F)c2F)c1-n1c2ccccc2c2ccccc21] | 46% |
| S118 | 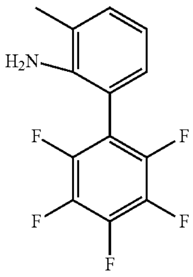 [SMILES: Cc1cccc(-c2c(F)c(F)c(F)c(F)c2F)c1N] [264926-99-0] | 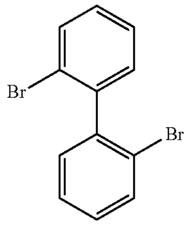 [SMILES: Brc1ccccc1-c1ccccc1Br] [13029-09-9] | 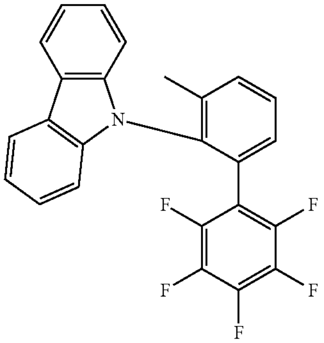 [SMILES: Cc1cccc(-c2c(F)c(F)c(F)c(F)c2F)c1-n1c2ccccc2c2ccccc21] | 52% |

-continued

| | Reactant 1 | | Product | Yield |
|---|---|---|---|---|
| S119 | 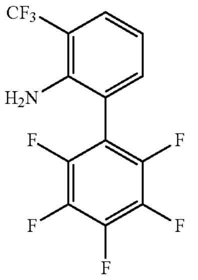 [SMILES: Nc1c(-c2c(F)c(F)c(F)c(F)c2F)cccc1C(F)(F)F] | 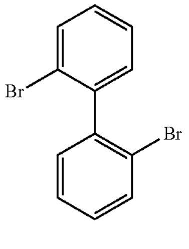 [SMILES: Brc1ccccc1-c1ccccc1Br] [13029-09-9] | 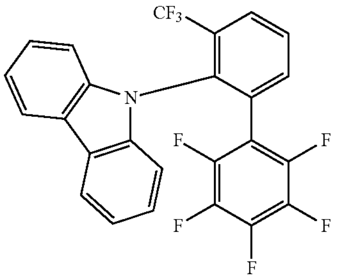 [SMILES: Fc1c(F)c(F)c(-c2cccc(C(F)(F)F)c2-n2c3ccccc3c3ccccc32)c(F)c1F] | 43% |

B) Device Examples

In the examples which follow, the results of various OLEDs in which the compounds of the invention are used as emitting compounds are presented.

Glass plaques which have been coated with structured ITO (indium tin oxide) are the substrates for the OLEDs. The substrates are subjected to wet cleaning (cleaning machine, detergent: Merck Extran), then baked at 250° C. for 15 min and, prior to the coating, treated with an oxygen plasma.

All materials are applied by thermal vapor deposition in a vacuum chamber. The emission layer always consists of a matrix material and the emitting material. The latter is added to the matrix material in a particular proportion by volume by coevaporation.

The OLEDs are characterized in a standard manner. The electroluminescence spectra are determined at a luminance of 1000 cd/$m^2$, and the CIE 1931 x and y color coordinates are calculated therefrom. In addition, the voltage which is required for a luminance of 1000 cd/$m^2$ is determined. Table 1 additionally reports the external quantum efficiency which is achieved at an operating luminance of 1000 cd/$m^2$. This is determined assuming Lambertian radiation characteristics.

Type 1

Substrate:

ITO, 50 nm

Hole Injection Layer/Hole Transport Layer:

4,4-bis[N-(1-naphthyl)-N-phenylamino]biphenyl, α-NPD, [123847-85-8], 90 nm

Emission Layer:

4,4'-bis(N-carbazole)biphenyl CBP, [58328-31-7], as matrix material, doped with 5% by volume of the compound of the invention (see table 1) as dopant, 15 nm Electron Transport Layer:

1,3,5-tri(1-phenyl-1H-benzimidazol-2-yl)benzene TPBi, [192198-85-9], 50 nm

Electron Injection Layer:

LiF, 1 nm

Cathode:

Al, 100 nm

Type 1a

Same construction as type 1, except that an α-NPD layer of thickness 120 rather than 90 nm and a TPBI layer of thickness 60 rather than 50 nm is used.

Type 2

Substrate:

ITO, 50 nm

Hole Injection Layer/Hole Transport Layer:

4,4-bis[N-(1-naphthyl)-N-phenylamino]biphenyl, α-NPD, [123847-85-8], 80 nm

Hole Transport Layer:

1,3-bis(9-carbazolyl)benzene, mCP, [550378-78-4], 10 nm

Emission Layer:

2,8-bis(diphenylphosphoryl)dibenzo[b,d]thiophene, PPT, [1019842-99-9], as matrix material, doped with 5% by volume of the compound of the invention (see table 1) as dopant, 20 nm Electron Transport Layer:

2,8-bis(diphenylphosphoryl)dibenzo[b,d]thiophene, PPT, [1019842-99-9], 50 nm

Electron Injection Layer:

LiF, 1 nm

Cathode:

Al, 100 nm

Use of Compounds of the Invention as Emitter Materials in OLEDs

The compounds of the invention can especially be used as emitter materials in the emission layer of OLEDs. The values measured for power efficiency, voltage and color coordinates are summarized in table 1.

TABLE 1

| Ex. | Emitter | Type | EQE (%) 1000 cd/$m^2$ | Voltage (V) 1000 cd/$m^2$ | CIE x/y 1000 cd/$m^2$ |
|---|---|---|---|---|---|
| P1 | S1 | 2 | 14.0 | 7.3 | 0.42/0.56 |
| P2 | S6 | 1 | 12.8 | 7.1 | 0.45/0.55 |
| P3 | S23 | 1 | 12.1 | 5.7 | 0.41/0.57 |
| P4 | S32 | 1 | 13.0 | 6.3 | 0.36/0.59 |
| P5 | S36 | 2 | 14.4 | 7.7 | 0.40/0.57 |
| P6 | S47 | 2 | 15.5 | 8.3 | 0.14/0.19 |
| P7 | S49 | 1 | 18.5 | 5.8 | 0.23/0.54 |
| P8 | S52 | 2 | 16.8 | 6.6 | 0.15/0.28 |
| P9 | S54 | 1 | 17.2 | 4.7 | 0.22/0.52 |
| P10 | S61 | 2 | 13.8 | 7.6 | 0.15/0.27 |
| P11 | S64 | 1a | 13.8 | 6.3 | 0.59/0.41 |
| P-V1 | Comp. 1 | 2 | 1.8 | 4.6 | 0.14/0.06 |
| P-V2 | Comp. 2 | 1 | 1.3 | 3.7 | 0.69/0.31 |

The OLEDs produced exhibit excellent values for power efficiency. By using different emitters, it is possible to obtain light having different color coordinates.

The comparison with compounds according to the prior art (Comp. 1 and Comp. 2 in P-V1 and P-V2) shows an outstanding improvement in power efficiency at similar voltages through replacement of these compounds with the compounds of the invention.

Compounds of comparative examples P-1 and P-V2:

Comp. 1

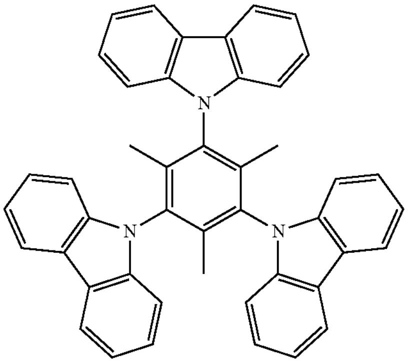

Comp. 2

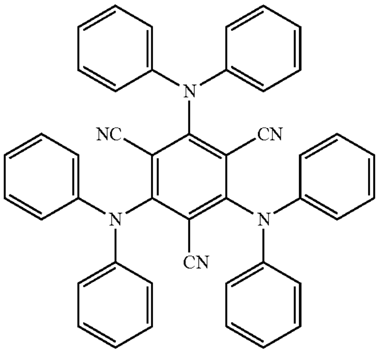

The invention claimed is:

1. A compound of the formula (I)

Formula (I)

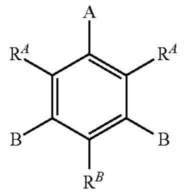

or a compound containing exactly two or three units of the formula (I) joined to one another via a single bond or an L group, where:

L is any divalent or trivalent organic group;

A is a group of the formula (A)

Formula (A)

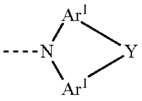

bonded via the dotted bond;

$Ar^1$ is the same or different at each instance and is an aromatic or heteroaromatic ring system which has 5 to 30 aromatic ring atoms and may be substituted by one or more $R^1$ radicals;

Y is the same or different at each instance and is a single bond, $BR^1$, $C(R^1)_2$, $Si(R^1)_2$, $NR^1$, $PR^1$, $P(=O)R^1$, O, S, S=O or $S(=O)_2$;

B is the same or different at each instance and is selected from H, a straight-chain alkyl group having 1 to 10 C atoms or a branched or cyclic alkyl group having 3 to 10 C atoms, each of which may be substituted by one or more $R^1$ radicals, or an aryl group having 6 to 14 aromatic ring atoms, each of which may be substituted by one or more $R^1$ radicals;

$R^A$ is the same or different at each instance and is $CF_3$, CN, and an E group, which is an aryl or heteroaryl group which has 6 to 14 aromatic ring atoms and may be substituted by one or more $R^1$ radicals, and which contains one or more V groups as constituents of the aromatic ring, where the V groups are the same or different at each instance and are selected from =N—, =C(F)—, =C(CN)— and =$C(CF_3)$—, and where the heteroaryl group is not bonded via a nitrogen atom;

$R^B$ is selected from H, a straight-chain alkyl group having 1 to 10 carbon atoms or a branched or cyclic alkyl group having 3 to 10 carbon atoms, each of which may be substituted by one or more $R^1$ radicals, and an aryl group having 6 to 14 aromatic ring atoms, which may be substituted by one or more $R^1$ radicals;

$R^1$ is the same or different at each instance and is H, D, F, $C(=O)R^2$, CN, $Si(R^2)_3$, $N(R^2)_2$, $P(=O)(R^2)_2$, $OR^2$, $S(=O)R^2$, $S(=O)_2R^2$, a straight-chain alkyl or alkoxy group having 1 to 20 carbon atoms or a branched or cyclic alkyl or alkoxy group having 3 to 20 carbon atoms, where the abovementioned groups may each be substituted by one or more $R^2$ radicals and where one or more $CH_2$ groups in the abovementioned groups may be replaced by $—R^2C=CR^2—$, —C≡C—, $Si(R^2)_2$, C=O, $C=NR^2$, —C(=O)O—, $—C(=O)NR^2—$, $NR^2$, $P(=O)(R^2)$, —O—, —S—, SO or $SO_2$, or an aromatic or heteroaromatic ring system having 5 to 30 aromatic ring atoms, each of which may be substituted by one or more $R^2$ radicals, where two or more $R^1$ radicals may be joined to one another and may form a ring;

$R^2$ is the same or different at each instance and is H, D, F or an aliphatic, aromatic or heteroaromatic organic radical having 1 to 20 carbon atoms, in which one or more hydrogen atoms may also be replaced by D or F; at the same time, two or more $R^2$ substituents may be joined to one another and may form a ring.

2. The compound as claimed in claim 1, wherein the L group is a divalent group selected from alkylene groups having 1 to 20 carbon atoms, in which one or more $CH_2$ groups may be replaced by $Si(R^1)_2$, O, S, C=O, $C=NR^1$, C=O—O, $C=O—NR^1$, $NR^1$, $P(=O)(R^1)$, SO or $SO_2$ and which may be substituted by one or more $R^1$ radicals, or aromatic or heteroaromatic ring systems having 5 to 30 aromatic ring atoms, each of which may be substituted by one or more $R^1$ radicals, or is a trivalent group selected from aromatic or heteroaromatic ring systems having 5 to 30 aromatic ring atoms, each of which may be substituted by one or more $R^1$ radicals.

3. The compound as claimed in claim 1, wherein $Ar^1$ is the same or different at each instance and is an aromatic ring system which has 6 to 20 aromatic ring atoms and may be substituted by one or more $R^1$ radicals.

4. The compound as claimed in claim 1, wherein the Y group is the same or different at each instance and is a single bond, $C(R^1)_2$, $NR^1$, O or S.

5. The compound as claimed in claim 1, wherein the B group is the same or different at each instance and is H.

6. The compound as claimed in claim 1, wherein the two $R^A$ radicals are the same or different and are CN.

7. The compound as claimed in claim 1, wherein $R^B$ is the same or different at each instance and is H.

8. The compound as claimed in claim 1, wherein the compound of the formula (I) corresponds to formula (I-3)

Formula (I-3)

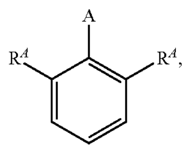

where the A and $R^A$ groups are each as defined in claim 1.

9. A process for preparing the compound of formula (I) as claimed in claim 1, which comprises introducing at least one carbazole derivative by nucleophilic aromatic substitution or Buchwald coupling, or in that at least one electron-deficient heteroaryl group is introduced by Suzuki coupling.

10. An oligomer containing one or more compounds of formula (I) as claimed in claim 1, wherein the bond(s) to the oligomer may be localized at any positions substituted by $R^1$ or $R^2$ in formula (I).

11. An electronic device comprising at least one compound as claimed in claim 1.

12. An electronic device comprising at least one oligomer as claimed in claim 10.

13. An organic electroluminescent device comprising anode, cathode and at least one emitting layer, wherein at least one organic layer in the device, selected from emitting layers, comprises at least one compound as claimed in claim 1.

14. An organic electroluminescent device comprising anode, cathode and at least one emitting layer, wherein at least one organic layer in the device, selected from emitting layers, comprises at least one oligomer as claimed in claim 10.

15. The compound as claimed in claim 1, wherein at least one $R^A$ radical is CN.

16. The compound as claimed in claim 1, wherein $Ar^1$ is phenyl, which may be substituted by one or more radicals $R^1$.

17. The compound as claimed in claim 1, wherein $R^B$ is H and B is H.

18. The compound as claimed in claim 1, wherein $R^A$ is CN, $R^B$ is H,

B is H and $Ar^1$ is phenyl, which may be substituted by one or more radicals $R^1$.

19. A compound of the formula (I)

formula (I)

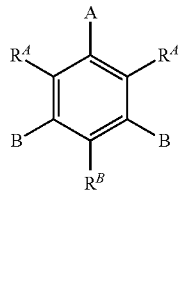

where:

A is a group of the formula (A)

Formula (A)

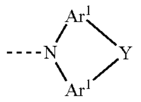

bonded via the dotted bond;

$Ar^1$ is the same or different at each instance and is an aromatic or heteroaromatic ring system which has 5 to 30 aromatic ring atoms and may be substituted by one or more $R^1$ radicals;

Y is the same or different at each instance and is a single bond, $BR^1$, $C(R^1)_2$, $Si(R^1)_2$, $NR^1$, $PR^1$, $P(=O)R^1$, O, S, S=O or $S(=O)_2$;

B is the same or different at each instance and is selected from H, a straight-chain alkyl group having 1 to 10 C atoms or a branched or cyclic alkyl group having 3 to 10 C atoms, each of which may be substituted by one or more $R^1$ radicals, or an aryl group having 6 to 14 aromatic ring atoms, each of which may be substituted by one or more $R^1$ radicals;

$R^A$ is the same or different at each instance and is $CF_3$, CN, and an E group, which is an aryl or heteroaryl group which has 6 to 14 aromatic ring atoms and may be substituted by one or more $R^1$ radicals, and which contains one or more V groups as constituents of the aromatic ring, where the V groups are the same or different at each instance and are selected from =N—, =C(F)—, =C(CN)— and $=C(CF_3)$—, and where the heteroaryl group is not bonded via a nitrogen atom;

$R^B$ is selected from H, a straight-chain alkyl group having 1 to 10 carbon atoms or a branched or cyclic alkyl group having 3 to 10 carbon atoms, each of which may be substituted by one or more $R^1$ radicals, and an aryl group having 6 to 14 aromatic ring atoms, which may be substituted by one or more $R^1$ radicals;

$R^1$ is the same or different at each instance and is H, D, F, $C(=O)R^2$, CN, $Si(R^2)_3$, $N(R^2)_2$, $P(=O)(R^2)_2$, $OR^2$, $S(=O)R^2$, $S(=O)_2R^2$, a straight-chain alkyl or alkoxy group having 1 to 20 carbon atoms or a branched or cyclic alkyl or alkoxy group having 3 to 20 carbon atoms, where the abovementioned groups may each be substituted by one or more $R^2$ radicals and where one or more $CH_2$ groups in the abovementioned groups may be replaced by $—R^2C=CR^2—$, —C≡C—, $Si(R^2)_2$, C=O, $C=NR^2$, —C(=O)O—, $—C(=O)NR^2—$, $NR^2$, $P(=O)(R^2)$, —O—, —S—, SO or $SO_2$, or an aromatic or heteroaromatic ring system having 5 to 30 aromatic ring atoms, each of which may be substituted by one or more $R^2$ radicals, where two or more $R^1$ radicals may be joined to one another and may form a ring; and $R^2$ is the same or different at each instance and is H, D, F or an aliphatic, aromatic or heteroaromatic organic radical having 1 to 20 carbon atoms, in which one or more hydrogen atoms may also be replaced by D or F; at the same time, two or more $R^2$ substituents may be joined to one another and may form a ring.

* * * * *